United States Patent [19]
Elliott et al.

[11] Patent Number: 6,001,849
[45] Date of Patent: *Dec. 14, 1999

[54] FUROPYRIDINE, THIENOPYRIDINE PYRROLOPYRIDINE USEFUL IN CONTROLLING CHEMICAL SYNAPTIC TRANSMISSION

[75] Inventors: Richard L. Elliott, Grayslake; Keith B. Ryther, Round Lake Park; Mark W. Holladay, Libertyville, all of Ill.; James T. Wasicak, Waterford; Jerome F. Daanen, Racine, both of Wis.; Nan-Horng Lin, Mundelein, Ill.; Michael J. Dart, Highland Park, Ill.; Yun He, Zion, Ill.; Yihong Li, Grayslake, Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/834,053

[22] Filed: Apr. 11, 1997

Related U.S. Application Data

[63] Continuation-in-part of application No. 08/679,237, Jul. 23, 1996, abandoned
[60] Provisional application No. 60/001,619, Jul. 28, 1995.

[51] Int. Cl.$^6$ ...................... A61K 31/435; C07D 491/048
[52] U.S. Cl. .......................... 514/300; 514/301; 514/302; 546/113; 546/114; 546/115; 546/116
[58] Field of Search ..................................... 546/113, 114, 546/115, 116; 514/300, 301, 302

[56] References Cited

FOREIGN PATENT DOCUMENTS 9705139  2/1997  WIPO .

Primary Examiner—Bernard Dentz
Attorney, Agent, or Firm—Michael J. Ward

[57] ABSTRACT

Novel heterocyclic ether compounds having the formula:

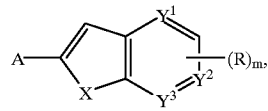

wherein A, m, R, X, $Y^1$, $Y^2$ and $Y^3$ are specifically defined, which are useful in selectively controlling chemical synaptic transmission; therapeutically-effective pharmaceutical compositions thereof; and use of said compositions to selectively control synaptic transmission in mammals.

14 Claims, No Drawings

FUROPYRIDINE, THIENOPYRIDINE PYRROLOPYRIDINE USEFUL IN CONTROLLING CHEMICAL SYNAPTIC TRANSMISSION

This application is a Continuation-in Part ("CIP") application which claims priority to U.S. Ser. No. 08/679,237 filed Jul. 23, 1996 now abandoned which is a non-provisional application which claims priority to U.S. Ser. No. 60/001,619 filed Jul. 28, 1995.

TECHNICAL FIELD

This invention relates to furopyridine, thienopyridine, pyrrolopyridine and related pyrimidine, pyridazine and triazine compounds which control chemical synaptic transmission; to therapeutically effective pharmaceutical compositions of these compounds; and to the use of said compositions to selectively control synaptic transmission.

BACKGROUND OF THE INVENTION

Compounds that selectively control chemical synaptic transmission offer therapeutic utility in treating disorders that are associated with dysfunctions in synaptic transmission. This utility may arise from controlling either pre-synaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For a fuller explanation of chemical synaptic transmission refer to Hoffman et al., "Neurotransmission: The autonomic and somatic motor nervous systems." In: *Goodman and Gilman's, The Pharmacological Basis of Therapeutics*, 9th ed., J. G. Hardman, L. E. Limbird, P. B. Molinoff, R. W. Ruddon, and A. Goodman Gilman, eds., Pergamon Press, New York, 1996, pp. 105–139).

Typically, chemical synaptic transmission begins with a stimulus that depolarizes the transmembrane potential of the synaptic junction above the threshold that elicits an all-or-none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for the particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and $K^+$), whereas IPSPs are the result of stabilization or hyperpolarization of the membrane excitability due to a increase in permeability to primarily smaller ions (including $K^+$ and $Cl^-$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See *Goodman and Gilman's, The Pharmacological Basis of Therapeutics*, op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor activation are distinct from those of muscarinic receptor activation. In an analogous manner, inhibition of nicotinic acetylcholine receptors results in still other biological effects, which are distinct and different from those arising from muscarinic receptor inhibition.

As indicated above, the two principal sites to which drug compounds that affect chemical synaptic transmission may be directed are the presynaptic nerve terminal and the postsynaptic membrane. Actions of drugs directed to the presynaptic site may be mediated through presynaptic receptors that respond to the neurotransmitter which the same secreting structure has released (i.e., through an autoreceptor), or through a presynaptic receptor that responds to another neurotransmitter (i.e., through a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system, postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it is possible to modulate the net balance of all the other inputs. Obviously, the more that is understood about chemical synaptic transmission in CNS disorders, the easier it would be to design drugs to treat such disorders.

Knowing how specific neurotransmitters act in the CNS allows one to speculate about the disorders that may be treatable with certain CNS-active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons", In: *Psychopharmacology: The Fourth Generation of Progress*, F. E. Bloom and D. J. Kupfer, Eds., Raven Press, N.Y., 1995, pp 227–243). Patients with Parkinson's disease have a primary loss of dopamnine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", In: *Psychopharmacology: The Fourth Generation of Progress*, op. cit, pp 1479–1484).

New and selective neurotransmitter controlling agents are still being sought, in the hope that one or more will be useful in important, but as yet poorly controlled, disease states or behavior models. For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention-Deficit Disorder (ADD). Specific agents for treatment of these and related disorders are few in number or non-existent.

A more complete discussion of the possible utility as CNS-active agents of compounds with activity as cholinergic ligands selective for neuronal nicotinic acetylcholine receptors, (i.e., for controlling chemical synaptic transmission) may be found in U.S. Pat. No. 5,472,958, to Gunn et al., issued Dec. 5, 1995, which is incorporated herein by reference.

Existing acetylcholine agonists are therapeutically suboptimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability (e.g., nicotine). In addition, other agents have many unwanted central agonist actions, including hypothermia, hypolocomotion and tremor and peripheral side effects, including miosis, lachrymation, defecation and tachycardia (Benowitz et al., in: *Nicotine Psychopharmacology*, S. Wonnacott, M. A. H. Russell, & I. P. Stolerman, eds., Oxford University Press, Oxford, 1990, pp. 112–157; and M. Davidson, et al., in *Current Research in Alzheimer Therapy*, E. Giacobini and R. Becker, ed.; Taylor & Francis: New York, 1988; pp 333–336).

Additional conditions for which neurotransmnitter controlling agents may be useful include acute and chronic pain. (A. Dray and L. Urban, Annu. Rev. Pharmacology Toxicol. 36: 253–280, (1996).

A 6-bromo-2-(1-piperidinyl)thieno[2,3-b]pyridine of indeterminate use was disclosed by Meth-Cohn et al., *J. Chem. Soc., Perkin Trans.*, 1:2509–17 (1981). Ciba-Geigy and Schenker et al. have disclosed various (2-benzofuranyl)-substituted tetrahydro pyridines and pyridines useful in treating mental depression (GB Patent No. 1,510,977, published May 17, 1978; and U.S. Pat. Nos. 4,210,655 and 4,600,719). Toyama has disclosed N-BOC-thienopyridine derivatives having use an intermediates for preparation of complex cephalosporin-related antibiotic agents (PCT Patent Application WO 92/18505, published Oct. 29, 1992). Kabi Pharmacia has disclosed bicyclic heteroaryl compounds attached to a quinuclidene moiety useful for treating diseases related to muscarinic receptor function (PCT Patent Application WO 93/23395, published Nov. 25, 1993). Festal et al. have disclosed urea derivatives containing an azaindole moiety having utility as hypolipidemic and antiatheromatous agents (U.S. Pat. No. 5,338,849). Baker et al. have disclosed a class of substituted azetidine, pyrrolidine and piperidine derivatives having selective activity as agonists of 5-$HT_1$-like receptors (PCT Patent Application WO 96/04274, published Feb. 15, 1996).

SUMMARY OF THE INVENTION

It has been found, in accordance with the present invention, that certain furopyridine, thienopyridine, pyrrolopyridine and related pyrimidine, pyridazine and triazine compounds are selective and potent cholinergic compounds useful in selectively controlling synaptic transmission.

In its principal aspect, the present invention provides a compound of formula (I) below, or a pharmaceutically acceptable salt thereof, wherein a monocyclic or bicyclic amine group is directly linked to a substituted or unsubstituted furopyridine, thienopyridine, pyrrolopyridine or related pyrimidine, pyridazine or triazine group.

Another aspect of the present invention provides pharmaceutical compositions comprising a therapeutically effective amount of a compound of formula (I) in combination with a pharmaceutically acceptable carrier or diluent.

In yet another aspect, the present invention provides a method for selectively controlling synaptic transmission in a mammal.

The present invention relates to a compound of formula (I):

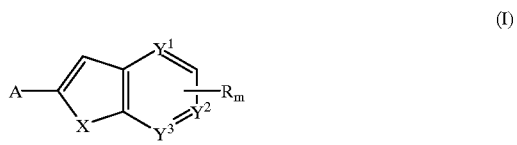

(I)

or a pharmaceutically acceptable salt or pro-drug thereof wherein:

A is selected from the group consisting of:
(a)

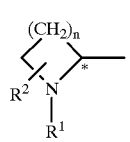

(a)

wherein
* denotes a chiral center,
n is 1, 2 or 3,
$R^1$ is selected from the group consisting of H, allyl and $C_1$–$C_3$-alkyl;
$R^2$ is selected from the group consisting of
H,
$C_1$–$C_3$-alkyl,
$C_1$–$C_3$-alkoxy,
hydroxymethyl,
fluoromethyl,
methoxymethyl, and
$R^2$, when substituted at a position other than alpha to the ring nitrogen atom, is selected from Br, Cl, F, OH, CN, —O—CO—$CH_3$ and —O—methanesulfonyl;

(b)

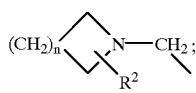

(c)

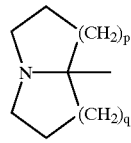

wherein p and q are independently 1 or 2;

(d)

(d)

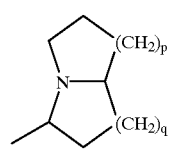

wherein p and q are independently 1 or 2;

(e)

(e)

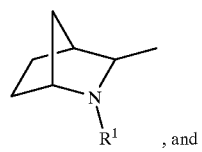

, and and (f)

(f)

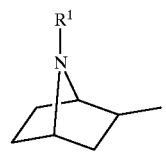

wherein, in the case of (e) and (f) $R^1$ is as described above;

R is independently selected at each occurrence from the group consisting of
$C_1$–$C_4$-alkyl,
vinyl,
bromo,
chloro,
fluoro,
trifluoro-$C_1$–$C_4$-alkyl,
trichloro-$C_1$–$C_4$-alkyl,
COOH,
$CO_2$-$C_1$–$C_4$-alkyl,
CN,
nitro,
amino,
hydroxy,
NH—CO—$C_1$–$C_3$-alkyl, and
$NR^3R^3$, wherein $R^3$ is H or $C_1$–$C_3$-alkyl; or when substituted at the $Y^2$ position can additionally be selected from:

$NR^3R^4$, wherein $R^3$ is H or C1–C3 alkyl and $R^4$ is hydrogen, $C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;

C(O)—$R^5$, where $R^5$ is hydrogen, $C_1$–$C_8$-alkyl, substituted-$C_1$–$C_8$-alkyl, phenyl, substituted phenyl, naphthyl, substituted naphthyl, heteroaryl, substituted heteroaryl, phenyl $C_1$–$C_6$alkyl-, substituted phenyl$C_1$–$C_6$alkyl-, heteroaryl $C_1$–$C_6$alkyl-, substituted heteroaryl $C_1$–$C_6$ alkyl-, and $C_1$–$C_6$alkoxy-, $NR^6R^7$, wherein $R^6$ is selected from the group consisting of H and $C_1$–$C_3$-alkyl-, and $R^7$ is selected from the group consisting of H, $C_1$–$C_3$-alkyl-, phenyl and substituted phenyl;

$OR^8$, wherein $R^8$ is $C_1$–$C_8$-alkyl, phenyl, substituted phenyl, heteroaryl, substituted heteroaryl, phenyl$C_1$–$C_6$alkyl-, substituted phenyl$C_1$–$C_6$alkyl-, heteroaryl $C_1$–$C_6$alkyl-, $CONR^3R^4$;

phenyl;
naphthyl;
substituted phenyl;
substituted naphthyl;
biphenyl;
substituted biphenyl;
heteroaryl;
substituted heteroaryl;
phenyl $C_1$–$C_6$alkyl-;
substituted phenyl$C_1$–$C_6$alkyl-;
heteroaryl $C_1$–$C_6$alkyl-; and
substituted heteroaryl$C_1$–$C_6$alkyl-;

wherein $R^9$ is selected from the group consisting of hydrogen, $C_1$–$C_8$alkyl, substituted $C_1$–$C_8$alkyl, phenyl, substituted phenyl, naphthyl, substituted naphthyl, heteroaryl, substituted heteroaryl, phenyl$C_1$–$C_6$alkyl-, substituted phenyl$C_1$–$C_6$alkyl-, heteroaryl $C_1$–$C_6$alkyl-, and substituted heteroaryl$C_1$–$C_6$alkyl-;

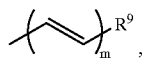

wherein m is 1 or 2, and $R^9$ is as defined above;
—$CH_2$—NH—CO—$R^5$, wherein $R^5$ is as defined above; and
—$CH_2$—$CH_2$—CO—O—$C_1$–$C_6$-alkyl;

X is —O—, —S— or —$NR^3$, wherein $R^3$ is H or $C_1$–$C_3$-alkyl;

$Y^1$, $Y^2$ and $Y^3$ are N or CH, with the provisos that at least one of $Y^1$, $Y^2$ and $Y^3$ must be N and, when group A is selected from option (b), except for those compounds additionally substituted at $Y^2$ above, then $Y^2$ and $Y^3$ must be CH;

m, on formula (I), is 0, 1, 2 or 3. When m is zero or, at those positions around the 5-6 bicyclic ring system which are not substituted by R, hydrogen is the substituent.

The novel compounds of the present invention are also represented by formula (I):

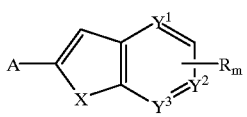

(I)

or a pharmaceutically acceptable salt or pro-drug thereof wherein the group designated A is selected from the group consisting of (a)–(f) as above:

the asterisk denotes a chiral center; m is 0, 1 or 2; n is 1, 2 or 3, and p and q are independently 1 or 2. The group $R^1$ is selected from the group consisting of H and $C_1$–$C_3$-alkyl; and $R^2$ is H, or when n is 2 or 3 is selected from the group consisting of $C_1$–$C_3$-alkyl, $C_1$–$C_3$-alkoxyl, hydroxymethyl, fluoromethyl, methoxymethyl, Br, Cl, F, OH, CN, —O—CO—$CH_3$ and —O—methanesulfonyl.

In the generic chemical structure shown above, R is independently selected at each occurrence from the group consisting of $C_1$–$C_4$-alkyl, bromo, chloro, fluoro, trifluoro-$C_1$–$C_4$-alkyl, trichloro-$C_1$–$C_4$-alkyl, COOH, $CO_2$.$C_1$–$C_4$-alkyl, CN, nitro, amino, NH—CO—$C_1$–$C_3$-alkyl, and $NR^3R^3$, wherein $R^3$ is H or $C_1$–$C_3$-alkyl.

The group designated X is selected from the group consisting of —O—, —S— or —$NR^3$, wherein $R^3$ is H or $C_1$–$C_3$-alkyl.

$Y^1$, $Y^2$ and $Y^3$ are N or CH, with the provisos that at least one of $Y^1$, $Y^2$ and $Y^3$ must be N and when group A is selected from option (b), then $Y^2$ and $Y^3$ must be CH.

In yet another aspect of the invention, the invention relates to a compound of formula (III):

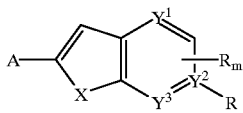

(III)

or a pharmaceutically acceptable salt or pro-drug thereof wherein:

A is selected from the group identified above; and R is independently selected at each occurrence from the group consisting of $C_1$–$C_4$-alkyl, vinyl, bromo, chloro, fluoro, trifluoro-$C_1$–$C_4$-alkyl, trichloro-$C_1$–$C_4$-alkyl, COOH, $CO_2$.$C_1$–$C_4$-alkyl, CN, nitro, amino, hydroxy, NH—CO—$C_1$–$C_3$-alkyl, and $NR^3R^3$, wherein $R^3$ is H or $C_1$–$C_3$-alkyl:

and at the $Y^2$ position R can additionally be selected from:

$NR^3R^4$, wherein $R^3$ is H or C1–C3 alkyl and $R^4$ is hydrogen, $C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;

C(O)—$R^5$, where $R^5$ is hydrogen, $C_1$–$C_8$-alkyl, substituted-$C_1$–$C_8$-alkyl, phenyl, substituted-phenyl, naphthyl, substituted naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, substituted-heteroaryl-$C_1$–$C_6$-alkyl-, and O—$C_1$–$C_6$-alkyl-, N—$R^6R^7$, wherein $R^6$ is selected from the group consisting of H and $C_1$–$C_3$-alkyl-, and $R^7$ is selected from the group consisting of H, $C_1$–$C_3$-alkyl-, phenyl and substituted-phenyl;

$OR^8$, wherein $R^8$ is $C_1$–$C_8$-alkyl, phenyl, substituted-phenyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, $CONR^3R^4$;

phenyl;
naphthyl;
substituted-phenyl;
substituted-naphthyl;
biphenyl;
substituted-biphenyl;
heteroaryl;
substituted-heteroaryl;
phenyl-$C_1$–$C_6$-alkyl-;
substituted-phenyl-$C_1$–$C_6$-alkyl-;
heteroaryl-$C_1$–$C_6$-alkyl-; and
substituted-heteroaryl-$C_1$–$C_6$-alkyl-;

wherein $R^9$ is selected from the group consisting of hydrogen, $C_1$–$C_8$-alkyl, substituted-$C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;

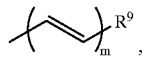

wherein m is 1 or 2, and $R^9$ is as defined above;
—$CH_2$—NH—CO—$R^5$, wherein $R^5$ is as defined above; and
—$CH_2$—$CH_2$—CO—O—$C_1$–$C_6$-alkyl;

X is —O—, —S— or —$NR^3$, wherein $R^3$ is H or $C_1$–$C_3$-alkyl;

$Y^1$, $Y^2$ and $Y^3$ are N or CH, with the provisos that at least one of $Y^1$, $Y^2$ and $Y^3$ must be N and, when group A is selected from option (b), except for those compounds additionally substituted at $Y^2$ above, then $Y^2$ and $Y^3$ must be CH methoxymethyl or methoxymethoxy and m is 0, 1 or 2.

DETAILED DESCRIPTION OF THE INVENTION

Certain compounds of this invention may possess one or more asymmetric centers and may exist in optically active forms. Additional asymmetric centers may be present in a substituent group, such as an alkyl group. Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof. The terms "R" and "S" used herein are configurations as defined in *IUPAC* 1974 *Recommendations for Section E, Fundamental Stereochemistry, Pure Appl. Chem.*, 1976, 45: 13–30.

"$C_1$–$C_3$-alkyl" and "$C_1$–$C_4$-alkyl" refer to branched or straight-chain, unsubstituted alkyl groups comprising oneto-three or one-to-four carbon atoms, including, but not limited to, methyl, ethyl, n-propyl, isopropyl, n-butyl, isobutyl, t-butyl and the like. "$C_1$–$C_6$-alkyl" or "$CC_1$–$C_8$-alkyl" as used herein refer to saturated, straight- or branched-chain hydrocarbon radicals containing between one and six or one and eight carbon atoms, respectively. Examples of $C_1$–$C_3$ alkyl radicals include methyl, ethyl, propyl and isopropyl, examples of $C_1$–$C_6$-alkyl radicals include, but are not limited to, methyl, ethyl, propyl, isopropyl, n-butyl, tert-butyl, neopentyl, n-hexyl, and examples of $C_1$–$C_8$-alkyl radicals include, but are not limited to, methyl, ethyl, propyl, isopropyl, n-butyl, tert-butyl, neopentyl, n-hexyl, n-heptyl and n-octyl.

"$C_1$–$C_3$-alkoxy" refers to a $C_1$–$C_3$-alkyl group, as defined above, containing an oxygen linker atom.

"Trichloro-$C_1$–$C_4$-alkyl" refers to a $C_1$–$C_4$-alkyl group, as defined above, substituted with three chlorine atoms, including for example, trichloromethyl, 2,2,2-trichloroethyl, 3,3,3-trichloropropyl and 4,4,4-trichlorobutyl.

"Trifluoro-$C_1$–$C_4$-alkyl refers to a $C_1$–$C_4$-alkyl group, as defined above, substituted with three fluorine atoms, including for example, trifluoromethyl, 2,2,2-trifluoroethyl, 3,3,3-trifluoropropyl and 4,4,4-trifluorobutyl.

The term, "prodrug", refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application*, edited by E. B. Roche, Pergamon Press (1987).

The term, "prodrug ester group", refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term, "administration", of the cholinergic agent or composition, as used herein, refers to systemic use as when taken orally, parenterally, by inhalation spray, by nasal, rectal or buccal routes, or topically as ointments, pastes, creams, lotions, gels, powders, solutions, sprays, inhalants or transdermal patches in dosage form unit formulations containing conventional nontoxic pharmaceutically acceptable carriers, adjuvants and vehicles as desired.

The term "parenteral", as used herein, includes intravenous, intramuscular, intraperitoneal, intrasternal, subcutaneous and intraarticular injection as well as via infusion techniques.

By "pharmaceutically acceptable", it is meant those salts, amides and esters which are, within the scope of sound medical judgment, suitable for use in contact with the tissues of humans and animals without undue toxicity, irritation, allergic response and the like, and are commensurate with a reasonable benefit/risk ratio, effective for their intended use in the treatment of psychological, neurological, cardiovascular and addictive behavior disorders. Pharmaceutically acceptable salts are well known in the art For example, S. M. Berge, et al. describe pharmaceutically acceptable salts in detail in *J. Pharmaceutical Sciences*, 66: 1–19, 1977. The salts may be prepared in situ during the final isolation and purification of the compounds of Formula (I), or separately by reacting the free base function with a suitable acid. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like. Examples of pharmaceutically acceptable, nontoxic amides of the compounds of Formula (I) include amides derived from $C_1$–$C_6$-alkyl carboxylic acids wherein the alkyl groups are straight- or branched-chain, aromatic carboxylic acids such as derivatives of benzoic acid and heterocyclic carboxylic acids, including furan-2-carboxylic acid or nicotinic acid. Amicles of the compounds of Formula (I) may be prepared according to conventional methods and include amino acid and polypeptide derivatives of the amines of Formula (I).

As used herein, the term, "pharmaceutically acceptable carriers", means a non-toxic, inert solid, semi-solid or liquid filler, diluent, encapsulating material or formulation auxiliary of any type. Some examples of the materials that may serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants may also be present in the composition, according to the judgment of the formulator. Examples of pharmaceutically acceptable antioxidants include water-soluble antioxidants, such as ascorbic acid, cysteine hydrochloride, sodium bisulfite, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By a "therapeutically effective amount" of the nicotinic acetylcholinergic agent, is meant a sufficient amount of the compound to treat cholinergically related disorders at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts. Total daily dose of the compounds of this invention administered to a host in single or divided doses may be in amounts as determined by the attending physician, typically, for example, in amounts of from about 0.001 to 100 mg/kg body weight daily and preferably 0.01 to 10 mg/kg/day. Dosage unit compositions may contain such amounts of submultiples thereof to make up the daily dose.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, such as, for example, pyridinyl, pyrazinyl, pyridazinyl, pyrimidinyl, pyrrolyl, pyrazolyl, imidazolyl, indolyl, thiazolyl, oxazolyl, isoxazolyl, thiadiazolyl, oxadiazolyl, thienyl, furanyl, quinolinyl, isoquinolinyl, and the like, the heteroaryl moiety being joined to the rest of the molecule via any of its carbon ring atoms.

The term "heteroaryl$C_1$–$C_6$alkyl" as used herein refers to a $C_1$–$C_6$-alkyl group as defined herein substituted by replacement of one of the hydrogen atoms thereon with a heteroaryl moiety, as defined above.

The term "phenyl$C_1$–$C_6$alkyl" as used herein refers to a $C_1$–$C_6$-alkyl group as defined herein substituted by replacement of one of the hydrogen atoms thereon with a phenyl moiety.

The term "substituted $C_1$–$C_8$alkyl" as used herein refers to a $C_1$–$C_8$-alkyl group as defined herein substituted by independent replacement of one of the hydrogen atoms thereon with Cl, Br, F, CN, $CF_3$, OH, CHO, COOH, COO—$C_1$–$C_3$-alkyl, $C_1$–$C_6$-alkoxy, methoxymethoxy, amino, or $C_1$–$C_3$-alkyl-amino, except not more than one CHO, COOH, or COO—$C_1$–$C_3$-alkyl group may be present.

The term "substituted biphenyl" as used herein refers to a biphenyl radical substituted by replacement of one of the hydrogen atoms thereon with F, OH, $NO_2$ or $C_1$–$C_3$-alkyl.

The term "substituted naphthyl" as used herein refers to a naphthyl substituted by independent replacement of one or two of the hydrogen atoms thereon with Cl, Br, F, CN, $CF_3$, $NO_2$, OH, CHO, COC)H, COO—$C_1$–$C_3$-alkyl, $C_1$–$C_3$-alkyl, $C_1$–$C_6$-alkoxy, methoxymethyl, methoxymethoxy, amino, or $C_1$–$C_3$-alkyl-amino, except not more than one CHO, COOH, or COO—$C_1$–$C_3$-alkyl group may be present.

The term "substituted phenyl" as used herein refers to a phenyl substituted by independent replacement of one or two of the hydrogen atoms thereon with Cl, Br, F, CN, $CF_3$, $NO_2$, OH, CHO, COOH, COO—$C_1$–$C_3$-alkyl, $C_1$–$C_3$-alkyl, $C_1$–$C_6$-alkoxy, methoxymethyl, methoxymethoxy, amino, or $C_1$–$C_3$-alkyl-amino, except not more than one CHO, COOH, or COO—$C_1$–$C_3$-alkyl group may be present.

The term "substituted phenyl$C_1$–$C_6$alkyl" as used herein refers to a $C_1$–$C_6$-alkyl group as defined herein substituted by replacement of one of the hydrogen atoms thereon with a substituted-phenyl moiety, as defined above.

The term "substituted heteroaryl" as used herein refers to a heteroaryl group as defined herein substituted on or two carbon atoms by independent replacement of he hydrogen atoms thereon with Cl, Br, F, CN, $CF_3$, $NO_2$, OH, CHO, COOH, COO—$C_1$–$C_3$-alkyl, $C_1$–$C_3$-aIlkyl, $C_1$–$C_6$-alkoxy, methoxymethyl, methoxymethoxy, amino, or $C_1$–$C_3$-alkyl-amino, except not more than one CHO, COOH, or COO—$C_1$–$C_3$-alkyl group may be present.

The term "substituted heteroaryl $C_1$–$C_6$alkyl" as used herein refers to a $C_1$–$C_6$alkyl group as defined herein substituted by replacement of one of the hydrogen atoms thereon with a substituted-heteroaryl moiety, as defined above.

Examples of compounds falling within the scope of the present invention precede the appended claims. If one specific enantiomer is shown or described, the other enantiomer may readily be made from the appropriate chiral precursor or can be resolved from a racemic mixture.

In a preferred embodiment of the present invention, there are provided compounds of formula (II)

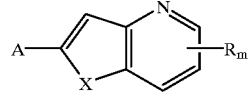

II wherein A is selected from the group consisting of

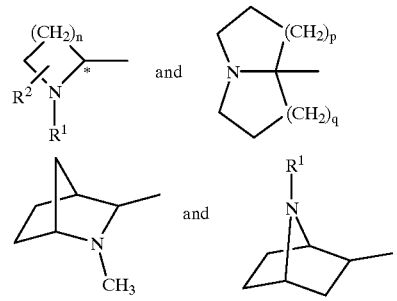

and the other variables as recited above for X and $R_m$.

In a particularly preferred embodiment of the present invention there is provided a compound of formula (II) above wherein A is selected from

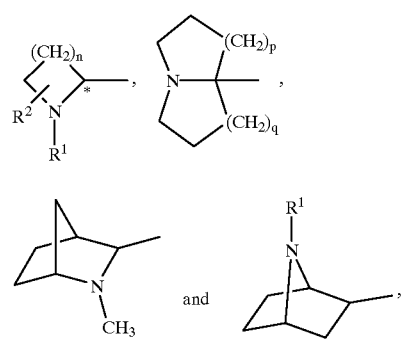

wherein R is H, Br, Cl, $C_1$–$C_4$-alkyl, phenyl or vinyl pyridyl and $R^2$ is H and $R^1$ is as specified above.

Further included within the scope of the present invention are pharmaceutical compositions comprising one or more of the compounds of formula (I) prepared and formulated in combination with one or more non-toxic pharmaceutically acceptable carriers in the manner described below.

Compositions suitable for parenteral injection may comprise pharmaceutically acceptable sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

If desired, and for more effective distribution, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar, as well as high molecular weight polyethylene glycols, and the like.

Solid dosage forms such as tablets, dragees, capsules, pills and granules may be prepared with coatings and shells, such as enteric coatings and others well known in this art. They may contain pacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol. 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical or transdermal administration of a compound of this invention further include ointments, pastes, creams, lotions, gels, powders, solutions, sprays, inhalants or transderrnal patches. Transdermal administration via a transdermal patch is a particularly effective and preferred dosage form of the present invention. The active component is admixed under sterile conditions with a pharmaceutically acceptable carrier and any needed preservative, buffers or propellants as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulations, eye ointments, powders and solutions are also contemplated as being within the scope of this invention.

The present compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the phospholipids and the phosphatidylcholines (lecithins), both natural and synthetic. Methods to form liposomes are known in the art. See, for example, Prescott, Ed., *Methods in Cell Biology*, Volume XIV, Academic Press, New York, N.Y., (1976), p 33 et seq.

In order to reduce unwanted peripherally mediated side-effects, it is advantageous, but not essential, to incorporate into the composition a peripherally acting anti-cholinergic such as N-methylscopolamine, N-methylatropine, propantheline, methantheline, or glycopyrrolate.

The compounds of the present invention may be synthesized as shown in reaction schemes 1–23 presented below using the reactions and techniques described in this section. The reactions are performed in a solvent appropriate to the reagents and materials employed are suitable for the transformation being effected. It is understood by those skilled in the art of organic synthesis that the functionality present on the heterocyclic ring and other portions of the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of nitrogen-protecting groups is well known in the art for protecting amino groups against undesirable reactions during a synthetic procedure and many such protecting groups are known, cf, for example, T. H. Greene and P. G. M. Wuts, *Protective Groups in Organic Synthesis*, 2nd edition, John Wiley & Sons, New York (1991).

compounds (5), i.e., compounds of formula (I) wherein $R^1$ is $C_1$–$C_3$-alkyl by reaction with the appropriate aldehyde under reducing conditions, for example, in the presence of $H_2$ and a catalyst such as Pd/C or in the presence of $NaBH_3CN$. The process of Scheme 1 is equally applicable to compounds of the series wherein n is 1 or 3, to give compounds analogous to compounds (4) and (5), i.e., compounds of formula (I) wherein A is (a) and n is 1 or 3.

Alternately, for compounds of Formula (I) wherein X is S, compounds are prepared by appropriate modifications of the above schemes for X=O. The appropriate precursor o-halo-hydroxyheterocycles are converted to the corresponding o-halo-mercaptoheterocycles by reaction with a diakylthiocarbamyl chloride, for example diethyl thiocarbamyl chloride, followed by heating to effect rearrangement to the thiocarbamate, followed by hydrolysis (Kwart and Evans, *J. Org. Chem.*, 31: 410, 1966; Newman and Karnes, *Org. Syn.*, 51:139, 1971). The resultant o-halo-mercaptoheterocycles are then allowed to react with the acetylene compound (1) under copper catalysis (optionally in the presence of palladium) at elevated temperature to afford thieno-fused heterocycles (cf. Malte and Castro, *J. Am. Chem. Soc.*, 89: 6770, 1967). Such reactions may be applied to give the desired starting materials wherein O is replaced by S for the compounds described in the following schemes, also.

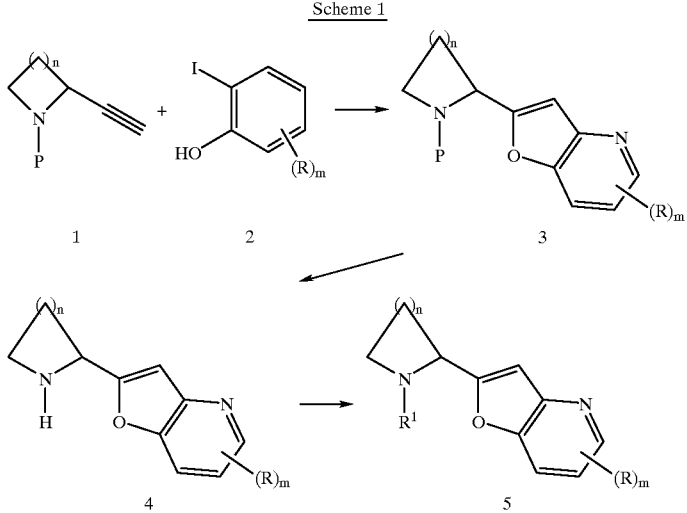

In accordance with Scheme 1 are prepared furo[3,2-b]pyridine compounds of Formula (I) wherein A is selected from group (a), R, $R^1$ and $R^2$ are as described above, X is O, $Y^1$ is N and $Y^2$ and $Y^3$ are CH. The process may be illustrated with the pyrrolidine series (n=2) thereof, in which an N-protected 2-acetylenylpyrrolidine starting material (1), wherein P is a N-protecting group, such as for example, BOC or CBZ, (which may be prepared from the corresponding imino-2-carboxylic acids according to known methods (Garvey, et al., *J. Med. Chem.*, 35: 1550–1557, 1992)) is reacted with an appropriate 2-iodo-3-hydroxypyridine (2), wherein R is as described above, in the presence of Pd, CuI and triethylamine at elevated temperature, to give the compound (3). (See Kundu, et al., *J. Chem. Soc. Chem. Comm.*, 1992: 41 for analogous preparation of benzofurans). The protecting group P may then be removed by standard methods to give compound (4), i.e., compounds of formula (I) wherein $R^1$ is H. Compound (4) may be converted into

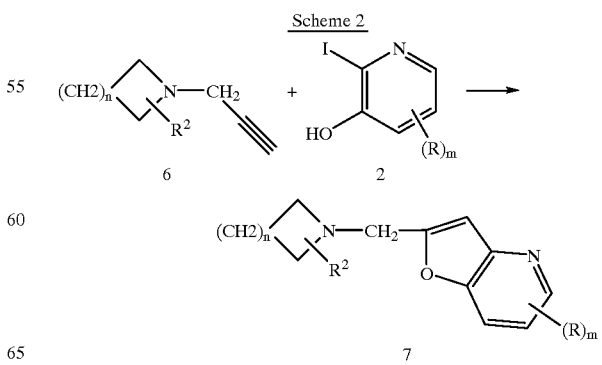

In accordance with Scheme 2 are prepared furo[3,2-b] pyridine compounds of Formula (I) wherein A is selected from group (b), $R^2$ is as described above, X is O, $Y^1$ is N and $Y^2$ and $Y^3$ are CH. The process may be illustrated with the pyrrolidine series (n=2) thereof, in which a 1-(3-propynyl) pyrrolidine starting material (6) (which may be prepared by reaction of the appropriately substituted pyrrolidine with 3-bromopropyne under basic conditions; see, for example, Biehl and DiPierro, *J. Am. Chem. Soc.*, 80:4609–4614, 1958). The compound (6) is reacted with an appropriate 2-iodo-3-pyridinol (2), wherein R is as described above, in the presence of Pd, CuI and triethylamine at elevated temperature, to give the compound (7). The process of Scheme 2 is equally applicable to compounds of the series wherein n is 1 or 3, to give compounds analogous to compound (7), i.e., compounds of formula (I) wherein A is (b) and n is 1 or 3.

The 2-iodo-3-pyridinols of Schemes 1 and 2 may be prepared by direct selective iodination of the corresponding pyridinols (e.g., Koch and Schnatterer, *Synthesis*, 1990:497). Alternately, 3-pyridinols with substituents in the 4-position can be prepared by selective lithiation of 3-pyridinol, O-protected with an ortho-directing moiety, e.g. methoxymethyl, diethylcarbamoyl, and the like (see Beak and Snieckus, *Acc. Chem. Res.*, 15:306–312, 1982). Alternately, 3-hydroxypyridines with substituents in other required positions can be prepared from the corresponding 3-aminopyridines under diazotizing conditions. Where appropriate, the 3-aminopyridines can be obtained by reduction of the corresponding 3-nitropyridine or by rearrangement of the 3-carboxylic acid or 3-carboxamide using the Hoffman, Curtius, or Schmidt rearrangements which are well-known in the art. In addition, 3-hydroxypyridines can be obtained by oxidation of an appropriate 3-lithio or magnesiopyridine with molecular oxygen, oxaziridines, or peroxides (see, for example, Taddei and Ricci, *Syn. Comm.*, 1986:633–635), or alternately peroxide oxidation of a pyridyl-3-dialkylborate, which can be obtained by reaction of a trialkyl borate with the appropriate 3-lithio- or magnesiopyridine (cf. Lawesson and Yang, *J. Am. Chem. Soc.*, 81:4320, 1959, and/or Hawthorne, *J. Org. Chem.*, 22:1001, 1957).

In an alternate procedure, the reactions of Scheme 2 may be performed with the analogous mercaptopyridine, prepared as described for Scheme 1 above, to give the thieno[3,2-b]pyrimidine compounds of Formula (I), wherein X is a S atom.

Scheme 3

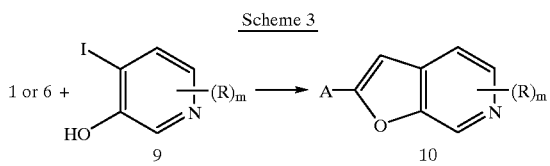

In accordance with Scheme 3 are prepared furo[2,3-c] pyridine compounds of Formula (I) wherein A is selected from (a) or (b) above, R, $R^1$ and $R^2$ are as described above, X is O, $Y^1$ is CH, $Y^2$ is N and $Y^3$ is CH. The acetylene-substituted starting material (1) or (6) is reacted with an appropriate 4-iodo-3-hydroxypyridine (9), wherein R is as described above, in the presence of Pd, CuI and triethylamine at elevated temperature, to give the compound (10). The requisite 4-iodo-3-hydroxypyridines are generally available using the techniques mentioned above together with selective 4-iodination of 3-hydroxypyridines (cf. Winkle and Ronald, *J. Org. Chem.*, 47:2101, 1982). In a further alternate procedure, the reactions of Scheme 3 may be performed with the analogous mercaptopyridine, prepared as described for Scheme 1 above, to give the thieno[2,3-c]pyrimidine compounds of Formula (I), wherein X is a S atom.

Scheme 4

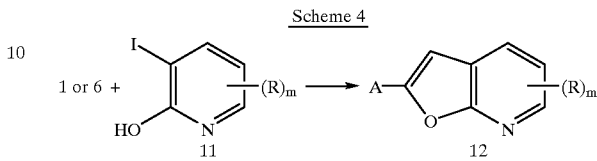

In accordance with Scheme 4 are prepared furo[2,3-b] pyridine compounds of Formula (I) wherein A is selected from (a) or (b) above, R, $R^1$ and $R^2$ are as described above, X is O, $Y^1$ and $Y^2$ are CH and $Y^3$ is N. The acetylene-substituted starting material (1) or (6) is reacted with an appropriate 3-iodo-2-hydroxypyridine (11), wherein R is as described above, in the presence of Pd, CuI and triethylamine at elevated temperature, to give the compound (12). The requisite 3-iodo-2-hydroxypyridines are generally available using the techniques mentioned above for synthesis of selectively substituted 3-hydroxypyridines. For example, the requisite 3-iodo-2-hydroxypyridines can be obtained by ortho iodination of the appropriate 2-hydroxypyridine. In a further alternate procedure, the reactions of Scheme 4 may be performed with the analogous mercaptopyridine, prepared as described for Scheme 1 above, to give the thieno[2,3-b]pyrimidine compounds of Formula (I), wherein X is a S atom.

Scheme 5

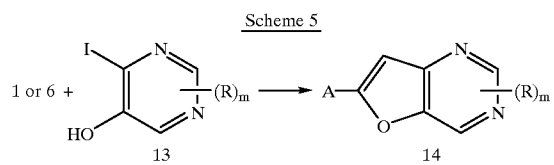

In accordance with Scheme 5 are prepared furo[3,2-d] pyrimidine compounds of Formula (I) wherein A is selected from (a) or (b) above, R, $R^1$ and $R^2$ are as described above, X is O, $Y^1$ is N, $Y^2$ is N and $Y^3$ is CH. The acetylene-substituted starting material (1) or (6) is reacted with an appropriate 4-iodo-5-hydroxypyrimidine (13), wherein R is as described above, in the presence of Pd, CuI and triethylamine at elevated temperature, to give the compound (14). The requisite 4-iodo-5-hydroxypyrimnidine compounds are generally available using the techniques mentioned above for synthesis of selectively substituted 3-hydroxypyridines. For example, the requisite 4-iodo-5-hydroxypyrimidine can be obtained by ortho iodination of the appropriate 5-hydroxypyrimidine. In a further alternate procedure, the reactions of Scheme 5 may be performed with the analogous mercaptopyridine, prepared as described for Scheme 1 above, to give the thieno[3,2-d]pyrimidine compounds of Formula (I), wherein X is a S atom.

Scheme 5a

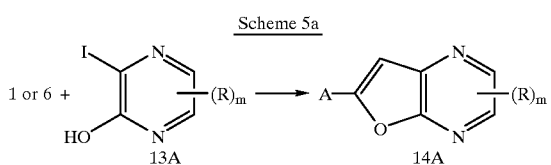

In accordance with Scheme 5A are prepared furo[2,3-b] pyrimidine compounds of Formula (I) wherein A is selected from (a) or (b) above, R, $R^1$ and $R^2$ are as described above, X is O, $Y^1$ is N, $Y^2$ is N and $Y^3$ is CH. The acetylene-substituted starting material (1) or (6) is reacted with an appropriate 3-iodo-2-hydroxypyrimidine (13A), wherein R is as described above, in the presence of Pd, CuI and triethylamine at elevated temperature, to give the compound (14A). The requisite 3-iodo-2-hydroxypyrimidine compounds are generally available using the techniques mentioned above for synthesis of selectively substituted 2-hydroxypyridines. For example, the requisite 3-iodo-2-hydroxypyrimidine can be obtained by ortho iodination of the appropriate 2-hydroxypyrimidine. In a further alternate procedure, the reactions of Scheme 5A may be performed with the analogous mercaptopyridine, prepared as described for Scheme 1 above, to give the thieno[2,3-b]pyrimidine compounds of Formula (I), wherein X is a S atom.

Scheme 6

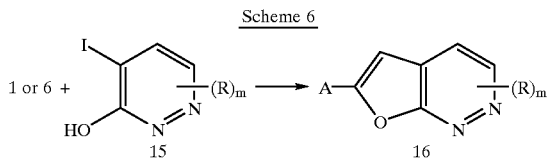

In accordance with Scheme 6 are prepared furo[2,3-c] pyridazine compounds of Formula (I) wherein A is selected from (a) or (b) above, R, $R^1$ and $R^2$ are as described above, X is O, $Y^1$ is CH, and $Y^2$ and $Y^3$ are N. The acetylene-substituted starting material (1) or (6) is reacted with an appropriate 4-iodo-3-hydroxypyridazine (15), wherein R is as described above, in the presence of Pd, CuI and triethylamine at elevated temperature, to give the compound (16). The requisite 4-iodo-3-hydroxypyridazine compounds are generally available using the techniques mentioned above for synthesis of selectively substituted 3-hydroxypyridines. For example, the requisite 4-iodo-3-hydroxypyridazine can be obtained by ortho Iodination of the appropriate 5-hydroxypyridazine. In a further alternate procedure, the reactions of Scheme 6 may be performed with the analogous mercaptopyridine, prepared as described for Scheme 1 above, to give the thieno[2,3-c]pyridazine compounds of Formula (I), wherein X is a S atom.

Scheme 7

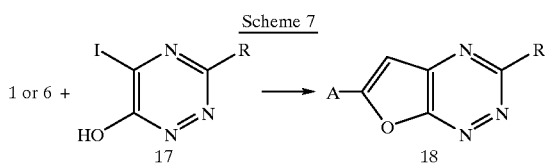

In accordance with Scheme 7 are prepared furo[3,2-e] triazine compounds of Formula (I) wherein A is selected from (a) or (b) above, R, $R^1$ and $R^2$ are as described above, X is O, $Y^1$ is CH, $Y^2$ is N and $Y^3$ is N. The acetylene-substituted starting material (1) or (6) is reacted with an appropriate 5-iodo-6-hydroxytriazine (17), wherein R is as described above, in the presence of Pd, CuI and triethylamine at elevated temperature, to give the compound (18). The requisite 5-iodo-6-hydroxytriazine compounds are generally available using the techniques mentioned above for synthesis of selectively substituted 3-hydroxypyridines. For example, the requisite 5-iodo-6-hydroxytriazine can be obtained by ortho iodination of the appropriate 5-hydroxytriazine.

Alternately, this reaction may be performed with the analogous mercaptopyrimidine, prepared as described for Scheme 1 above, to give the thieno[3,2-e]triazine compounds of Formula (I), wherein X is a S atom.

Scheme 8

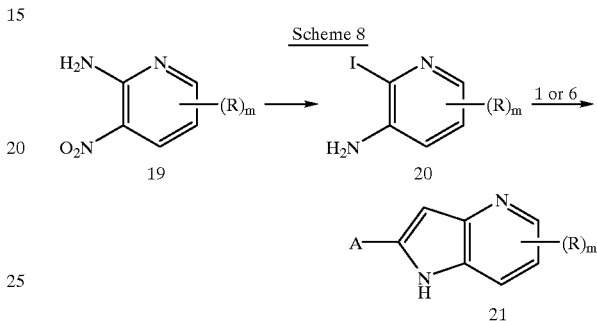

In accordance with Scheme 8 are prepared pyrrolo[3,2-b]pyridine compounds of Formula (D) wherein A is selected from (a) or (b) above, R, $R^1$ and $R^2$ are as described above, X is NH, $Y^1$ is N and $Y^2$ and $Y^3$ are CH. A starting material amino-nitro pyridine (19) is reacted with $NaNO_2$ and HI to replace the amino group with an iodo group, then with iron and acetic acid to reduce the nitro group to an amino group and give the compound (20). Compound 20 is then reacted with compound 1 or 6 in the presence of Pd, CuI and triethylamine at elevated temperature, as described above, to give the compound (21).

Scheme 9

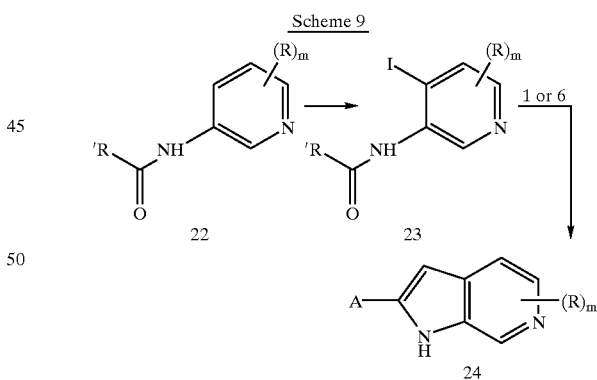

In accordance with Scheme 9 are prepared pyrrolo[2,3-c]pyridine compounds of Formula (I) wherein A is selected from (a) or (b) above, R, $R^1$ and $R^2$ are as described above, X is NH, $Y^1$ and $Y^3$ are CH and $Y^2$ is N. A protected aminopyridine compound starting material (22) is reacted with a strong base, such as t-butyllithium, and free iodine to give the iodinated compound (23). Compound (23) is then reacted with compound (1) or (6) in the presence of Pd, CuI and triethylarime at elevated temperature, as described above, followed by N-deprotection under standard conditions, to give the compound (24).

Scheme 10

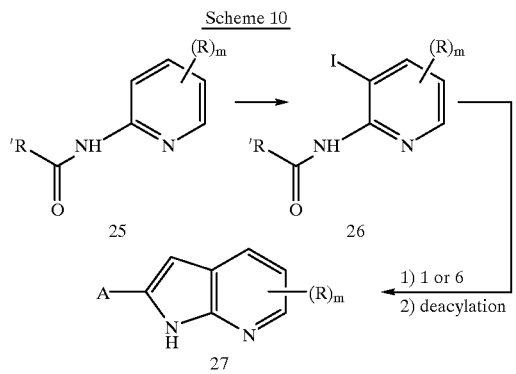

In accordance with Scheme 10 are prepared pyrrolo[2,3-b]pyridine compounds of Formula (I) wherein A is selected from (a) or (b) above, R, $R^1$ and $R^2$ are as described above, X is NH, $Y^1$ and $Y^2$ are CH and $Y^3$ is N. A protected aminopyridine compound starting material (25) is reacted with a strong base, such as t-butyllithium, and free iodine to give the iodinated compound (26). Compound (26) is then reacted with compound (1) or (6) in the presence of Pd, CuI and triethylamine at elevated temperature, as described above, then deacylated by standard methods to give the compound (27).

Scheme 11

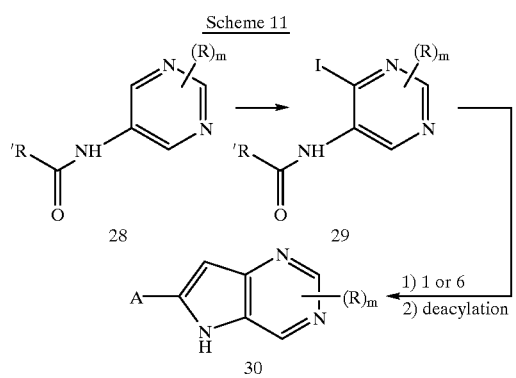

In accordance with Scheme 11 are prepared pyrrolo[3,2-d]pyrimidine compounds of Formula (I) wherein A is selected from (a) or (b) above, R, $R^1$ and $R^2$ are as described above, X is NH, $Y^1$ and $Y^2$ are N, and $Y^3$ is CH. A protected aminopyrimidine compound starting material (28) is reacted with a strong base, such as t-butyllithium, and free iodine to give the iodinated compound (29). Compound (29) is then reacted with compound (1) or (6) in the presence of Pd, CuI and triethylainine at elevated temperature, as described above, then deacylated by standard methods to give the compound (30).

Scheme 12

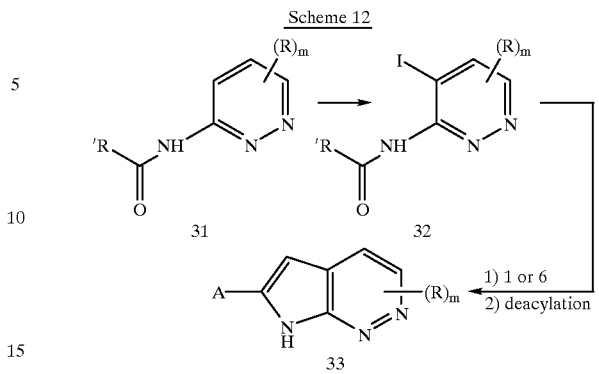

In accordance with Scheme 12 are prepared pyrrolo[2,3-c]pyridazine compounds of Formula (I) wherein A is selected from (a) or (b) above, R, $R^1$ and $R^2$ are as described above, X is NH, $Y^1$ is CH, and $Y^2$ and $Y^3$ are N. A protected aminopyridazine compound starting material (31) is reacted with a strong base, such as t-butyllithium, and free iodine to give the iodinated compound (32). Compound (32) is then reacted with compound (1) or (6) in the presence of Pd, CuI and triethylamine at elevated temperature, as described above, then deacylated by standard methods to give the compound (33).

Scheme 13

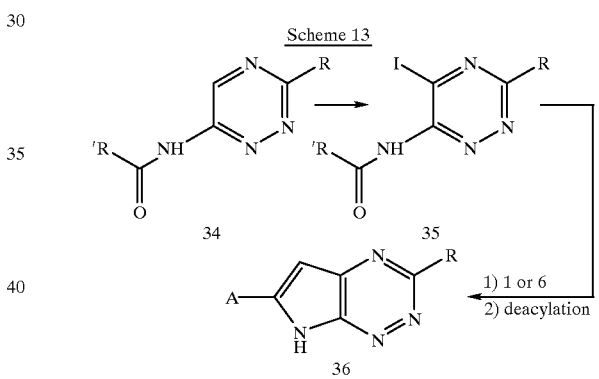

In accordance with Scheme 13 are prepared pyrrolo[3,2-e]triazine compounds of Formula (I) wherein A is selected from (a) or (b) above, R, $R^1$ and $R^2$ are as described above, X is NH, $Y^1$ is CH, and $Y^2$ and $Y^3$ are N. A protected aminotriazine compound starting material (34) is reacted with a strong base, such as t-butyllithium, and free iodine to give the iodinated compound (35). Compound (35) is then reacted with compound (1) or (6) in the presence of Pd, CuI and triethylamine at elevated temperature, as described above, then deacylated by standard methods to give the compound (36).

Scheme 14

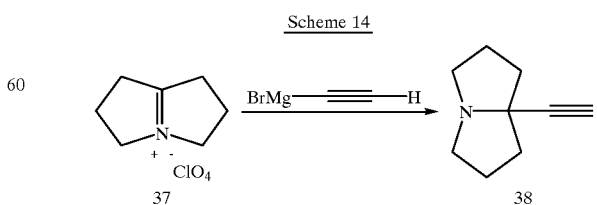

In accordance with Scheme 14 is prepared the 7a-ethynyl-1H-hexahydropyrrolizine starting material for compounds of Formula (I) wherein A is selected from option (c). The starting material pyrrolizidinium compound (prepared according to the procedure of Miyano et al., *Synthesis*, 1978:701–2) is reacted with the ethynyl magnesium bromide under appropriate Grignard conditions to give the compound (38). Compound 38 may be substituted for compounds (1) or (6) in any of Schemes 1–13 above to give the desired compound of Formula (I).

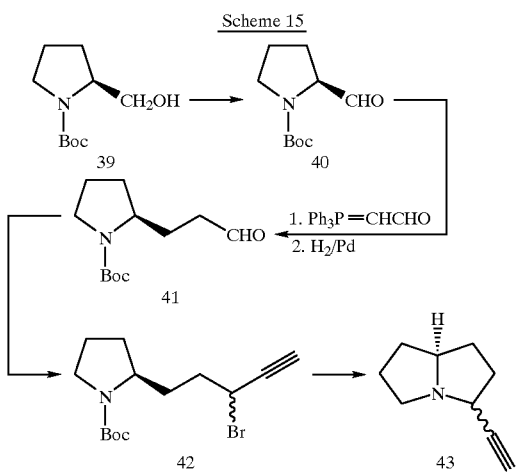

In accordance with Scheme 15 is prepared the 3-ethynyl-1H-hexahydropyrrolizine starting material (43) for compounds of Formula (I) wherein A is selected from option (d). The protected prolinol (39) is converted to the aldehyde compound (40) by reaction with triethylamine and pyridine-sulfur trioxide complex in DMSO. Compound (40) is reacted with (triphenylphosporanylidene)acetaldehyde, followed by reduction of the intermediate with $H_2$ over a Pd/C catalyst to give the extended aldehyde compound (41). Compound (41) is subsequently reacted with, for example, ethynyl magnesium bromide and the intermediate is reacted with triphenylphosphine dibromide to give compound (42). Compound 42 is treated with HCl in a polar organic solvent, such as ethanol, for example to give the 3-substituted pyrrolizidine compound (43). Compound (43) may be substituted for compounds (1) or (6) in any of Schemes 1–13 above to give the desired compound of Formula (I).

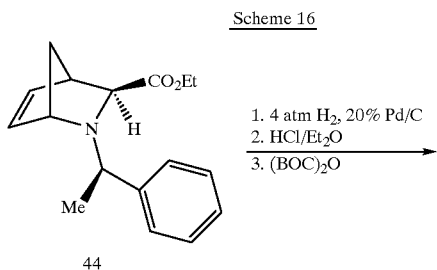

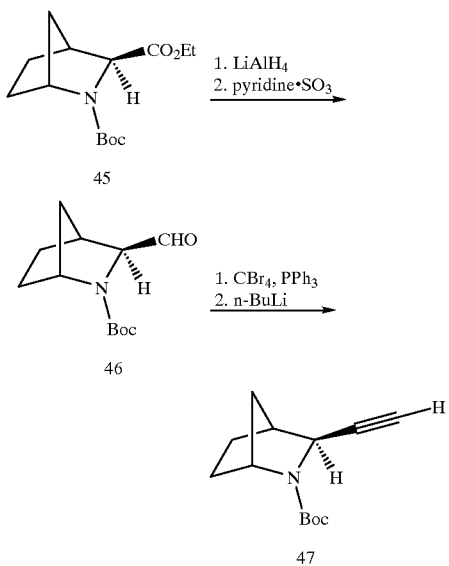

In accordance with Scheme 16 is prepared the ethynyl substituted 2-azabicyclo[2.2.1]heptane starting material for compounds of Formula (I) wherein A is selected from option (e). Compound (44) (prepared according to the procedure of Stella et al., *Tetrahedron Lett.*, 31:2603 (1990)) is deprotected by hydrogenolysis over Pd/C, then reprotected by treatment with di-t-butyldicarbonate to give the BOC-protected compound (45). Compound (45) is reduced with $LiAlH_4$ to an intermediate alcohol, which is then oxidized to obtain the aldehyde (46). Compound (46) is treated with $PPh_3$ and $CBr_4$ to give an intermediate dibromoalkene (not shown), which is then converted to the alkyne (47) by treatment with an alkyllithium compound. Compound (47) may be substituted for compounds (1) or (6) in any of Schemes 1–13 above to give the desired compound of Formula (I).

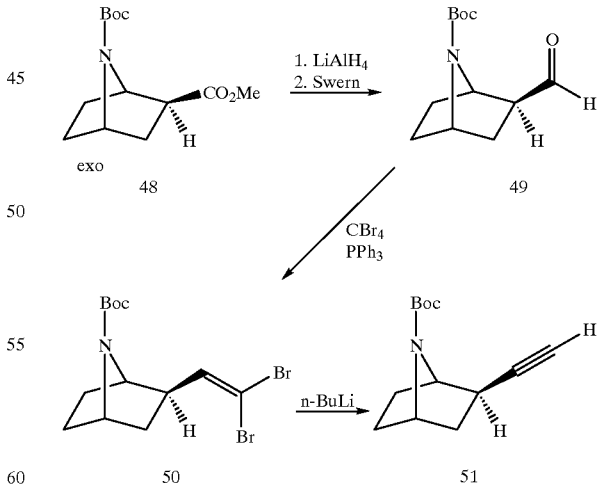

In accordance with Scheme 17 is prepared the ethynyl substituted 7-azabicyclo[2.2.1]heptane starting material for compounds of Formula (I) wherein A is selected from option (f). Compound (48) (prepared according to the procedure of Hernandez et al., *J. Org. Chem.*, 60:2683–2691 (1995)) is reduced with $LiAlH_4$ to an intermediate alcohol, which is then oxidized under Swern (DMSO, oxalyl chloride, $NEt_3$) or similar conditions to obtain the aldehyde (49). Compound (49) is treated with $PPh_3$ and $CBr_4$ to give the dibromoalkene (50), which is then converted to the alkyne (51) by treatment with an alkyllithium compound. Compound (51) may be substituted for compounds (1) or (6) in any of Schemes 1–13 above to give the desired compound of Formula (I).

It should be noted that compounds of Formula (I) wherein R is $C_1$–$C_4$-alkyl, Br, Cl, F, $CF_3$ or $CCl_3$ may be conveniently prepared by starting with the appropriately substituted compounds 2, 9, 11, 13, 13A, 15, 17, 20, 23, 26, 29, 32 or 35, which, if necessary, may be prepared by common techniques from the unsubstituted pyridine, pyrimidine or pyrazine starting materials or other commercially available derivatives thereof. Preparation of additional iodohydroxyheterocycles may be carried out by selective electrophilic aromatic substitution reactions upon the corresponding hydroxyheterocycles. In the above selective electrophilic substitution reactions, occasionally it may be necessary or desirable to achieve the desired position of substitution by blocking a more readily substituted position with a blocking and/or directing group, e.g. chloro or nitro, which can subsequently (either prior or subsequent to cycloaddition to acetylenes, e.g. 1, 6, 38, 43, 47 and 57) be removed by, respectively, reduction or a reduction/diazotization/reduction sequence. Alternately, a bromo- or chloro-substituent on an intermediate substituted pyridine or a fully assembled furopyridine or related heterocycle which has been constructed by way of the methods described above can be converted to other substituents. For example, by treating a compound of Formula (I) wherein R is Br with $NH_3$, optionally with catalysis by copper salts, under heat and pressure, compounds of Formula (I) wherein R is $NH_2$ may be prepared. Further treatment of compounds of Formula (I) wherein R is $NH_2$ with $NaNO_2$ and CuCN allows the preparation of compounds of Formula (I) wherein R is CN. As a further example, amino may be oxidized with $H_2SO_4$ and $H_2O_2$ to nitro, or carboxamide may be dehydrated to cyano. Cyano groups may be treated with the appropriate alcohol in the presence of a strong acid to prepare compounds of Formula (I) wherein R is COO—$C_1$–$C_4$-alkyl. Further hydrolysis of these esters with mild base gives the compounds of Formula (I) wherein R is COOH. Or compounds of Formula (I) wherein R is $NH_2$ may be N-acylated by the appropriate $C_1$–$C_4$-acyl chloride (or acyl halides selected from $C_1$–$C_8$-acyl halide, substituted $C_1C_8$-acyl halide, phenyl acyl halide, substituted phenyl-acyl-halide, heteroaryl-acyl halide, substituted heteroaryl-acyl-halide, phenyl-$C_1$–$C_6$-acyl halide, substituted phenyl-$C_1$–$C_6$-acyl halide, heteroaryl-acyl halide, substituted heteroaryl-acyl halide or (—O—$C_1$–$C_6$alkyl)acyl halide to give compounds of Formula (I) wherein R is NH—CO—$C_1$–$C_4$-alkyl or the acyl derivatives of the groups specified directly above. Further, compounds of Formula (I) wherein R is $NH_2$ may by alkylated or arylated to give the compounds of Formula (I) wherein R is $NR^1R^1$ or $NR^6R^7$. Also, bromo- or chloro-substituted compounds may be replaced with alkyl or alkenyl in reactions moderated by transition metals, e.g., palladium or nickel. Such alternate procedures as may be required are well known to those skilled in the art, and such alternate substituents are considered to be within the scope of the invention. Appropriate precursors to compounds 13, 13A, 15, 17, 29, 32 and 35 may also be prepared by ring-closure reactions of appropriately substituted acyclic compounds, such reactions being well known to those skilled in the art. In addition to the syntheses and synthetic schemes described above, the schemes and discussion presented below are directed to preparation of compounds of formula I wherein R, when substituted at the $Y^2$ position, may be selected from:

$NR^3R^4$, wherein $R^3$ is H or $C_1$–$C_3$ alkyl and $R^4$ is hydrogen, $C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;

$C(O)$—$R^5$, where $R^5$ is hydrogen, $C_1$–$C_8$-alkyl, substituted-$C_1$–$C_8$-alkyl, phenyl, substituted-phenyl, naphthyl, substituted naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, substituted-heteroaryl-$C_1$–$C_6$-alkyl-, and O—$C_1$–$C_6$-alkyl-, N—$R^6R^7$, wherein $R^6$ is selected from the group consisting of H and $C_1$–$C_3$-alkyl-, and $R^7$ is selected from the group consisting of H, $C_1$–$C_3$-alkyl-, phenyl and substituted-phenyl;

$OR^8$, wherein $R^8$ is $C_1$–$C_8$-alkyl, phenyl, substituted-phenyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, $CONR^3R^4$;

phenyl;

naphthyl;

substituted-phenyl;

substituted-naphthyl;

biphenyl;

substituted-biphenyl;

heteroaryl;

substituted-heteroaryl;

phenyl-$C_1$–$C_6$-alkyl-;

substituted-phenyl-$C_1$–$C_6$-alkyl-;

heteroaryl-$C_1$–$C_6$-alkyl-; and substituted-heteroaryl-$C_1$–$C_6$-alkyl-;

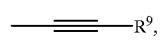

wherein $R^9$ is selected from the group consisting of hydrogen, $C_1$–$C_8$-alkyl, substituted-$C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroryl-$C_1$–$C_6$-alkyl-;

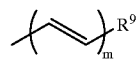

wherein m is 1 or 2, and $R^9$ is as defined above;

—$CH_2$—NH—CO—$R^5$, wherein $R^5$ is as defined above; and

—$CH_2$—$CH_2$—CO—O—$C_1$–$C_6$-alkyl.

In addition to the groups or variables recited for a compound of formula I in the preceding section with respect to A, $R^1$, $R^2$ and R, in a compound of formula I, $R^1$ may additionally be selected from allyl; $R^2$ for n is 1, 2 or 3 is selected from all the variables previously specified as well as Br, Cl, F, OH, CN, —O—CO—$CH_3$ and —O-methanesulfonyl provided said specifically referred to $R^2$ groups are not alpha to the ring nitrogen atom in group A; R at any position is additionally selected from vinyl and hydroxy.

Treatment of compounds of formula (I) wherein R is Br with alkoxides, e.g. those derived from $C_1$–$C_6$ alcohols or benzyl alcohol, for example, at elevated temperature allows preparation of of compounds of Formula (I) wherein R is $C_1$–$C_6$ alkyl-O— or benzyl-O—. Removal of the benzyl group by catalytic hydrogenolysis or treatment with acid, for example, hydrogen bromide in acetic acid, provides compound of formula (I) wherein R is hydroxy. The hydroxy group can then be alkylated by appropriate halides or sulfonates to afford compounds or formula (I) wherein R is C1–C8 alkyl—O—, phenyl-C1–C6-alkyl—O—, substituted phenyl C1–C6-alkyl—O—, heteroaryl-C1–C6-alkyl—O—, substituted heteroaryl-$C_1$–$C_6$-alkyl—O—, or acylated by appropriate isocyanates or carbamoyl chlorides to afford compounds of Formula (I) wherein R is OC(O)—$NR_3R_4$. The precursor wherein R is hydroxy can alternately be prepared from the compound wherein R is amino by treatment with sodium nitrite followed by heating under acid conditions. It will apparent to those skilled in the art that some of the above transformations will be best carried out following protection of moieties elsewhere in the molecule that may be susceptible to the reaction conditions with a suitable protecting group, followed by removal of the protecting group when no longer needed by conditions well known in the art.

The compounds and processes of the present invention will be better understood in connection with the following synthetic schemes which illustrate the methods by which the compounds of the invention may be prepared. The groups n, $R^1$ are as defined above unless otherwise noted.

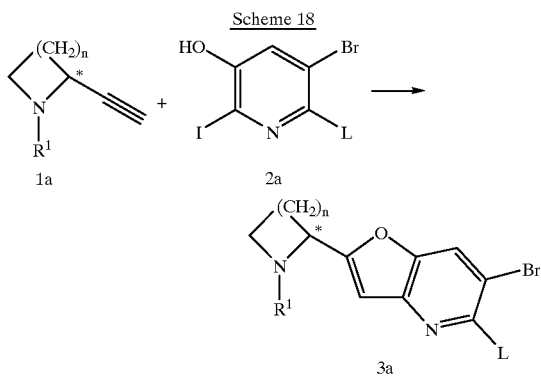

In accordance with Scheme 18 intermediate compounds are prepared by reaction of an acetylene compound (1a), wherein n is 1 to 3 and $R^1$ is allyl or $C_1$–$C_6$-alkyl or a protecting group such as t-BOC or CBZ, for example, with a 2-iodo-3-hydroxypyridine compound (2a), wherein L is H, F or Cl or R as defined herein for compounds of Formula (I) above, in the presence of Pd, CuI and triethylantine at the elevated temperature (See Kundu, et al., *J. Chem. Soc. Chem. Comm.*, 1992: 41 for analogous preparation of benzofurans) to form the 6-bromofuro[3,2-b]pyridyl compound (3a).

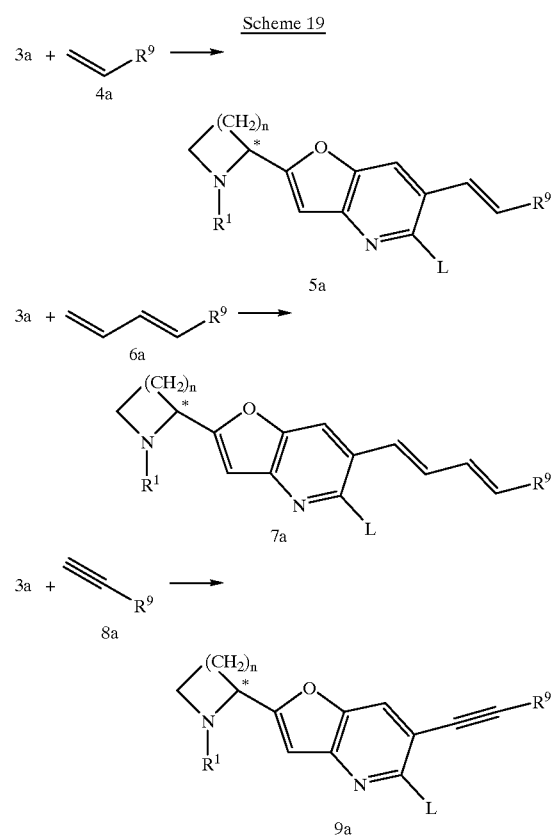

In accordance with Scheme 19 an intermediate compound (3a), wherein $R^1$ is allyl or $C_1$–$C_6$-alkyl or a protecting group such as t-BOC or CBZ, for example, is reacted with an unsaturated compound (4a), (6a) or (8a), to give compounds (5a), (7a) or (9a), respectively, which are specific or protected compounds of Formula (I), by treatment with a palladium (II) catalyst under weakly basic conditions at reflux temperature in an organic or aqueous solvent. Compound (4a) may be prepared by reacting a compound $R^9$—CHO, wherein $R^9$ is selected from the group consisting of hydrogen, $C_1$–$C_8$-alkyl, substituted-$C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-, with (phenyl)$_3$P=$CH_2$ in refluxing toluene. Of course, these compounds may further be treated with a reducing agent (e.g. hydrogen/catalyst) to form the saturated derivatives (R=heteroaryl$C_1$–$C_6$alkyl. Compound (6a) may be prepared by reacting a compound $R^9$—CHO, wherein $R^9$ is as described above, with $(Ph)_3P$=CH—CHO in refluxing toluene to give $R^9$—CH=CH—CHO, then reacting $R^9$—CH=CH—CHO with $(Ph)_3P$=$CH_2$ in refluxing toluene. Compound (8a) may be prepared by reacting $R^9$—CHO, wherein $R^9$ is as described above, with $CBr_4$ and $P(Ph)_3$ to give $R^9$—CH=$CBr_2$, then reacting $R^9$—CH=$CBr_2$ with 2 equivalents of n-butyllithium followed by treatment with $H^+$. In the cases wherein $R^1$ is a protecting group such as t-BOC or CBZ it must be removed under well-known standard conditions for removing those groups in order to give the desired compound of Formula (I). In some cases wherein $R^1$ is allyl or $C_1$–$C_6$-alkyl, it may be desirable to place this grouping in the compound after the protecting R¹ group has been removed. When R¹ is allyl, this may be accomplished by reacting the unprotected nitrogen atom with allyl chloride in the presence of a weak base such as triethylamine. When R¹ is $C_1$–$C_6$-alkyl, this may be accomplished by reacting the unprotected nitrogen atom with the appropriate aldehyde in the presence of NaCNBH₃, for example. L is chosen from the groups defined under R. Any of the above compounds may be further reduced to form a compound of the invention.

Scheme 20

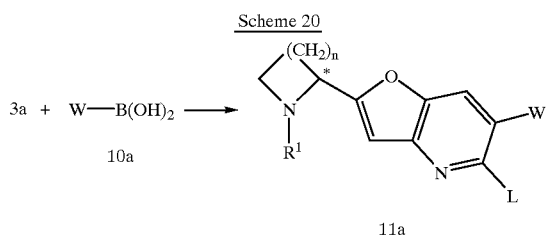

In accordance with Scheme 20 an intermediate compound (3a), wherein R¹ is allyl or $C_1$–$C_6$-alkyl or a protecting group such as t-BOC or CBZ, for example, is reacted with a suitable boronic acid compound (10a) wherein W is selected from the group consisting of: (a) phenyl; (b) naphthyl; (c) substituted-phenyl, as defined herein; (d) substituted-naphthyl, as defined herein; (e) biphenyl; (f) substituted-biphenyl, as defined herein; (g) heteroaryl, as defined herein; (h) substituted-heteroaryl, as defined herein; (i) phenyl-$C_1$–$C_6$-alkyl-, as defined herein; (j) substituted-phenyl-$C_1$–$C_6$-alkyl-, as defined herein; (k) heteroaryl-$C_1$–$C_6$-alkyl-, as defined herein; and (l) substituted-heteroaryl-$C_1$–$C_6$-alkyl-, as defined herein; for Formula (I) above, in the presence of Pd(O) under the conditions of the Suzuki reaction, for example in the presence of a weak base such as NaHCO₃ and in an aprotic solvent, such as toluene, benzene or methylene chloride at reflux temperatures to give a compound (11a), wherein R³ is as described above, to produce specific compounds of Formula (I). In an alternate method, compound (10a) may be replaced by a WMgX compound and reacted in the presence of Ni(dppp)₂Cl₂ to give compound (11). In the cases wherein R¹ is a protecting group such as t-BOC or CBZ it must be removed under well-known standard conditions for removing those groups in order to give the desired compound of Formula (I). In some cases wherein R¹ is allyl or $C_1$–$C_6$-alkyl, it may be desirable to place this grouping in the compound after the protecting R¹ group has been removed. When R¹ is allyl, this may be accomplished by reacting the unprotected nitrogen atom with allyl chloride in the presence of a weak base such as triethylamine. When R¹ is $C_1$–$C_6$-alkyl, this may be accomplished by reacting the unprotected nitrogen atom with the appropriate aldehyde in the presence of NaCNBH₃, for example. L is equal to R as defined above at the designated position.

Scheme 21

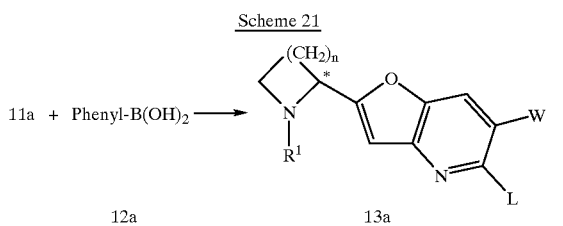

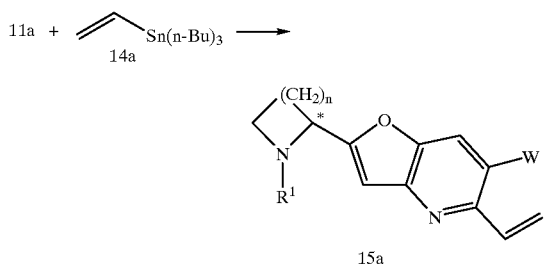

In accordance with Scheme 21 are prepared compounds of Formula (I) wherein L is vinyl, phenyl or substituted phenyl. Reaction of a starting material compound (11a) wherein L is chloro with phenylboronic acid (12a) in the presence of Pd(O) under the conditions of the Suzuki reaction, for example in the presence of a weak base such as NaHCO₃ and in an aprotic solvent, such as toluene, benzene or methylene chloride at reflux temperatures gives the compound 13a. Reaction of a starting material compound (11a) wherein L is chloro with vinyl-Sn(n-Bu)₃ (14a) in the presence of Pd(O) under Stille reaction conditions to give the compound (15a). In the cases wherein R¹ is a protecting group such as t-BOC or CBZ it must be removed under well-known standard conditions for removing those groups in order to give the desired compound of Formula (I). In some cases wherein R¹ is allyl or $C_1$–$C_6$-alkyl, it may be desirable to place this grouping in the compound after the protecting R¹ group has been removed. When R¹ is allyl, this may be accomplished by reacting the unprotected nitrogen atom with allyl chloride in the presence of a weak base such as triethylamine. When R¹ is $C_1$–$C_6$-alkyl, this may be accomplished by reacting the unprotected nitrogen atom with the appropriate aldehyde in the presence of NaCNBH₃, for example.

Scheme 22

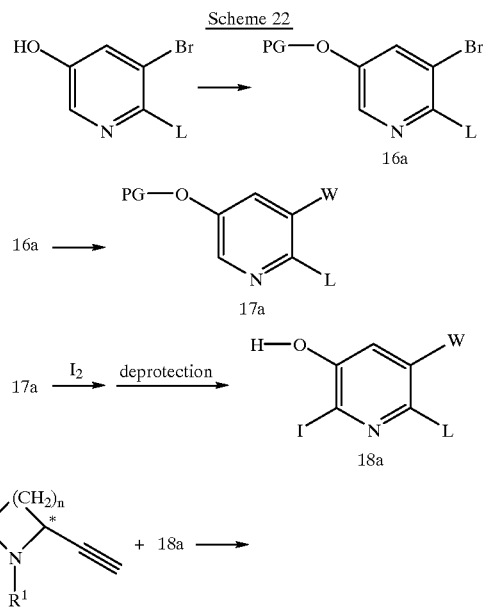

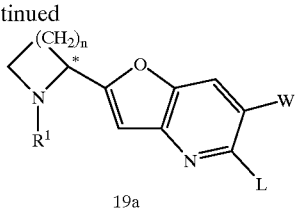

In Scheme 22 is shown an alternate process for preparing desired compounds of the invention. Whereas in Schemes 19 and 20, the heterocyclic and the pyridine moieties are first joined, and the W group is added according to Schemes 19 and 20, Scheme 22 allows for the placement of the W group before joining. Accordingly a hydroxypyridine compound is treated with the appropriate reagent, such as a trialkylsilyl or benzyl chloride, to protect the hydroxyl group with a protecting group PG, such as trialkylsilyl or benzyl, respectively, for example to give compound (16a). Compound (16a) may then be reacted with an appropriate reagent, as described in Schemes 19 and 20, to give the compound (17a) having the desired substitution at L and W. L is chosen from R as designated previously at that position on the ring and W is as defined previously. Subsequent iodination followed by deprotection by standard methods gives (18a), which is then coupled with compound (1) according to the method of Scheme 18 to give the desired compound of Formula (I).

amino compound. The intermediate amino compound may then be treated with a suitable acylating reagent, for example ethyl formate, an acyl chloride $R^5$—C(=O)Cl wherein $R^5$ is, for example, $C_1$–$C_8$-alkyl, substituted-$C_1$–$C_8$-alkyl, phenyl, substituted-phenyl, heteroaryl, substituted-heteroaryl, aryl-$C_1$–$C_6$-alkyl-, substituted-aryl-$C_1$–$C_6$-alkyl-, heteroaryl-$C_1$–$C_6$-alkyl-, or substituted-heteroaryl-$C_1$–$C_6$-alkyl-, a $C_1$–$C_6$-alkyl dicarbonate; or is treated with an appropriate carbamylating reagent, for example KOCN or an isocyanate $R^7$NCO wherein $R^7$ is selected from $C_1$–$C_3$alkyl, phenyl or substituted phenyl or Cl—CO—N—$R^6R^7$, for example, wherein $R^6$ may be $C_1$–$C_3$-alkyl-, and $R^7$ may be $C_1$–$C_3$-alkyl-, phenyl or substituted-phenyl.

In Vitro Determination of Neuronal Nicotinic Acetylcholine Receptor Binding Potencies For the purpose of identifying compounds as nicotinic acetylcholinergic agents which are capable of interacting with neuronal nicotinic acetylcholine receptors in the brain, a ligand-receptor binding assay was carried out as the initial screen. Compounds of the present invention were effective at interacting with neuronal nicotinic acetylcholine receptors as assayed for their ability to displace radioligand from neuronal nicotinic acetylcholine receptors labeled with [$^3$H]-cytisine ([$^3$H]-CYT).

A. Protocol For Determination of Nicotinic Acetylcholine Receptor Binding Potencies of Ligands Binding of [$^3$H]-CYT to nicotinic acetylcholine receptors was accomplished using crude synaptic membrane prepara-

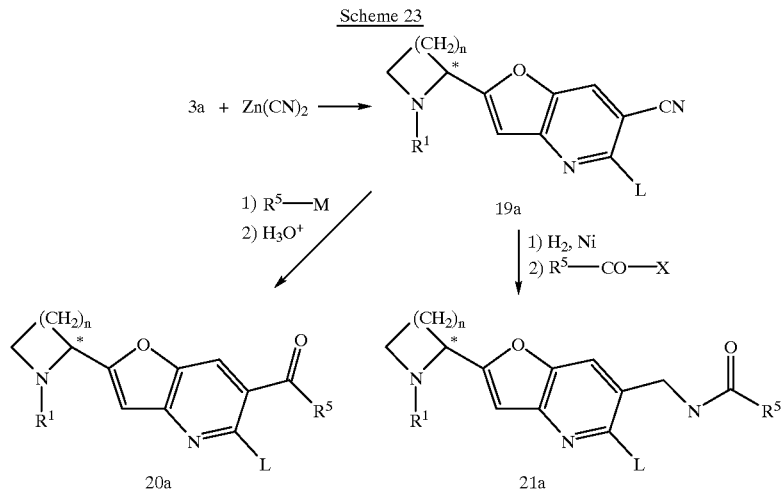

In accordance with Scheme 23 are prepared additional compounds of Formula (I). Compound (3a) is first reacted with $Zn(CN)_2$ and tetrakis(triphenylphosphine)palladium(0) under anhydrous conditions in DMF or a similar solvent at room temperature to 120° C. for 12–24 hours, to give the cyano intermediate compound (19a) with L selected from R as defined above. Compound (19a) may then be reacted with a reagent $R^5$—M, wherein $R^5$ is as described for Formula (I) above and M is lithium or a magnesium halide moiety, under the appropriate anhydrous conditions, with cooling if necessary, for 2–8 hours or until the reaction is complete to give, followed by treatment with aqueous acid to dissociate the metal complexes and give compound (20a). Alternately, the cyano group of compound (19a) may be reduced by treatment with 1 atm of $H_2$ in the presence of Raney nickel at room temperature for 1–8 hours to give an intermediate tions from whole rat brain (Pabreza et al., *Molecular Pharmacol.*, 1990, 39:9). Washed membranes were stored at −80° C. prior to use. Frozen aliquots were slowly thawed and resuspended in 20 volumes of buffer (containing: 120 mM NaCl, 5 mM KCl, 2 mM $MgCl_2$, 2 mM $CaCl_2$ and 50 mM Tris-Cl, pH 7.4 @4° C.). After centrifuging at 20,000×g for 15 minutes, the pellets were resuspended in 30 volumes of buffer. Homogenate (containing 125–150 μg protein) was added to triplicate tubes containing concentrations of test compound and [$^3$H]-CYT (1.25 nM) in a final volume of 500 μL. Samples were incubated for 60 minutes at 4° C., then rapidly filtered through Whatman GF/B filters presoaked in 0.5% polyethylimine using 3×4 mL of ice-cold buffer. The filters were counted in 4 mL of Ecolume® (ICN). Nonspecific binding was determined in the presence of 10 μM (−)-nicotine and values were expressed as a percentage of total binding. $IC_{50}$ values were determined with the RS-1 (BBN) nonlinear least squares curve-fitting program and $IC_{50}$ values were converted to Ki values using the Cheng and Prusoff correction (Ki=$IC_{50}$/(1+[ligand]/Kd of ligand). The results (shown in Table 1) suggest that the compounds of the present invention have high affinity for the neuronal nicotinic acetylcholine receptor.

The ability of the compounds of the invention to interact with nicotinic acetylcholine receptors and thereby to activate or inhibit synaptic transmission can be demonstrated in vitro using the following protocol.

B. Protocols for the Determination of Functional Effects of Nicotinic Acetylcholine Receptor Ligands on Synaptic Transmission Cells of the IMR-32 human neuroblastoma clonal cell line (ATCC, Rockville, Md.) were maintained in a log phase of growth according to established procedures (Lukas, R. J., *J. Pharmacol. Exp. Ther.*, 265: 294–302, 1993). Experimental cells were seeded at a density of 500,000 cells/mL into a 24-well tissue culture dish. Plated cells were allowed to proliferate for at least 48 hours before loading with 2 $\mu$Ci/mL of $^{86}Rb^+$ (35 Ci/mmol) overnight at 37° C. The $^{86}Rb^+$ efflux assays were performed according to previously published protocols (Lukas, 1993) except serum-free Dulbecco's Modified Eagle's Medium was used during the $^{86}Rb^+$ loading, rinsing, and agonist-induced efflux steps.

Cells of the K177 cell line, resulting from stable transfection of the human embryonic kidney (HEK) 293 cell line with the cDNA of the α4 and β2 nicotinic acetylcholine subunits (Gopalakrishnan, et al, *J. Pharmacol. Expt. Ther.* 1996, 276, 289–297), were maintained in a log phase of growth according to established procedures (Gopalakrishnan, et al., loc. cit.). The cells were plated onto poly-lysine coated 24-well Costar plates (Cambridge, Mass.) at a density of 250,000 cells/well. When confluent, the cells were loaded with $^{86}Rb^+$ and agonist-induced efflux was assessed as reported above for IMR-32 cells.

Maximal responses (reported as percent relative to the response elicited by 100 $\mu$M (S)-nicotine) are shown for selected compounds of the invention. The inhibition data (given for other selected compounds) reflect inhibition of the efflux elicited by 100 $\mu$M (S)-nicotine at the indicated concentration. The results (also shown in Table 1) suggest that selected compound of the present invention either activate or inhibit the initial ion flux aspects of synaptic transmission mediated by neuronal nicotinic acetylcholine receptors. This finding is in agreement with the results of others who have linked dopamine release, which is dependent upon the ion flux in synaptic transmission, to binding at nicotinic receptors (cf., for example, Lippiello and Caldwell, U.S. Pat. No. 5,242,935, issued Sept. 7, 1993; Caldwell and Lippielo, U.S. Pat. No. 5,248,690, issued Sept. 28, 1993; and Wonnacott et al., Prog. Brain Res; 79: 157–163 (1989)).

TABLE 1

Binding to Neuronal Nicotinic Acetylcholine Receptors and Activation or Inhibition of Neuronal Nicotinic Acetylcholine in K177 or IMR-32 Cells

| Ex. No. | [$^3$H]-Cyt Binding (nM) | K177 % max | K177 % Inhibition @ 10 $\mu$M | IMR-32 % max | IMR-32 % Inhibition @ 10 $\mu$M |
|---|---|---|---|---|---|
| 1 | 2.7 | 79 | | 7 | 16 @ (30 $\mu$M) |
| 2 | 76 | 0 | | | 24 |
| 3 | 4.1 | 34 | | 58 | |
| 4 | 17.5 | 63 | | | |
| 5 | 355 | | | | |
| 6 | 4.7 | 68 | | 14 | 4 |
| 7 | 878 | | | | |
| 8 | 27 | 3 | 45 | 0 | 9 |
| 9 | 250 | | | 83 | |
| 10 | 207 | | | | |
| 11 | 58 | | | | |
| 12 | 4.1 | 41 | | 11 | |
| 13 | 4440 | | | | |
| 14 | 181 | | | | |
| 15 | 0.45 | 9 | | 43 | |
| 16 | 5.8 | 109 | | 0 | 10 |
| 17 | 88 | | | | |
| 18 | 38 | | | | 55 @ (30 $\mu$M) |
| 19 | 3950 | | | | |
| 20 | 397 | | | | |
| 21 | 3300 | | | 0 | 50 @ (30 $\mu$M) |
| 22 | 113 | | | | |
| 23 | 0.62 | | | | |
| 24 | 2 | 14 | 60 | | |
| 25 | 103 | | | | |
| 26 | 0.66 | 6 | 53 | 7 | 38 |
| 27 | 27 | | | | |
| 28 | 4.8 | 20 | | | |
| 29 | 6.8 | 0 | 28 | 20 | 0 |
| 30 | 101 | | | | |
| 31 | 9.8 | 13 | 41 | 39 | |
| 32 | 54 | | | | |
| 33 | 200 | 0 | | 0 | 8 |
| 34 | 1710 | | | 18 | 2.8 |
| 35 | 1.1 | 61 | | | |
| 36 | 611 | | | | |
| 37 | 1760 | | | | |
| 38 | 0.33 | 0 | | 12 | 10 |
| 38 | 1.1 | 39 | | 4 | 25 |
| 40 | 32 | | | | |
| 41 | 81 | | | | |
| 42 | 4.7 | 29 | | 24 | |
| 43 | 453 | | | | |
| 44 | 5 | | | | |
| 45 | 205 | | | | |
| 46 | 468 | | | | |
| 47 | 38 | | | | |
| 48 | 1.3 | 0 | | 6 | 0 |
| 49 | 2.6 | | | 1 | 10 |
| 50 | 46 | | | | |
| 51 | 443 | | | | |
| 52 | 0.86 | 36 | | 69 | |

In addition to the data presented above which demonstrates that the compounds of the invention are effective binders to the nicotinic acetylcholine receptor and are functional ligands, the following table (Table 2) shows additional data for examples 53–59 and 134–136.

TABLE 2

Binding to Neuronal Nicotinic Acetylcholine Receptors and Activation of Neuronal Nicotinic Acetylcholine Receptors in IMR-32 Cells

| Ex. No | Binding (nM) | IMR-32 % max |
|---|---|---|
| 53 | 335 | |
| 54 | 104 | |
| 55 | 0.16 | 32 |
| 56 | 12.9 | |

TABLE 2-continued

Binding to Neuronal Nicotinic Acetylcholine Receptors and Activation of Neuronal Nicotinic Acetylcholine Receptors in IMR-32 Cells

| Ex. No | Binding (nM) | IMR-32 % max |
|---|---|---|
| 57 | 0.83 | 22 |
| 58 | 0.31 | |
| 59 | 672 | |
| 134 | 6.9 | |
| 135 | 3.2 | |
| 136 | 2.4 | |

As can be seen from Tables 1 and 2, compound 55 exhibited potent in vitro binding. The following examples will serve to further illustrate preparation of the novel compounds of the invention. They are not to be read as limiting the scope of the invention as it is defined by the appended claims.

Thin-layer chromatography (TLC) was performed on 0.25 mm E. Merck precoated silica gel plates (60 F-254). Flash chromatography was performed on 200–400 mesh silica gel (E. Merck), and column chromatography was performed on 70–230 mesh silica gel (E. Merck).

The following abbreviations are used: THF for tetrahydrofuran, DMF for N, N-dimethylformamide, $D_2O$ for deuterium oxide, $CDCl_3$ for deuterochloroform, DMSO-$d_6$ for deuterodimethylsulfoxide, BOC for tert-butyloxycarbonyl, CBZ for benzyloxycarbonyl, Bn for benzyl, Ms for methanesulfonyl, PAW for pyridine/acetic acid/water (20:6:11), DCC for dicyclohexylcarbodiimide, DIBALH for diisobutylaluminum hydride, DIEA for diisopropylethylarrine, DPPA for diphenylphosphororyl azide, DME for 1,2-dimethoxyethane, EDC for 1-(3-dimethyl-aninopropyl)-3-ethylcarbodiimide hydrochloride, EtOH for ethanol, $Et_2O$ for diethyl ether, IBCF for isobutyl chloroformate, HOAc for acetic acid, HOBT for 1-hydroxybenzotriazole, LAH for lithium aluminum hydride, MeOH for methanol, $NH_4OAc$ for ammonium acetate, dppp for 1,3-bis(diphenylphosphino)propane; NMM for N-methylmorpholine, TEA for triethylamine, THF for tetrahydrofuran.

EXAMPLE 1

Preparation of 2-(1-methyl-2-(S)-pyrrolidinyl)furo [3,2-b]pyridine dihydrochloride 1a. N-BOC-(S)-prolinal N-BOC-(S)-proline was reduced to N-BOC-(S)-prolinol by treatment with diborane as described by K. E. Rittle et al. (*J. Org. Chem.*, 47:3016 (1982)). N-t-butyloxycarbonyl-(S)-prolinol was then oxidized to N-t-butyloxycarbonyl-(S)-prolinal by treatment with DMSO and sulfur trioxide-pyridine complex as described by Y. Hamada and T. Shioiri (*Chem. Pharm. Bull*, 5:1921 (1982)).

1b. 2(S)-(2,2-Dibromoethenyl)-N-t-butyloxycarbonylpyrrolidine

At room temperature and under nitrogen, triphenylphosphine (13.0 g, 49.5 mmol), zinc dust (2.16 g, 33.0 mmol) and carbon tetrabromide (11.0 g, 33.0 mmol) were added to $CH_2Cl_2$ (80 mL). After stirring for 5 minutes, a solution of N-t-butyloxycarbonyl-(S)-prolinal (3.29 g, 16.5 mmol) in $CH_2Cl_2$ (25 mL) was added. The reaction was slightly exothermic. After stirring for 1 hour, the reaction mixture was diluted with EtOAc/hexane (1:1) and filtered through basic alumina. The filter cake was then washed with a mixture of $CH_2Cl_2$/EtOAc/hexane (1:1:1). The filtrate was concentrated in vacua, and the residue was taken up in EtOAc/hexane (1:1). The resulting precipitate was filtered, and the filtrate was taken up in EtOAc/hexane (1:1). The resulting precipitate was filtered, and the filtrate was (1:6.5 to 1:5) as the eluant. The resultant pure solid product was isolated in 91% yield (5.31 g): mp 65–66° C.; $[\alpha]_D^{\cong}$+20.1 (c 1.10, MeOH); $^1$H NMR (DMSO-$d_6$, 70° C., 300 MHz) δ 6.57 (d, J=8.1 Hz, 1H), 4.26 (ddd, J=7.9, 7.9, 4.9 Hz, 1H), 3.30 (m, 2H), 2.11 (m, 1H), 1.72–1.92 (m, 2H), 1.65 (m, 1H), 1.40 (s, 9H); MS m/e 354 (M+H)$^+$; Anal. Calcd for $C_{11}H_{17}Br_2NO_2$: C, 37.21; H, 4.83; N, 3.95. Found: C, 37.45; H, 4.85; N, 3.97.

1c. 1-BOC-2-(S)-ethynylpyrrolidine

A solution of the compound of step 1b above (27.1 g, 76.3 mmol) and THF (550 mL) was cooled to −75° C. Under a nitrogen atmosphere, a 2.5 M solution of n-butyllithium in hexane (62.6 mL, 156 mmol) was added dropwise over a 15 minute period. After stirring for 1 hour, saturated aqueous sodium bicarbonate was added dropwise to the reaction flask. The dry ice bath was removed and an additional portion of saturated aqueous sodium bicarbonate was added. The mixture was extracted with EtOAc (3×) and the combined organic phases dried over anhydrous sodium sulfate and concentrated in vacuo. The resulting residue was purified by flash chromatography on silica gel eluting with Et2O/hexane (1:6 to 1:5) to give 11.5 g (77% yield) of the title compound (1c) as an oil: $[\alpha]_D^{\cong}$−92.1 (c 2.20, MeC)H); $^1$H NMR (CDCl$_3$, 300 MHz) δ 4.45 (m, 1H), 3.53–3.24 (m, 2H), 2.25–1.85 (m, 5H), 1.48 (s, 9H); MS (CI) m/e 196 (M+H)$^+$.

1d. 2-(1-BOC-2-(S)-pyrrolidinyl)furo[3,2-b]pyridine

A 2.34 g (12 mmol) sample of the compound from step 1c above was dissolved in 15 mL of DMF, and (Ph$_3$P)$_2$PdCl$_2$ (0.6 mmol), CuI (0.74 mmol) and triethylamine (14.25 mmol) were added. The mixture was stirred at room temperature for 1 hour, then 3.14 g (14.4 mmol) of 2-iodo-3-hydroxypyridine (Lancaster Chem. Co.) was added. The reaction mixture was stirred at 60° C. for 16 hours. The solution was cooled, diluted with toluene, and the volatiles were removed under reduced pressure. The residue was dissolved in 1 N HCl, and this solution was extracted with ether. The acidic aqueous layer was adjusted to pH 10 with $K_2CO_3$, and this solution was extracted with $CH_2Cl_2$. The $CH_2Cl_2$ extract was washed with 20% Na,OH, dried over MgSO$_4$, and evaporated. The residue was chromatographed on silica gel, eluting with 100:0 to 95:5 CHCl$_3$:MeOH to give 980 mg of title compound: $^1$H NMR (CDCl$_3$, 300 MHz) δ 1.32 (s, 9H), 1.90–2.20 (m, 4H), 2.95–3.15 (m, 2H), 5.05 (m, 1H), 6.68 (s, 1H), 7.15 (br s, 1H), 7.67 (d, 1H, J=8 Hz), 8.48 (d, 1H, J=3 Hz); MS m/z: 289 (M+H)$^+$.

1e. 2-(1-methyl-2-(S)-pyyrrolidinyl)furo[3,2-b]pyridine dihydrochloride

A 147 mg sample of the compound from step 1d above was dissolved in 4 mL of HCHO and 2 mL of 88% formic acid and heated at reflux for 25 minutes. The solution was cooled, diluted with water, and adjusted to pH 10 with $K_2CO_3$. The mixture was extracted with $CH_2Cl_2$, and the extract dried and concentrated. The residue was purified by chromatography on silica gel, eluting with 100:0 to 90:10 CHCl$_3$:MeOH. The product was dissolved in ethanol, and a solution of HCl in $Et_2O$ was added dropwise. The resultant white precipitate was then collected by evaporation of solvent and triturated with three portions of $Et_2O$ to give the title compound (200 mg): $^1$H NMR (CDCl$_3$, 300 MHz) δ 2.35–2.37 (m, 2H), 2.58–2.67 (m, 3H), 3.00 (br s, 3H), 3.40 (br s, 1H), 3.90 (br s, 1H), 7.45 (s, 1H), 7.70 (dd, 1H, J=5, 8.5 Hz), 8.33 (d, 1H, J=8.5 Hz), 8.64 (dd, 1H, J=5, 1 Hz). MS m/z: 203 (M+H)$^+$; Anal. Calcd for $C_{12}H_{14}N_2O.2.0$ HCl.0.2 H₂O.0.1 EtOH: C, 51.99; H, 6.08; N, 9.94. Found: C, 51.59; H, 6.03; N, 9.68.

EXAMPLE 2

Preparation of 2-(2-(S)-pyrrolidinyl)furo[3,2-b]pyridine dihydrochloride

A 980 mg sample of 2-(1-BOC-2-(S)-pyrrolidinyl)furo[3,2-b]pyridine, from Example 1d above, was dissolved in a solution of TFA in $CH_2Cl_2$ at 0° C. and stirred under $N_2$ while warming to room temperature. The reaction mixture was diluted with 1 N HCl, and the aqueous layer was separated. The aqueous solution was adjusted to pH 10 with $K_2CO_3$, and the mixture was extracted with $CH_2Cl_2$. The solution was dried over $MgSO_4$ and concentrated. The residue was purified by chromatography on silica gel and treated with HCl in $Et_2O$ as described in Example 1e to obtain 280 mg of title compound: $^1H$ NMR ($CDCl_3$, 300 MHz) δ 2.17–2.52 (m, 3H), 2.65 (m, 1H), 3.57 (dt, 2H, J=1.5, 7.5 Hz), 5.15 (t, 1H, J=8 Hz), 7.44 (s, 1H), 7.84 (dd, 1H, J=6, 8.5 Hz), 8.5 (dt, 1H, J=1, 8.5 Hz), 8.70 (dd, 1H, J=1, 6 Hz). MS m/z: 189 (M+H)⁺, 206 (M+NH₄)⁺; Anal. Calcd for $C_{11}H_{12}N_2O.2.0$ HCl: C, 50.59; H, 5.40; N, 10.73. Found: C, 50.52; H, 5.26; N, 10.50.

EXAMPLE 3

Preparation of 2-(2-(R)-pyrrolidinyl)furo[3,2-b]pyridine dihydrochloride 3a. 1-BOC-2-(R)-ethynylpyrrolidine The title compound was prepared from N-BOC-(R)-proline according to the procedures of Examples 1a–c above. $[α]_D^≤$+113.0 (c 0.94, MeOH).

3b. 2-(1-BOC-2-(R)-pyrrolidinyl)furo[3,2-b]pyridine

A 3.14 g (14.4 mmol) sample of 2-iodo-3-hydroxypyridine (Lancaster Chem. Co.) was dissolved in 5 mL of DMF, and $(Ph_3P)_2PdCl_2$ (0.34 g, 0.50 mmol), CuI (0.371 g, 1.98 mmol) and triethylanine (1.80 mL, 13.2 mmol) were added. The mixture was stirred under $N_2$ at room temperature for 1 hour, then 2.15 g (11.0 mmol) of the compound from step 3a above, dissolved in 5 mL of DMF, was added carefully. The mixture was stirred at 60° C. for 16 hours, then cooled to room temperature. The reaction mixture was diluted with ether and filtered. The solution was washed with 10% NaOH, 50% brine, dried over $MgSO_4$, and the solvent Awas removed. The residue was chromatographed on silica gel, eluting with 100:0 to 60:40 hexane:EtOAc to give 620 mg of title compound: $^1H$ NMR ($CDCl_3$, 300 MHz) δ 1.73 (s, 9H), 1.85–2.30 (m, 4H), 3.05–3.22 (m, 2H), 4.42 (m, 1H), 6.78 (s, 1H), 7.16 (dd, 1H), 7.68 (dd, 1H), 8.48 (dd, 1H); MS m/z: 289 (M+H)⁺.

3c. 2-(2-(R)-pyrrolidinyl)furo[3,2-b]pyridine dihydrochloride

A 614 mg (2.13 mmol) sample of 2-(1-BOC-2-(R)-pyrrolidinyl)furo[3,2-b]pyridine, from step 3b above, was dissolved in 3 mL of $CH_2Cl_2$, and the solution was cooled to 0° C. To this solution was added 3 mL of TFA, and the reaction mixture was stirred at 0° C. for 2 hours. The reaction was quenched with saturated aqueous $K_2CO_3$ solution, and the mixture was extracted with $CH_2Cl_2$. The organic extract was dried over $MgSO_4$, and the solvent was removed. The residue was purified by chromatography on silica gel and treated with HCl in $Et_2O$ as described in Example 1e above to obtain the title compound: $^1H$ NMR ($D_2O$, 300 MHz) δ 2.17–2.69 (m, 4H), 3.52–3.59 (m, 2H), 5.14 (t, 1H, J=5.5 Hz), 7.42 (t, 1H, J=1 Hz), 7.80 (dd, 1H, J=5.6, 8.5 Hz), 8.5 (dt, 1H, J=1, 8.5 Hz), 8.70 (dd, 1H, J=1, 5.5 Hz); MS m/z: 189 (M+H)⁺, 206 (M+NH₄)⁺; Anal. Calcd for $C_{11}H_{12}N_2O.2.0$ HCl.0.5 $H_2O$: C, 48.90; H, 5.60; N, 10.90. Found: C, 48.75; H, 5.74; N, 10.11.

EXAMPLE 4

Preparation 2-(1-methyl-2-(R)-pyrrolidinyl)furo[3,2-b]pyridine dihydrochloride

A 140 mg sample of the compound from Example 3 above was dissolved in 8 mL of 37% aqueous formaldehyde and 4 mL of 88% formic acid and heated at reflux for 1 hour. The solution was poured into saturated aqueous $K_2CO_3$ solution, and the mixture was extracted with $CH_2Cl_2$. The organic extract was dried, concentrated and purified by chromatography on silica gel, eluting with 100:0 to 95:5 $CHCl_3$:MeOH. The product was dissolved in ethanol, and a solution of HCl in $Et_2O$ was added dropwise at ambient temperature. The resultant white precipitate was then collected by evaporation of solvent and triturated with three portions of $Et_2O$ to give the title compound (60 mg): $^1H$ NMR ($D_2O$, 300 MHz) δ 2.35 (br, 2H), 2.53–2.70 (m, 3H), 3.00 (br s, 3H), 3.40 (br s, 1H), 3.90 (br s, 1H), 7.38 (s, 1H), 7.60 (dd, 1H), 8.33 (d, 1H), 8.64 (dd, 1H); MS m/z: 203 (M+H)⁺, 220 (M+NH₄)⁺; Anal. Calcd for $C_{12}H_{14}N_2O.2.0$ HCl.1.0 $H_2O$: C, 49.16; H, 6.1; N, 9.55. Found: C, 49.03; H, 6.08; N, 9.13.

EXAMPLE 5

Preparation 5-methyl-2-(2-(S)-pyrrolidinyl)furo[3,2-b]pyridine dihydrochloride 5a. 2-(1-BOC-2-(S)-pyrrolidinyl)-5-methylfuro[3,2-b]pyridine A 3.10 g (13.2 mmol) sample of 6-iodo-2-picoline-5-ol (Aldrich Chem. Co.) was dissolved in 5 mL of DMF, and $(Ph_3P)_2PdCl_2$ (0.38 g, 0.50 mmol), CuI (0.377 g, 1.98 mmol) and triethylamine (1.80 mL, 13.2 mmol) were added. The mixture was stirred under $N_2$ at room temperature for 1 hour, then 2.15 g (11 mmol) of 1-BOC-2-(S)-ethynylpyrrolidine, from Example 1c above, dissolved in 1 mL of DMF, was added carefully. The reaction was stirred at 60° C. for 16 hours, then cooled to room temperature. The reaction mixture was diluted with 2 N HCl and extracted with ether. The aqueous layer was adjusted to pH 10 with $K_2CO_3$, then extracted with $CH_2Cl_2$. The extract was washed with 20% NaOH, brine, dried over $MgSO_4$, and the solvent was removed. The residue was repeatedly dissolved in toluene and distilled to azeotropically remove the DMF. The residue was chromatographed on silica gel, eluting with 100:0 to 50:50 hexane:EtOAc to give 521 mg of title compound: $^1H$ NMR ($CDCl_3$, 300 MHz) δ 1.33 and 1.47 (2 s, 9H), 1.90–2.30 (m, 4H), 2.63 (s, 3H), 3.45–3.65 (m, 2H), 4.95 and 5.10 (2 s, 1H), 5.58 (s, 1H), 7.02 (d, 1H), 7.55 (d, 1H); MS m/z: 303 (M+H)⁺.

5b. 5-methyl-2-(2-(S)-pyyrrolidinyl)furo[3,2-b]pyridine dihydrochloride

To a 530 mg sample of the compound from step 5a above in 4 mL of $CH_2Cl_2$ at 0° C. was added 4 mL of TFA. The reaction mixture was stirred for 16 hours, then diluted with saturated aqueous $Na_2CO_3$, and extracted with $CH_2Cl_2$. The organic extract was dried over $MgSO_4$, and the solvent was removed. The residue was chromatographed on silica gel, eluting with 100:0 to 90:10 $CHCl_3$:EtOH. The residue was treated with HCl/ether, and the salt was recrystallized from ethanol/EtOAc to give 158 mg of title compound: $^1H$ NMR (DMSO, 300 MHz) δ 2.0–2.5 (m, 4H), 2.55 (s, 3H), 3.34 (m, 3H), 4.93 (m, 1H), 7.24 (s, 1H), 7.27 (d, 1H), 7.97 (d, 1H);

MS m/z: 203 (M+H)$^+$, 220 (M+NH$_4$)$^+$; Anal. Calcd for C$_{12}$H$_{14}$N$_2$O.2.0 HCl.0.5 H$_2$O: C, 50.72; H, 6.03; N, 9.86. Found: C, 50.53; H, 6.06; N, 9.62.

EXAMPLE 6

Preparation of 2-(1-methyl-2-(S)-pyrrolidinyl)-5-methylfuro[3,2-b]pyridine dihydrochloride A 315 mg (1.04 mmol) sample of 2-(2-(S)-pyrrolidinyl)-5-methylfuro[3,2-b]pyridine dihydrochloride, from Example 5b above, was dissolved in 5 mL of 88% formic acid and 10 mL of 37% aqueous formaldehyde and heated at reflux for 0.5 hours. The reaction mixture was cooled, diluted with 2 N HCl and extracted with ether. The aqueous solution was adjusted to pH 10 with K$_2$CO$_3$ and extracted with CH$_2$Cl$_2$. The CH$_2$Cl$_2$ extract was dried over MgSO$_4$, and the solvent was removed. The residue was chromatographed on silica gel, eluting with 100:0 to 95:5 CHCl$_3$:EtOH The residue was converted to the salt by treatment with HCl/ether, and the salt was recrystallized from EtOH/EtOAc to give 332 mg of title compound: $^1$H NMR (DMSO, 300 MHz) δ 2.13–2.23 (m, 2H), 2.35–2.60 (m, 3H), 2.71 (s, 3H), 2.88 (s, 2H), 3.33 (br s, 1H), 3.70 (br s, 1H), 4.88 (m, 1H), 7.54 (d, 1H, J=8.8 Hz), 7.61 (s, 1H), 8.36 (d, 1H, J=8.5 Hz); MS m/z: 217 (M+H)$^+$, 234 (M+NH$_4$)$^+$; Anal. Calcd for C$_{13}$H$_{16}$N$_2$O.2.0 HCl.1.0 H$_2$O: C, 50.82; H, 6.55; N, 9.12. Found: C, 50.47; H, 6.77; N, 8.92.

EXAMPLE 7

Preparation of 6-chloro-2-(2-(S)-pyrrolidinyl)-furo[3,2-b]pyridine dihydrochloride 7a. 5-chloro-2-iodo-3-pyridinol A 20.3 g (0.157 mol) sample of 5-chloro-3-pyridinol (Aldrich Chemical Co.) and 35 g (0.33 mol) of Na$_2$CO$_3$ were dissolved in 220 mL of H$_2$O. To this solution was added 39.9 g of I$_2$, and the reaction mixture was stirred for 45 minutes. The mixture was then poured slowly into 2 N HCl, and the acidity was adjusted to pH 3. The product was collected by filtration and crystallized from EtOH/ether, affording 23.35 g of title compound: $^1$H NMR (CDCl$_3$, 300 MHz) δ 5.45 (s, 1H), 8.0 (d, 1H); MS m/z: 256 (M+H)$^+$, 273 (M+NH$_4$)$^+$.

7b. 2-(1-BOC-2-(S)-pyrrolidinyl)-6-chlorofuro[3,2-b]pyridine

A 5.63 g (22.0 mmol) sample of 5-chloro-2-iodo-3-pyridinol, from step 7a above, was dissolved in 10 mL of DMF, and (Ph$_3$P)$_2$PdCl$_2$ (0.38 g, 0.50 mmol), CuI (0.377 g, 1.98 mmol) and triethylamine (1.90 mL, 13.6 mmol) were added. The mixture was stirred under N$_2$ at room temperature for 1 hour, then 2.15 g (11.0 mmol) of 1-BOC-2-(S)-ethynylpyrrolidine, from Example 1c above, dissolved in 5 mL of DMF, was added carefully. The reaction was stirred at 60° C. for 16 hours, then cooled to room temperature. The reaction mixture was diluted with ether, then washed with 10% NaOH and brine, then dried over MgSO$_4$. The solvent was removed, and the residue was chromatographed on silica gel, eluting with 100:0 to 60:40 hexane:EtOAc to give 2.04 g of title compound: $^1$H NMR (CDCl$_3$, 300 MHz) δ 1.3, 1.45 (2 s, 9H), 1.94–2.3 (m, 4H), 3.45–3.65 (m, 2H), 4.97–5.1 (m, 1H). 6.66 (s, 1H), 7.70 (s, 1H), 8.47 (s, 1H); MS m/z: 323 (M+H)$^+$.

7c. 6-chloro-2-(2-(S)-pyrrolidinyly-furo[3,2-b]pyridine dihydrochloride

To a 2 g sample of the compound from step 7b above in 10 mL of CH$_2$Cl$_2$ at 0° C. was added 10 mL of TFA, and the reaction mixture was stirred for 1 hour, poured into saturated aqueous Na$_2$CO$_3$ and extracted with CH$_2$Cl$_2$. The organic extract was dried over MgSO$_4$, and the solvent was removed. The residue was chromatographed on silica gel, eluting with 99:1 to 95:5 CHCl$_3$:MeOH. The product was treated with HCl/ether, and the salt was recrystallized from EtOH/EtOAc to give 1.2 g of title compound: $^1$H NMR (D$_2$O, 300 MHz) δ 2.18–2.50 (m, 3H), 2.54–2.65 (m, 1H), 3.51–3.36 (m, 2H), 5.06 (t, 1H, J=8 Hz), 7.26 (d, 1H, J=0.7 Hz), 8.24 (dd, 1H, J=0.7, 1.8 Hz), 8.60 (d, 1H, J=1.8 Hz); MS m/z: 223 (M+H)$^+$, 240 (M+NH$_4$)$^+$; Anal. Calcd for C$_{11}$H$_{11}$N$_2$OCl.2.0 HCl: C, 44.69; H, 4.43; N, 9.47. Found: C, 44.57; H, 4.31; N, 9.33.

EXAMPLE 8

Preparation of 6-chloro-2-(1-methyl-2-(S)-pyrrolidinyl)-furo[3,2-b]pyridine dihydrochloride A 315 mg (1.04 mmol) sample of 6-chloro-2-(2-(S)-pyrrolidinyl)-furo[3,2-b]pyridine dihydrochloride, from Example 7c above, was dissolved in 3 mL of 88% formic acid and 6 mL of 37% aqueous formaldehyde and heated at reflux for 0.5 hour. The reaction mixture was cooled, poured into saturated K$_2$CO$_3$, and the mixture was extracted with CH$_2$Cl$_2$. The extract was dried over MgSO$_4$, and the solvent was removed. The residue was chromatographed on silica gel, eluting with 100:0 to 95:5 CHCl$_3$:MeOH. The residue was converted to the salt by treatment with HCl/ether, and the salt was recrystallized from ethanol/EtOAc to give 159 mg of title compound: $^1$H NMR (D$_2$O, 300 MHz) δ 2.31–2.39 (m, 2H), 2.52–2.70 (m, 3H), 2.96 (br s, 3H), 3.55 (br s, 1H), 3.88 (br s, 1H), 7.33 (s, 1H), 8.13 (dd, 1H), 8.56 (d, 1H); MS m/z: 237 (M+H)$^+$, 254 (M+NH$_4$)$^+$; Anal. Calcd for C$_{12}$H$_{13}$N$_2$OCl.2HCl: C, 46.55; H, 4.88; N, 9.05. Found: C, 50.75; H, 5.12; N, 9.69.

EXAMPLE 9

Preparation of 2-(2-(S)-pyrrolidinyl)furo[2,3-c]pyridine dihydrochloride 9a. 4-iodo-3-methoxymethoxypyridine The title compound was prepared according to the procedure of Winkle and Ronald, *J. Org. Chem.*, 47:2101–2106 (1982).

9b. 3-hydroxy-4-iodopyridine

A 1.48 g (5.3 mmol) sample of 4-iodo-3-methoxymethoxypyridine, from step 9a above, was suspended in 10 mL of 50% aqueous acetic acid and 4 drops of concentrated H$_2$SO$_4$, and the mixture was heated at reflux for 20 minutes. The solution was cooled, adjusted to pH 3 with solid Na$_2$CO$_3$, diluted with water, and extracted with EtOAc. The organic extract was dried over MgSO$_4$, and the solvent was removed to give 0.86 g of the title compound: MS m/z: 223 (M+H)$^+$, 239 (M+NH$_4$)$^+$.

9c. 2-(1-BOC-2-(S)-pyrrolidinyl)furo[2,3-c]pyridine

A 829 mg (3.7 mmol) sample of 3-hydroxy-4-iodopyridine, from step 9b above, 130 mg (0.18 mmol) of (Ph$_3$P)$_2$PdCl$_2$, 170 mg (0.74 mmol) of CuI, and 0.6 mL of triethylamine were combined in 10 mL of DMF at ambient temperature and stirred for 3 hours. To this mixture was added a solution of 1-BOC-2-(S)-ethynylpyrrolidine (1.5 g, 7.7 mmol, from Example 1c above) in 5 mL of DMF, and the reaction mixture was stirred at 60° C. for 16 hours. The reaction mixture was cooled to room temperature and diluted with ether. The ether layer was filtered, washed with 10% NaOH then 50% brine, dried over MgSO$_4$, and concentrated. The residue was purified by chromatography on silica gel, eluting with 100:0 to 50:50 hexane:EtOAc to give the title compound.

9d. 2-(2-(S)-pyrrolidinyl)furo[2,3-c]pyridine dihydrochloride

To a 700 mg sample of the compound from step 9c above in 5 mL of CH$_2$Cl$_2$ at 0° C. was added 5 mL of TFA. The reaction mixture was stirred for 1 hour at 0° C. then poured into saturated Na$_2$CO$_3$, and the layers were separated. The aqueous layer was extracted with CH$_2$Cl$_2$. The combined organic layers were dried over MgSO$_4$ and concentrated, and the residue was chromatographed on silica gel, eluting with 100:0 to 95:5 CHCl$_3$:MeOH. The product was converted to the salt by treatment with HCl/ether, which was recrystallized from ethanol/EtOAc: $^1$H NMR (D$_2$O, 300 MHz) δ 2.19–2.52 (m, 3H), 2.64 (m, 1H), 3.53–3.58 (m, 2H), 5.13 (t, 1H, J=8 Hz), 7.34 (s, 1H), 8.05 (dd, 1H, J=0.8, 5.8 Hz), 8.49 (d, 1H, J=5.8 Hz), 9.07 (s, 1H); MS m/z: 189 (M+H)$^+$, 206 (M+NH$_4$)$^+$; Anal. Calcd for C$_{11}$H$_{12}$N$_2$O·2.0 HCl.H$_2$O: C, 47.33; H, 5.78; N, 10.03. Found: C, 47.32; H, 5.83; N, 9.90.

EXAMPLE 10

Preparation of 2-(1-methyl-2-(S)-pyrrolidinyl)furo[2,3-c]pyridine dihydrochloride A 120 mg sample of the compound from Example 9 above was dissolved in 4 mL of formic acid and 2 mL of formalin, and the reaction mixture was heated at reflux for 30 minutes. The reaction mixture was cooled to ambient temperature and poured into saturated K$_2$CO$_3$ solution. The resulting mixture was extracted with CH$_2$Cl$_2$, the extract was dried, and the solvent was removed. The residue was chromatographed on silica gel, and the compound was converted to the salt by treatment with HCl/ether: $^1$H NMR (D$_2$O, 300 MHz) δ 2.30–2.40 (m, 3H), 2.50–2.74 (m, 1H), 2.98 (s, 3H), 3.45 (br d, 1H), 3.85 (br s, 1H), 4.97 (t, 1H), 7.47 (s, 1H), 8.08 (d, 1H), 8.51 (d, 1H), 9.10 (s, 1H); MS m/z: 203 (M+H)$^+$; Anal. Calcd for C$_{12}$H$_{14}$N$_2$O·2 HCl.0.5H$_2$O: C, 50.70; H, 6.03; N, 9.86. Found: C, 50.69; H, 6.09; N, 9.61.

EXAMPLE 11

Preparation of 5-chloro-2-(2-(S)-pyrrolidinyl)-furo[3,2-b]pyridine hydrochloride 11a. 5-acetoxy-2-chloropyridine To a solution of 5-amino-2-chloropyridine (40.0 g, 0.311 mol) in 180 mL of 3:1 1,2-dimethoxyethane/CH$_2$Cl$_2$ at –10° C. was slowly added boron trifluoride diethyl etherate (76.5 mL, 0.662 mol). Then a solution of tert-butyl nitrite (44.4 mL, 0.373 mol) in 40 mL of 1,2-dimethoxyethane was slowly added over 15 min such that the reaction temperature remained below –5° C. The mixture was stirred for 10 min at –10° C. then warmed to 0° C. and stirred for an additional 30 min. Pentane was added and the solid was collected by suction filtration (cold pentane wash) to afford 69.1 g of the tetrafluoroborate diazonium salt. This was dissolved in 350 mL of acetic anhydride, warmed to 75° C. (N$_2$ evolution) and stirred for 3 h. The volatiles were removed in vacuo and the dark residue was diluted with Et$_2$O and washed with saturated aqueous NaHCO$_3$. The aqueous phase was extracted with Et$_2$O. The combined ethereal extracts were washed with brine, dried (MgSO$_4$), and concentrated. Purification by chromatography (silica gel; hexane/EtOAc 90:10 to 70:30) afforded the title compound as a white solid (29.4 g, 55%): mp 45° C.; $^1$H NMR (CDCl$_3$, 300 MHz) δ 2.35 (s, 3H) 7.35 (d, J=8.5 Hz, 1H), 7.48 (dd, J=2.9, 8.5 Hz, 1H), 8.21 (d, J=2.9 Hz, 1H); MS (CI/NH$_3$) m/z: 172, 174 (M+H)$^+$; 189, 191 (M+NH$_4$)$^+$.

11b. 2-chloro-5-hydroxypyridine

5-Acetoxy-2-chloropyridine (11.1 g, 64.7 mmol) from step 11a was dissolved in MeOH at ambient temperature and solid potassium carbonate (4.47 g, 32.4 mmol) was added. After stirring for 2 h, the volatiles were removed in vacuo and the residue was diluted with Et$_2$O and H$_2$O. The aqueous phase was neutralized to pH 7 by the addition of 1 N aqueous HCl. The layers were separated and the aqueous phase was extracted twice with Et$_2$O. The combined organic extracts were dried (MgSO$_4$) and concentrated to provide the title compound as a white solid (8.03 g, 96%): mp 155° C.; $^1$H NMR (CD$_3$OD, 300 MHz) δ 7.20–7.28 (m, 2H), 7.88 (m, 1H); MS (CI/NH$_3$) m/z: 130,132 (M+H)$^+$; 147,149 (M+NH$_4$)$^+$.

11c. 6-chloro-2-iodo-3-pyridinol

To a solution of 2-chloro-5-hydroxypyridine (5 g, from step 11b) and 8.6 g of Na$_2$CO$_3$ in 100 mL of water was added 9.8 g of I$_2$. The mixture was stirred until the iodine color disappeared. The reaction mixture was then adjusted to pH 5 and extracted with EtOAc. The extract was dried over MgSO$_4$, and the solvent was removed. The residue was recrystallized from MeOH to afford 5.4 g of the title compound: $^1$H NMR (CD$_3$OD, 300 MHz) δ 7.09 (d, 1H, J=8.5 Hz), 7.20 (d, 1H, J=8.5 Hz); MS m/z: 256 (M+H)$^+$, 273 (M+NH$_4$)$^+$.

11d. 2-(1-BOC-2-(S)-pyrrolidinyl)-5-chlorofuro[3,2-b]pyridine

A 3.07 g (12.0 mmol) sample of 6-chloro-2-iodo-3-pyridinol, from step 11c above, was dissolved in 10 mL of DMF, and (Ph$_3$P)$_2$PdCl$_2$ (0.38 g, 0.50 mmol), CuI (0.380 g, 1.98 mmol) and triethylanue (1.7 mL, 12 mmol) were added. The mixture was stirred under N$_2$ at room temperature for 1 hour, then 1.95 g (10.0 mmol) of 1-BOC-2-(S)-ethynylpyrrolidine, from Example 1a above, dissolved in 5 mL of DMF, was added carefully. The reaction mixture was stirred at 60° C. for 16 hours, cooled to room temperature, diluted with ether, washed with 50% brine and dried over MgSO$_4$, then the solvent was removed. The residue was chromatographed on silica gel, eluting with 100:0 to 50:50 hexane:EtOAc to give 1.54 g of title compound: $^1$H NMR (DMSO, 300 MHz, 130° C.) δ 1.37 (two s, 9H), 1.89–2.07 (m, 3H), 2.37 (m, 1H), 3.40–3.54 (m, 1H), 4.98 (m, 1H), 6.72 (s, 1H), 7.26–7.29 (d, 1H, J=8.6 Hz), 7.93–7.96 (d, 1H, J=8.6 Hz); MS m/z: 323 (M+H)$^+$.

11e. 5-chloro-2-(2-(S)-pyrrolidinyl)-furo[3,2-b]pyridine hydrochloride

A 1.5 g sample of the compound from step 11d above was dissolved in 10 mL of CH$_2$Cl$_2$ and cooled to 0° C. The solution was stirred under N$_2$, 10 mL of TFA was added, and the reaction mixture was stirred for 1 hr. The reaction mixture was poured into saturated K$_2$CO$_3$, and the mixture was extracted with CH$_2$Cl$_2$. The solution was dried over MgSO$_4$, and the solvent was removed. The residue was chromatographed on silica gel, eluting with 99:1 to 95:5 CHCl$_3$:MeOH. The residue was converted to the salt by treatment with HCl/ether to give 0.78 g of title compound: $^1$H NMR (D$_2$O, 300 MHz) δ 2.22–2.65 (m, 4H), 3.52–3.57 (m, 2H), 5.06 (t, 1H, J=8 Hz), 7.15 (d, 1H), 7.48 (d, 1H, J=8.6 Hz), 8.1 (d, 1H, J=8.6 Hz); MS m/z: 223 (M+H)$^+$, 240 (M+NH$_4$)$^+$; Anal. Calcd for C$_{11}$H$_{11}$N$_2$OCl.1.0 HCl: C, 50.99; H, 4.67 N, 10.81. Found: C, 51.21; H, 4.79; N, 10.55.

EXAMPLE 12

Preparation of 5-chloro-2-(1-methyl-2-(S)-pyrrolidinyl)-furo[3,2-b]pyridine hydrochloride A 660 mg (1.04 mmol) sample of 2-(2-(S)-pyrrolidinyl)-5-chlorofuro[3,2-b]pyridine dihydrochloride, from Example 11e above, was dissolved in 5 mL of 88% formic acid and 10 mL of 37% aqueous formaldehyde and heated at reflux for 1 hour. The reaction mixture was cooled, poured into saturated $K_2CO_3$, and the mixture was extracted with $CH_2Cl_2$. The extract was dried over $MgSO_4$, and the solvent was removed. The residue was chromatographed on silica gel, eluting with 100:0 to 95:5 $CHCl_3$:MeOH. The residue was converted to the salt by treatment with HCl/ether to give 540 mg of title compound: $^1$H NMR ($D_2O$, 300 MHz) δ 2.28–2.38 (m, 2H), 2.49–2.72 (m, 2H), 2.92 (br s, 3H), 3.41 (m, 1H), 3.80 (m, 1H), 4.84 (m, 1H), 7.50 (d, 1H, J=8.8 Hz), 8.0 (d, 1H, J=8.8 Hz), 8.56 (d, 1H); MS m/z: 237 (M+H)$^+$; Anal. Calcd for $C_{12}H_{13}N_2OCl.1.0$ HCl. C, 52.07; H, 5.13; N, 10.12. Found: C, 51.85; H, 5.46; N, 9.78.

EXAMPLE 13

Preparation of 5-chloro-2-(2-(S)-pyrrolidinyl)-furo [2,3-b]pyridine hydrochloride 13a. 5-chloro-3-iodo-2-pyridinol A 6.48 g sample of 5-chloro-2-pyridinol (Aldrich) and 10.8 g of $Na_2CO_3$ were dissolved in 250 mL of water. To this solution was added 12.73 g of $I_2$, and the mixture was stirred until the iodine color disappeared. The reaction mixture was then adjusted to pH 7 and extracted with EtOAc. The extract was dried over $MgSO_4$, and the solvent was removed. The residue was recrystallized from ethanol/water to afford 4 g of the title compound: $^1$H NMR (DMSO-$d_6$, 300 MHz) δ 7.71 (d,1H), 8.18 (d, 1H); MS m/z: 256 (M+H)$^+$, 273 $(M+NH_4)_+$.

13b. 2-(1-BOC-2-(S)-pyrrolidinyl)-5-chlorofuro[2,3-b] pyridine

A 3.07 g (12 mmol) sample of 5-chloro-3-iodo-2-pyridinol, from step 13a above, was dissolved in 10 mL of DMF, and $(Ph_3P)_2PdCl_2$ (0.39 g, 0.5 mmol), CuI (0.38 g, 1.98 mmol) and triethylamine (1.7 mL, 12 mmol) were added. The mixture was stirred under $N_2$ at room temperature for 1 hour, then 1.95 g (10 mmol) of 1-BOC-2-(S)-ethynylpyrrolidine, from Example 1c above, dissolved in 5 mL of DMF, was added carefully. The reaction mixture was stirred at 60° C. for 16 hours, cooled to room temperature, diluted with ether and washed with 50% brine. The organic layer was dried over $MgSO_4$ and concentrated. The residue was chromatographed on silica gel, eluting with 100:0 to 50:50 hexane:EtOAc to give 1.55 g of title compound: MS m/z: 323 (M+H)$^+$.

13c. 5-chloro-2-(2-(S)-prrolidinyl)-furo[2,3-b]pyridine hydrochloride

A 0.56 g sample of the compound from step 13b above was dissolved in 3 mL of $CH_2Cl_2$ and cooled to 0° C. The solution was stirred under $N_2$, 3 mL of TFA was added, and the reaction mixture was stirred for 1 hour. The reaction mixture was poured into saturated $K_2CO_3$, and the mixture was extracted with $CH_2Cl_2$. The solution was dried over $MgSO_4$, and the solvent was removed. The residue was chromatographed on silica gel, eluting with 99:1 to 95:5 $CHCl_3$:MeOH. The product was converted to the salt by treatment with HCl/ether to give 0.36 g of title compound: $^1$H NMR ($D_2O$, 300 MHz) δ 2.22–2.60 (m, 4H), 3.50–3.56 (m, 2H), 5.01 (t, 1H, J=8.1 Hz), 7.10 (s, 1H, ), 7.82 (d, 1H, J=2.3 Hz), 8.33 (d, 1H, J=2.3 Hz); MS m/z: 223 (M+H)$^+$, 240 (M+NH$_4$)$^+$; Anal. Calcd for $C_{11}H_{11}N_2OCl.1.0$ HCl: C, 50.99; H, 4.67 N, 10.81. Found: C, 51.06; H, 4.64; N, 10.65.

EXAMPLE 14

Preparation of 5-chloro-2-(1-methyl-2-(S)-pyrrolidinyl)-furo[2,3-b]pyridine dihydrochloride A 200 mg (0.80 mmol) sample of 5-chloro-2-(2-(S)-pyrrolidinyl)-furo[2,3-b]pyridine dihydrochloride, from Example 13c above, was dissolved in 4 mL of 88% formic acid and 8 mL of 37% aqueous formaldehyde and heated at reflux for 1 hour. The reaction mixture was cooled, poured into saturated $K_2CO_3$, and the mixture was extracted with $CH_2Cl_2$. The extract was dried over $MgSO_4$, and the solvent was removed. The residue was chromatographed on silica gel, eluting with 100:0 to 95:5 $CHCl_3$:MeOH. The product was converted to the salt by treatment with HCl/ether to give 140 mg of title compound: $^1$H NMR ($D_2O$, 300 MHz) δ 2.29–2.38 (m, 2H), 2.49–2.68 (m, 2H), 2.95 (br s, 3H), 3.44 (m, 1H), 3.84 (m, 1H), 4.84 (m, 1H), 7.22 (s, 1H), 8.22 (d, 1H, J=2.3 Hz), 8.36 (d, 1H, J=2.4); MS m/z: 237 (M+H)$^+$, 254 (M+NH$_4$)$^+$; Anal. Calcd for $C_{12}H_{13}N_2OCl.1.0$ HCl.0.3 $H_2O$: C, 51.74; H, 5.28; N, 9.73. Found: C, 51.74; H, 5.28; N, 10.16.

EXAMPLE 15

Preparation of 2-(Hexahydro-1H-7a-pyrrolizinyl) furo[3,2-b]pyridine hydrochloride 15a. 1,2,3,5,6,7-Hexahydropyrrolizinium perchlorate The title compound was prepared using the procedures of Miyano et al., *Synthesis*, 1978: 701–702, and *J. Heterocyclic Chem.*, 19:1465–1468 (1982).

15b. 7a-Ethynyl-hexahydro-1H-pyrrolizine

The compound from step 15a above (1.0 g, 4.8 mmol) was added to a solution of 0.5 M ethynylmagnesium bromide (29 mL, 14.3 mmol) in THF at room temperature. The reaction mixture was stirred for 45 minutes, quenched with 15% NaOH solution, and diluted with brine:water (1:1). The aqueous phase was extracted with $CH_2Cl_2$, and the organic phases were combined, dried ($MgSO_4$), concentrated and chromatographed (silica gel; $CHCl_3$/MeOH, 90:10) to afford an amber oil (463 mg, 71%): $^1$H NMR ($CDCl_3$, 300 MHz) δ 1.75–2.06 (m, 6H), 2.14–2.23 (m, 2H), 2.33 (s, 1H), 2.53–2.62 (m, 2H), 322–3.28 (m, 2H); MS (CI/NH$_3$) m/z: 136 (M+H)$^+$.

15c. 2-(Hexahydro-1H-7a-pyrrolizinyl)furo[3,2-b]pyridine

2-Iodo-3-pyridinol (902 mg, 4.1 mmol), copper(I) iodide (116 mg, 0.61 mmol), bis(triphenylphosphine)palladium(II) chloride (119 mg, 0.17 mmol) and triethylamine (570 mL, 4.1 mmol) were combined in DMF (4.5 mL) and stirred for one hour. 7a-Ethynyl-hexahydro-1H-pyrrolizine(460 mg, 3.4 mmol) in DMF (1.2 mL) was added dropwise and the mixture was heated at 60° C. for 18 h. The reaction mixture was allowed to cool to ambient temperature and 2 N aqueous HCl was added. The heterogeneous mixture was washed with $Et_2O$ (2x), basified with 15% NaOH solution and extracted with $CH_2Cl_2$ (2x). The $CH_2Cl_2$ extracts were combined, dried ($MgSO_4$) concentrated and chromatographed (silica gel; $CHCl_3$/MeOH, 96:4) to afford an amber oil which solidified upon storage at −20° C. (405 mg, 52%): mp 39–41° C.; $^1$H NMR ($CDCl_3$, 300 MHz) δ 1.86–1.97 (m, 6H), 2.24–2.34 (m, 2H), 2.68–2.76 (m, 2H), 3.21–3.28 (m, 2H), 6.77 (s, 1H), 7.12 (dd, J=8.5, 5 Hz, 1H), 7.65 (d, J=8.5 Hz, 1H), 8.46 (d, J=5 Hz, 1H); MS (CI/NH$_3$) m/z: 229 (M+H)$^+$.

15d. 2-(Hexahydro-1H-7a-pyrrolizinyl)furo[3,2-b]pyridine hydrochloride

The free base (395 mg, 1.73 mmol), from step 15c above, was dissolved in THF (30 mL) and a saturated solution of HCl in $Et_2O$ was added until precipitation ceased. The solvent was decanted and the remaining light yellow solid triturated with THF (2x). The product was recrystallized from MeOH/$Et_2O$ to afford a light yellow powder, (349 mg, 76%): mp 201–203° C. dec.; $^1$H NMR (DMSO, 300 MHz) δ 2.09–2.37 (m, 6H), 2.62–2.73 (m, 2H), 3.23–3.40 (m, 2H), 3.57–3.70 (m, 2H), 7.40 (dd, J=8, 5 Hz, 1H), 7.53 (s, 1H), 8.05 (dd, J=8, 1 Hz, 1H), 8.56 (dd, J=5, 1 Hz, 1H), 11.35 (br s); MS (CI/NH$_3$) m/z: 229 (M+H)$^+$; Anal. Calcd for C$_{14}$H$_{16}$N$_2$O.1.1HCl: C, 62.81; H, 6.51; N, 10.42. Found: C, 62.65; H, 6.42; N, 10.44.

EXAMPLE 16

Preparation of 2-(Hexahydro-1H-7a-pyrrolizinyl)-5-methylfuro[3,2-b]pyridine dihydrochloride 16a. 2-(Hexahydro-1H-7 a-pyrrolizinyl)-5-methylfuro[3,2-b]pyridine The acetylene compound 7a-ethynyl-hexahydro-1H-pyrrolizine (450 mg, 3.33 mmol), 2-iodo-6-methyl-3-pyridinol (939 mg, 4.0 mmol)(Aldrich), copper(I) iodide (114 mg, 0.6 mmol), bis(triphenylphosphine)palladium(II) chloride (117 mg, 0.17 mmol) and triethylamine (560 mL, 4.0 mmol) were combined in a similar fashion as that described for Example 1d. The residue was chromatographed (silica gel; CHCl$_3$/MeOH, 96:4) to afford a yellow solid (403 mg, 50%): $^1$H NMR (CDCl$_3$) δ 1.85–1.95 (m, 6H), 2.25–2.30 (m, 2H), 2.62 (s, 3H), 2.67–2.75 (m, 2H), 3.19–3.26 (m, 2H), 6.68 (s, 1H), 6.98 (d, J=8 Hz, 1H), 7.54 (d, J=8 Hz, 1H); MS (CI/NH$_3$) m/z: 243 (M+H)$^+$.

16b. 2-(Hexahydro-1H-7a-pyrrolizinyl)-5-methylfuro[3,2-b]pyridine dihydrochloride A sample of the compound from step 16a (395 mg, 1.63 mmol) (395 mg, 1.63 mmol) was dissolved in CH$_2$Cl$_2$ (20 mL) and a saturated solution of HCl in Et$_2$O was added dropwise. The solvent was removed to afford a yellow oil/solid (390 mg, 72%): $^1$H NMR (D$_2$O, 300 MHz) δ 2.30–2.48 (m, 6H), 2.75–2.84 (m, 5H), 3.35–3.45 (m, 2H), 3.77–3.85 (m, 2H), 7.39 (s, 1H), 7.62 (d, J=9 Hz, 1H), 8.31 (d, J=9 Hz, 1H); MS (CI/NH$_3$) m/z: 243 (M+H)$^+$; Anal. Calcd for C$_{15}$H$_{18}$N$_2$O.2.0 HCl.1.0 H$_2$O: C, 54.06; H, 6.65; N, 8.41. Found: C, 54.00; H, 6.33; N, 8.11.

EXAMPLE 17

Preparation of 2-(Hexahydro-1H-7a-pyrrolizinyl)furo[2,3-c]pyridine dihydrochloride 17a. 2-(Hexahydro-1H-7a-pyrrolizinyl)furo[2,3-c]pyridine The acetylene compound 7a-ethynyl-hexahydro-1H-pyrrolizine (225 mg, 1.66 mmol), 4-iodo-3-pyridinol (441 mg, 2.0 mmol) from Example 9b, copper(I) iodide (60 mg, 0.30 mmol), bis(triphenylphosphine)-palladium(II) chloride (58 mg, 0.08 mmol) and triethylamine (280 mL, 2.0 mmol) were combined in a similar fashion as that described in Example 15c. The crude product was chromatographed (silica gel; CHCl$_3$/MeOH, 98:2 to 95:5) to afford a turbid yellow oil (185 mg, 49%): $^1$H NMR (CDCl$_3$, 300 MHz) δ 1.83–1.97 (m, 6H), 2.24–2.31 (m, 2H), 2.67–2.75 (m, 2H), 3.19–3.26 (m, 2H), 6.62 (s, 1H), 7.42 (d, J=5 Hz, 1H), 8.35 (d, J=5 Hz, 1H), 8.77 (s, 1H); MS (CI/NH$_3$) m/z: 229 (M+H)$^+$.

17b. 2-(Hexahydro-1H-7a-pyrrolizinyl)furo[2,3-c]pyridine dihydrochloride

A sample of the compound from step 17a (173 mg, 0.76 mmol) was dissolved in CH$_2$Cl$_2$ (10 mL) and a saturated solution of HCl in Et$_2$O was added until precipitation ceased. The solvent was removed and the product was recrystallized from MeOH/Et$_2$O to afford a light yellow solid (226 mg, 98%): mp 235–238° C.; $^1$H NMR (D$_2$O, 300 MHz) δ 2.30–2.49 (m, 6H), 2.76–2.85 (m, 2H), 3.35–3.45 (m, 2H), 3.77–3.86 (m, 2H), 7.41 (s, 1H), 8.04 (d, J=6 Hz, 1H), 8.49 (d, J=6 Hz, 1H), 9.05 (s, 1H); MS (CI/NH$_3$) m/z: 229 (M+H)$^+$; Anal. Calcd for C$_{14}$H$_{16}$N$_2$O.2.0 HCl.0.8 H$_2$O: C, 53.28; H, 6.26; N, 8.88. Found: C, 53.61; H, 6.49; N, 8.35.

EXAMPLE 18

Preparation of endo-2-(Hexahydro-1H-3-(R)-pyrrolizinyl)furo[3,2-b]pyridine dihydrochloride

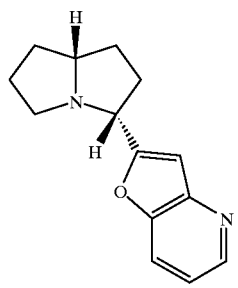

18a. 3-(N-BOC-2-(R)-pyrrolidinyl)propenal

To a solution of N-Boc-R-prolinal (10.25 g, 51.50 mmol) in 150 mL of anhydrous toluene at room temperature was added (triphenylphosphoranylidene)-acetaldehyde (17.2 g, 56.7 mmol), and the mixture was refluxed for 3 hours under nitrogen. The mixture was concentrated in vacuo. The residue was purified on silica gel, eluting with ¼ EtOAc/hexane. The title compound was obtained as an amber oil in 53% yield (6.13g): $^1$H NMR (CDCl$_3$, 300 MHz) δ 1.42 (s (major isomer), 9H), 1.49 (s (minor isomer), 9H), 1.73–1.90 (m, 3H), 2.06–2.24 (m, 1H), 3.37–3.54 (m, 1H), 4.41–4.52 (m (minor isomer), 1H), 4.58–4.68 (m (minor isomer), 1H), 6.11 (dd, 3.0 Hz, 8.0 Hz, 1H), 6.63–6.82 (m, 1H), 9.57 (s (minor isomer), 1H), 9.59 (s (major isomer), 1H); MS(DCI) (M+H)$^+$: 226, (M+NH$_4$)$^+$: 243.

18b. 3-(N-BOC-2-(R)-pyrrolidinyl)propanal

To a solution of the propenal compound from step 18a (27.20 mmol, 8.02 g) was added 100 mL of EtOAc and 0.5 g of 10% Pd/C. The mixture was agitated under 4 atmosphere of H$_2$ for 16 hours. The catalyst was removed by filtration, and the filtrate was concentrated under reduced pressure. The residue was purified on silica gel, eluting with ¼ EtOAc/hexane. The title compound was obtained in 97% yield as a yellow oil (5.99g): $^1$H NMR (CDCl$_3$, 300 MHz) δ 1.48 (s, 9H), 1.60 (m, 1H), 1.69–2.01 (m, 5H), 2.39–2.52 (m, 2H), 3.21–3.36 (m, 2H), 3.73–3.94 (m, 1H), 7.27 (s, 1H); MS (DCI) m/z: 228 (M+H)$^+$, 245 (M+NH$_4$)$^+$.

18c. 5-(N-BOC-2-(R)-pyrrolidinyl)-3-hydroxy-1-pentyne

A solution of the propanal compound from step 18b above (26.40 mmol, 5.99 g) in 100 mL of anhydrous THF under a nitrogen atmosphere was cooled to −78° C. To this solution was added ethynyl magnesium bromide (0.5 M in THF/ 79.20 mL), and the mixture was stirred at −78° C. for one hour. The mixture was then warmed to room temperature and stirred for 1.5 hours. The reaction was quenched by pouring it into 200 mL of saturated NH$_4$Cl. The mixture was extracted with CH$_2$Cl$_2$, and the extracts were dried over Na$_2$SO$_4$ and concentrated under vacuum. The residue was purified on silica gel, eluting with EtOAc/hexane (⅓). The title compound was obtained in 90% yield as a light yellow oil (5.99 g): $^1$H NMR (CDCl$_3$, 300 MHz) δ 1.47 (s, 9H), 1.58–2.00 (m, 8H), 2.41–249 (br s, 1H), 3.24–3.37 (m, 3H), 3.66–4.01 (br d, 1H), 4.31–4.51 (m, 1H); MS (DCI) m/z: 254 (M+H)$^+$; 271 (M+NH$_4$)$^+$.

18d. endo-hexahydro-1H-3-(R)-ethynylpyrrolizine and exo-hexahydro-1H-3-(S)-ethynyipyrrolizine To a solution of the alcohol compound from step 18c above (17.30 mmol, 4.38 g) in CH$_2$Cl$_2$ (30 mL) at room temperature was added triphenylphosphine dibromide (21.60 mmol, 9.12g), and the mixture was stirred for 16 hours. Next, 5 mL of TFA was added followed by stirring for another 4 hours at room temperature. The mixture was then concentrated under vacuum. The residue was purified by chromatography on silica gel, eluting with 10% MeOH/ $CH_2Cl_2$ containing 1% $NH_4OH$, to separate the exo and endo products The combined yield for the reaction was 64%.

endo-(R)-compound: $[\alpha]^{23}_D$-42.76 (c 0.14, $H_2O$); $^1H$ NMR ($CDCl_3$, 300 MHz) δ 1.32–1.48 (m, 2H), 1.69–1.74 (m, 4H), 1.75–2.04 (m, 2H), 2.38 (m, 1H), 2.75 (d, J=2.0 Hz, 1H), 2.67 (m, 1H), 3.07 (m, 1H), 3.36 (m, 1H), 3.60 (m, 1H); MS (DCI) m/z: 136 (M+H)$^+$, 153 (M+NH$_4$)$^+$; Anal. Calcd for $C_9H_{13}N.0.20$ $H_2O$: C,77.87; H, 9.73; N, 10.09. Found: C, 78.15; H, 9.87; N, 10.17.

exo-(S)-compound: $[\alpha]^{23}_D$+51.14 (c 0.37, $H_2O$); $^1H$ NMR ($CDCl_3$, 300 MHz) δ 1.42 (m, 1H), 1.62 (m, 1H), 1.88 (m, 1H), 1.89–2.19 (m, 5H), 2.22 (d, J=2.0 Hz, 1H), 2.90 (m, 1H), 3.07 (m, 1H), 3.53 (m, 1H), 3.88 (m, 1H); MS (DCI) m/z: 136 (M+H)$^+$, 153 (M+NH$_4$)$^+$; Anal. Calcd for $C_9H_{13}N.0.10$ $H_2O$: C,78.89; H, 9.71; N, 10.22. Found: C, 78.88; H, 9.59; N, 10.05.

18e. endo-2-(hexahydro-1H-3-(R)-pyrrolizinyl)furo[3,2-b] pyridine dihydrochloride To DMF (5.0 mL) in a flask purged with nitrogen was added 2-iodo-3-hydroxypyridine (1.20 mmol, 0.2652 g)(Aldrich), bis(triphenylphosphine)-palladium(II) chloride (0.05 mmol, 35 mg), copper(I)iodide (0.20 mmol, 38.1 mg), and triethylamine (1.2 mmol, 0.1214 g), and the mixture was stirred for one hour at room temperature. The endo-(R)-acetylene compound from step 18d above (1.0 mmol, 0.134 g in 5.0 mL of DMF) was then added and the mixture was heated at 60° C. for 16 hours. The mixture was cooled and poured into 2 N HCl (100 mL), and the mixture was extracted with $CH_2Cl_2$ (2×75 mL). The aqueous layer was basified with solid $K_2CO_3$ and extracted with $CH_2Cl_2$, and the extract was dried over $MgSO_4$ and concentrated under vacuum. The residue was purified on silica gel, eluting with 10% MeOH in $CH_2Cl_2$. The title compound was obtained by treating the base with a saturated solution of HCl/EtOH at 0° C.: $[\alpha]^{\leqq}_D$+26.21 (c 0.12, MeOH); $^1H$ NMR ($CDCl_3$, 300 MHz) δ 1.96–2.13 (m, 2H), 2.15–2.40 (m, 3H), 2.51–2.78 (m, 3H), 3.57–3.69 (m, 2H), 4.45–4.57 (m, 1H), 4.96–5.08 (m, 1H), 7.65 (bs, 1H), 7.95–8.07 (m, 1H), 8.28–8.37 (m, 1H), 8.51–8.71 (d, J=10,0 Hz, 1H); MS (DCI) m/z: 229 (M+H)$^+$, 246 (M+NH$_4$)$^+$; Anal. Calcd for $C_{14}H_{16}N_2O.2.2$ HCl.1.1 $H_2O$: C, 51.21; H, 6.26; N, 8.53. Found: C, 51.27; H, 6.05; N, 8.31.

EXAMPLE 19

Preparation of exo-2-(Hexahydro-1H-3-(S)-pyrrolizinyl)furo[3,2-b]pyridine dihydrochloride

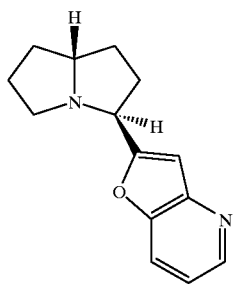

Following the procedures of Example 18e above, substituting the exo-hexahydro-1H-3-(S)-ethynylpyrrolizine compound from Example 18d above for the endo-(R) compound of step 18e, the title compound was prepared. $[\alpha]^{23}_D$-21.28 (c 0.10, MeOH); $^1H$ NMR ($CDCl_3$, 300 MHz) δ 1.78–2.00 (m, 2H), 2.06–2.24 (m, 2H), 2.36–2.52 (m, 2H), 2.53–2.78 (m, 2H), 2.90–3.03 (m, 1H), 3.21–3.30 (m, 1H), 4.42–4.53 (m, 1H), 5.17–5.29 (m, 1H), 7.61 (s, 1H), 7.89 (dd, J=9.0 Hz, J=11.0 Hz, 1H), 8.62 (d, J=12.0 Hz, 1H), 8.27–8.38 (m, 1H); MS (DCI) m/z: 229 (M+H)$^+$, 246 (M+NH$_4$)$^+$; Anal. Calcd for $C_{14}H_{16}N_2O.2.40$ HCl.0.50 $H_2O$: C, 51.87; H, 6.02; N, 8.49. Found: C, 51.87; H, 5.71; N, 8.49.

EXAMPLE 20

Preparation of exo-2-(Hexahydro-1H-3-(R)-pyrrolizinyl)furo[3,2-b]pyridine dihydrochloride

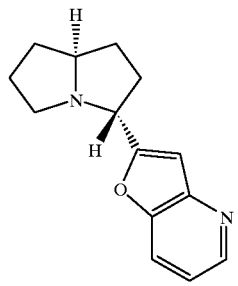

Following the procedures of Example 18, substituting (S)-prolinal for the (R)-starting material of step 18a therein, and carrying the reactions forward as in steps 18b, c, and d, then separating the exo-(R)- and endo-(S)-isomers and carrying the exo-(R)-compound forward according to the procedures of step 18e, the title compound was prepared. The MS and NMR data were similar to the compound of Example 18e. $[\alpha]^{23}_D$-24.68 (c 0.16, MeOH).

EXAMPLE 21

Preparation of endo-2-(Hexahydro-1H-3-(S)-pyrrolizinyl)furo[3,2-b]pyridine dihydrochloride

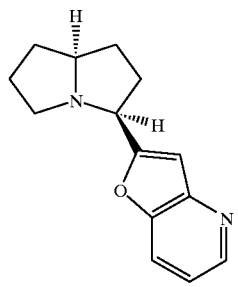

Following the procedures of Example 18e above, substituting the endo-hexahydro 1H-3-(S)-ethynylpyrrolizine compound from Example 20 above for the endo-(R) compound of step 18e, the title compound was prepared. The MS and NMR data were similar to the compound of Example 18e. $[\alpha]^{\leqq}_D$+31.01 (c 0.21, MeOH).

EXAMPLE 22

Preparation of 1-Pyrrolidinylmethyl-(2-furo[3,2-b] pyridine)

To DMF (20.0 mL) in a flask purged with nitrogen were added 2-iodo-3-hydroxypyridine (18.60 mmol, 4.11 g)(Aldrich), bis(triphenylphosphine)-palladium(II) chloride (0.80 mmol, 0.544 g), copper(I) iodide (3.10 mmol, 0.590 g), and triethylamine (18.60 mmol, 2.59 g), and the mixture was stirred for one hour at room temperature. To this solution was then added N-(3-propynylpyrrolidine (15.50 mmol, 1.68 g, prepared according to Biehl and DiPierro, *J. Am. Chem. Soc.*, 80, 4609–4614, 1958), in DMF (10.0 mL), and the mixture was heated at 60° C. for 16 hours. The mixture was cooled, poured into 4 N HCl (100 mL) and extracted with $CH_2Cl_2$. The aqueous phase was then basified with 15% NaOH and extracted with $CH_2Cl_2$. The extract was dried over $MgSO_4$ and concentrated in vacuo. The residue was purified by chromatography, eluting with 10% $MeOH/CH_2Cl_2$ to give the title compound in 72% yield: $^1H$ NMR (300 MHz): δ 2.25 (bs, 4H), 3.64 (bs, 4H), 4.88 (s, 2H), 7.57 (s, 1H), 7.90 (dd, J=5.37, 13.67 Hz, 1H), 8.56 (d, J=8.30 Hz, 1H), 8.80 (d, J=5.86 Hz, 1H). MS (DCI): $(M+H)^+$, 203; $(M+NH_4)^+$, 220. Anal. Calcd for $C_{12}H_{14}N_2O$.2.0 HCl.0.1 $H_2O$: C, 52.03; H, 5.89; N,10.11. Found C, 51.72; H, 6.12; N, 10.05

EXAMPLE 23

Preparation of 5-Chloro-2-(hexahydro-1H-7a-pyrrolizinyl)furo[3,2-b]pyridine hydrochloride 23a. 5-Chloro-2-(hexahydro-1H-7a-pyrrolizinyl)furo[3,2-b]pyridine 7a-Ethynyl-hexahydro-1H-pyrrolizine from Example 15b (225 mg, 1.66 mol, 6-chloro-2-iodo-3-pyridinol (509 mg, 2.0 mmol), copper(I) iodide (60 mg, 0.30 mmol), bis (triphenylphosphine)palladium(II) chloride (58 mg, 0.08 mmol) and triethylamine (0.280 mL, 2.0 mmol) were combined in a similar fashion as that described in Example 15c. The crude product was chromatographed (silica gel; $CHCl_3$/MeOH, 97.5:2.5) to afford a waxy tan solid (335 mg, 77%): $^1H$ NMR ($CDCl_3$, 300 MHz) δ 1.88–1.97 (m, 6H), 2.21–2.33 (m, 2H), 2.67–2.79 (m, 2H), 3.19–3.26 (m, 2H), 6.70 (s, 1H), 7.14 (d, J=8.5 Hz, 1H), 7.61 (d, J=8.5 Hz, 1H); MS ($CI/NH_3$) m/z: 263 $(M+H)^+$.

23b. 5-Chloro-2-(hexahydro-1H-7a-p yrrolizinyl)furo[3,2-b]pyridine hydrochloride The compound from step 23a (325 mg, 1.24 mmol) was dissolved in $CH_2Cl_2$ (10 mL) and a saturated solution of HCl in $Et_2O$ was added dropwise. The solvent was removed and the product recrystallized from $MeOH/Et_2O$ to afford a white solid (223 mg, 58%): mp 233–235° C.; $^1H$ NMR ($D_2O$, 300 MHz) δ 2.32–2.45 (m, 6H), 2.75–2.83 (m, 2H), 3.31–3.43 (m, 2H), 3.75–3.83 (m, 2H), 7.23 (s, 1H), 7.49 (d, J=9 Hz, 1H), 8.01 (d, J=9 Hz, 1H); MS ($CI/NH_3$) m/z: 263 $(M+H)^+$; Anal. Calcd for $C_{14}H_{15}ClN_2O$.1.2 HCl: C, 54.86; H, 5.33; N, 9.14. Found: C, 54.61; H, 5.36; N, 8.98.

EXAMPLE 24

Preparation of 2-(Hexahydro-1H-7a-pyrrolizinyl)thieno[3,2-b]pyridine hydrochloride 24a. 2-(Hexahydro-1H-7a-parrolizinyl)thieno[3,2-b]pyridine Thieno[3,2-b]pyridine (200 mg, 1.48 mmol) prepared according to S. Gronowitz et al., *Acta Chemica Scandinavica* B 1975, 29: 233–238 was dissolved in THF (6 mL) and nBuLi in hexanes (2.5 M, 0.6 mL, 1.5 mmol) was added at 0° C. After 10 minutes of stirring, 1,2,3,5,6,7-hexahydropyrrolizinium perchlorate from Example 15a (155 mg, 0.74 mmol) was added. The slurry was allowed to gradually warm to ambient temperature and stir for an additional two hours. The reaction mixture was partitioned between 2 N aqueous HCl and $Et_2O$. The phases were separated and the aqueous phase was basified with 15% NaOH solution and then extracted with $CH_2Cl_2$ (3×). The $CH_2Cl_2$ extracts were combined, dried ($MgSO_4$) and concentrated. The residue was chromatographed (silica gel; $CHCl_3$/MeOH, 100:0 to 99:1) to afford a yellow solid (115 mg, 63%): mp 94–96° C.; $^1H$ NMR ($CDCl_3$, 300 MHz) δ 1.80–1.96 (m, 4H), 2.00–2.09 (m, 2H), 2.18–2.26 (m, 2H), 2.64–2.72 (m, 2H), 3.23–3.30 (m, 2H), 7.13 (dd, J=8, 4 Hz, 1H), 7.23 (s, 1H), 8.05 (dd, J=8, 1.5 Hz, 1H), 8.58 (dd, J=4, 1.5 Hz, 1H); MS ($CI/NH_3$) m/z: 245 $(M+H)^+$.

24b. 2-(Hexahydro-1H-7a-pyrrolizinyl)thieno[3,2-b]pyridine hydrochloride

The compound from step 24a (104 mg, 0.43 mmol) was dissolved in $CH_2Cl_2$ (3 mL) and a saturated solution of HCl in $Et_2O$ was added dropwise. The solvent was removed and the product was dried in vacuo to afford a hygroscopic yellow solid (124 mg, 93%): $^1H$ NMR ($D_2O$, 300 MHz) δ 2.30–2.48 (m, 4H), 2.51–2.60 (m, 2H), 2.77–2.86 (m, 2H), 3.36–3.44 (m, 2H), 3.79–3.88 (m, 2H), 7.67 (dd, J=8, 5 Hz, 1H), 7.84 (s, 1H), 8.70 (dd, J=8, 1 Hz, 1H), 8.75 (dd, J=5, 1 Hz, 1H); MS ($CI/NH_3$) m/z: 245 $(M+H)^+$; Anal. Calcd for $C_{14}H_{16}N_2S$.1.8 HCl: C, 54.25; H, 5.79; N, 9.04. Found: C, 54.25; H, 5.81; N, 8.75.

EXAMPLE 25

Preparation of 5,6-Dichloro-2-(2-(S)-pyrrolidinyl) furo [3,2-b]pyridine hydrochloride 5,6-dichloro-2-(1-t-butyloxycarbonyl-2-(S)-pyrrolidinyl) furo[3,2-b]pyridine 5,6-Dichloro-2-iodo-3-pyridinol (750 mg, 2.6 mmol) (prepared by treatment of 5,6-dichloro-3-hydroxypyridine (Koch & Schnatterer, Synthesis 1990, 499) with $I_2$ (ibid, p. 497), copper(I) iodide (89 mg, 0.47 mmol), bis (triphenylphosphine)palladium(II) chloride (91 mg, 0.13 mmol) and triethylamine (433 mL, 3.1 mmol) were combined in DMF (3.0 mL) and allowed to stir for 1 hour. 1-t-Butyloxycarbonyl-2-(S)-ethynylpyrrolidine (610 mg, 3.1 mmol) in DMF (1 mL) was added and the reaction mixture was heated to 60° C. for 16 hours. After cooling to ambient temperature, the reaction mixture was poured over $Et_2O$/saturated $K_2CO_3$ solution and the phases separated. The organic phase was washed with brine:water (1:1) (4×), dried ($MgSO_4$), concentrated and chromatographed (silica gel; EtOAc/hexane, 1:6) to afford an amber oil (408 mg, 44%): $^1H$ NMR ($CDCl_3$, 300 MHz) δ 1.32 and 1.45 (two br s, 9H), 1.95–2.40 (m, 4H), 3.45–3.74 (m, 2H), 5.02 (m, 1H), 6.62 (s, 1H), 7.81 (s, 1H); MS ($CI/NH_3$) m/z: 357 $(M+H)^+$.

25b. 5,6-Dichloro-2-(2-(S)-pyrrolidinyl)furo[3,2-b]pyridine

The compound from step 25a (400 mg, 1.12 mmol) was dissolved in $CH_2Cl_2$ (3 mL) and TFA (3 mL) was added at ambient temperature. After stirring for 1 hour, the solvent was removed and the residue was dissolved in $CH_2Cl_2$ and washed with saturated $K_2CO_3$ solution, dried ($MgSO_4$) and concentrated. The crude product was chromatographed (silica gel; $CHCl_3$/MeOH, 98:2) to afford a solid (206 mg, 71%): mp 98–100° C.; $^1H$ NMR ($CDCl_3$, 300 MHz) δ 1.81–2.05 (m, 3H), 2.22 (m, 1H), 3.04–3.20 (m, 2H), 4.40 (m, 1H), 6.70 (s, 1H), 7.80 (s, 1H); MS ($CI/NH_3$) m/z: 257 $(M+H)^+$.

25c. 5,6-Dichloro-2-(2-(S)-pyrrolidinyl)furo[3,2-b]pyridine hydrochloride

The compound from step 25b above (54 mg, 0.21 mmol) was slurried in $Et_2O$ and a saturated solution of HCl in $Et_2O$ was added dropwise. The solvent was removed and the product was recrystallized from $MeOH/Et_2O$ to afford a white solid (48 mg, 78%): $[\alpha]_D^{20}$+5.3 (c 0.51, MeOH); $^1H$ NMR ($D_2O$, 300 MHz) δ 2.18–2.65 (m, 4H), 3.51–3.56 (m, 2H), 5.05 (dd, J=8, 8 Hz, 1H), 7.16 (d, J=1 Hz, 1H), 8.24 (d, J=1 Hz, 1H); MS (CI/NH$_3$) m/z: 257 (M+H)$^+$; Anal. Calcd for C$_{11}$H$_{10}$Cl$_2$N$_2$O.HCl: C, 45.00; H, 3.78; N, 9.54. Found: C, 45.08; H, 3.59; N, 9.40.

EXAMPLE 26

Preparation of 5,6-Dichloro-2-(1-methyl-2-(S)-pyrrolidinyl)furo[3,2-b]pyridine hydrochloride 26a. 5,6-Dichloro-2-(1-methyl-2-(S)-pyrrolidinyl)furo[3,2-b]pyridine The amine from Example 25b (145 mg, 0.57 mmol) was dissolved in an aqueous solution of 37% formaldehyde (excess) and 88% formic acid (excess). The aqueous mixture was heated to 90° C. for 1.5 hours and then allowed to cool to ambient temperature. The reaction mixture was washed with Et$_2$O, basified with 15% NaOH solution and extracted with CH$_2$Cl$_2$ (3×). The organic phases were combined, dried (MgSO$_4$), concentrated and chromatographed (silica gel; CHCl$_3$/MeOH, 98:2) to afford a white solid (97 mg, 62%): mp 58–60° C.; $^1$H NMR (CDCl$_3$, 300 MHz) δ 1.89 (m, 1H), 2.00–2.17 (m, 2H), 2.24 (m, 1H), 2.33 (s, 3H), 2.39 (m, 1H), 3.26 (m, 1H), 3.43 (m, 1H), 6.74 (s, 1H), 7.83 (s, 1H); MS (CI/NH$_3$) m/z: 271 (M+H)$^+$.

26b. 5,6-Dichloro-2-(1-methyl-2-(S)-pyrrolidinyl)furo[3,2-b]pyridine hydrochloride The compound from step 26a (92 mg, 0.34 mmol) was slurried in Et$_2$O and a saturated solution of HCl in Et$_2$O was added dropwise. The solvent was removed and the product was recrystallized from MeOH/Et$_2$O to afford a white solid (70 mg, 67%): mp 249–251° C.; $^1$H NMR (D$_2$O, 300 MHz) δ 2.27–2.37 (m, 2H), 2.47–2.71 (m, 2H), 2.93 (s, 3H), 3.38 (m, 1H), 3.79 (m, 1H), 4.82 (m, partially buried under H$_2$O peak, 1H), 7.27 (s, 1H), 8.26 (s, 1H); MS (CI/NH$_3$) m/z: 271 (M+H)$^+$; Anal. Calcd for C$_{12}$H$_{12}$Cl$_2$N$_2$O.1.2 HCl: C, 45.77; H, 4.23; N, 8.82; Found: C, 45.61; H, 4.36; N, 8.90.

EXAMPLE 27

Preparation of 2-(Hexahydro-1H-7a-pyrrolizinyl)-4-methylthieno[3,2-b]pyridine dihydrochloride 27a. 2-(Hexahydro-1H-7a-pyrrolizinyl)-4-methylthieno[3,2-b]pyridine 5-Methylthieno[3,2-b]pyridine (285 mg, 1.91 mmol, prepared according to Gronowitz et al., *Acta Chemica Scandinavica B*, 29:233–238 (1975)), diisopropylamine (270 uL, 1.91 mmol) and nBuLi (2.5 M in hexanes, 765 uL, 1.91 mmol) were combined in THF (8 mL). After 20 minutes of stirring, 1,2,3,5,6,7-hexahydro-pyrrolizinium perchlorate from Example 15a (200 mg, 0.95 mmol) was added. The mixture was allowed to warm to ambient temperature and 2 N aqueous HCl was added. The reaction mixture was washed with Et$_2$O and the aqueous phase was basified with 15% NaOH solution and extracted with CH$_2$Cl$_2$ (3×). The organic phases were combined, dried (MgSO$_4$), concentrated and chromatographed (silica gel; CHCl$_3$/MeOH, 99:1) to afford a solid (79 mg, 32%): $^1$H NMR (CDCl$_3$, 300 MHz) δ 1.80–1.94 (m, 4H), 1.98–2.07 (m, 2H), 2.16–2.24 (m, 2H), 2.64 (s, 3H), 2.64–2.71 (m, 2H), 3.22–3.28 (m, 2H), 7.02 (d, J=8 Hz, 1H), 7.16 (s, 1H), 7.92 (d, J=8 Hz, 1H); MS (CI/NH$_3$) m/z: 259 (M+H)$^+$.

27b. 2-(Hexahydro-1H-7a-pyrrolizinyl)-4-methylthieno[3,2-b]pyridine dihydrochloride The compound from step 27a (73 mg, 0.28 mmol) was dissolved in CH$_2$Cl$_2$ and treated with a saturated solution of HCl in Et$_2$O to afford a hygroscopic foam-like solid (100 mg, quantitative): mp 233–235° C.; $^1$H NMR (D$_2$O, 300 MHz) δ 2.28–2.49 (m, 4H), 2.55–2.64 (m, 2H), 2.77–2.86 (m, 2H), 2.89 (s, 3H), 3.38–3.47 (m, 2H), 3.82–3.90 (m, 2H), 7.78 (d, J=8.5 Hz, 1H), 7.90 (s, 1H), 8.90 (d, J=8.5 Hz, 1H); MS (CI/NH$_3$) m/z: 259 (M+H)$^+$; Anal. Calcd for C$_{15}$H$_{18}$N$_2$S.1.3 HCl.0.9 H$_2$O: C, 50.26; H, 6.21; N, 7.81. Found: C, 50.68; H, 6.40; N, 7.41.

EXAMPLE 28

Preparation of 5-bromo-2-(2-(S)-parrolidinvy)-furo[3,2-b]pyridine hydrochloride 28a. 5-amino-2-bromopyridine A mixture of 2-bromo-5-nitropyridine (30.75 g, 151.5 mmol), water (250 mL), and acetic acid (110 mL) was heated to 45° C. Iron powder (24.5 g, 439 mmol) was added at a rate which kept the temperature below 53° C., then the mixture was stirred at 48° C.±5° C. The mixture was cooled to room temperature and filtered through diatomaceous earth. The filter cake was washed with EtOAc, and the aqueous mixture was extracted with EtOAc. The combined organic fractions were washed with saturated Na$_2$CO$_3$ and brine, dried over MgSO$_4$, and the solvent was removed in vacuo. The residue was chromatographed on silica gel, eluting with 100:0 to 50:50 hexane:EtOAc to give 20.4 g of the title compound: $^1$H NMR (CDCl$_3$ 300 MHz) δ 6.86–6.90 (dd, 1H, J=8.5, 2.4 Hz) 7.21–7.23 (d, 1H, J=8.2 Hz) 7.85–7.86 (d, 1H, J=3 Hz); MS m/z: 173 (M+H)$^+$, 190 (M+NH$_4$)$^+$.

28b. 5-acetoxy-2-bromopyridine

To 25.6 mL of boron trifluoride etherate (208 mmol, Aldrich) cooled to −15° C. under N$_2$ was added 18 g (104 mmol) of 5-amino-2-bromopyridine (from step 28a above) dissolved in 35 mL of DME. Then tert-butyl nitrite (14.7 mL, 125 mmol, Aldrich) was added at a rate which kept the temperature below 0° C. DME (65 mL) and CH$_2$Cl$_2$ (60 mL) were then added. After 10 minutes at −10° C. the mixture was warmed to 5° C. and stirred for 30 min. Pentane (400 mL) was then added to the reaction mixture, the solid was collected by suction filtration, washed with cold ether, air dried, and dissolved in 125 mL acetic anhydride. The resulting solution was heated to 100° C.±5° C. for 1 hour. The solvent was removed in vacuro, and the residue was suspended in saturated aqueous Na$_2$CO$_3$, and extracted with ethyl ether. The ether solution was dried over MgSO$_4$, the solvent was removed in vacuo, and the residue was chromatographed on silica gel, eluting with 100:0 to 60:40 hexane:EtOAc to give 13.6 g of the title compound: $^1$H NMR (CDCl$_3$ 300 MHz) δ 2.35 (s, 3H) 7.36–7.39 (dd, 1H), 7.49–7.52 (d, 1H), 8.19–8.21 (d, 1H) MS m/z: 216 (M+H)$^+$, 233 (M+NH$_4$)$^+$.

28c. 2-bromo-5-hydroxypyridine

5-Acetoxy-2-bromopyridine (12.8 g, 60 mmol, from step 28b) was dissolved in 15% aqueous NaOH (50 mL) at 0° C., and the solution was warmed to room temperature and stirred for 60 minutes. After complete consumption of the starting material the solution was neutralized by addition of 1 N HCl. The aqueous mixture was extracted with EtOAc (3×200 mL). The organic extracts were washed with brine (4×50 mL), water (2×50 mL), dried (MgSO$_4$), and the solvent was evaporated to yield 9.8 g of the title compound: $^1$H NMR (CDCl$_3$, 300 MHz) δ 7.12–7.16 (dd, 1H, J=3.2 Hz), 7.36–7.39 (d, 1H, J=8.5Hz), 8.04–8.05 (d, 1H, J=2.4 Hz); MS m/z: 174 (M+H)$^+$.

28d. 6-bromo-2-iodo-3-pyridinol

A 4.125 g sample of 2-bromo-5-hydroxypyridine (from step 28c) and 5.28 g of Na$_2$CO$_3$ were dissolved in 75 mL of water. To this solution was added 6.02 g of I$_2$, and the mixture was stirred until the iodine color disappeared. The reaction mixture was then adjusted to pH 5, and extracted with EtOAc. The extract was dried over $MgSO_4$, and the solvent was removed. The residue was chromatographed on silica gel, eluting with 97:3 $CHCl_3$:MeOH to give 4.3 g of the title compound: $^1H$ NMR ($CDCl_3$, 300 MHz) δ 7.08–7.11 (d, 1H, J=8.5 Hz), 7.29–7.32 (d, 1H, J=8.5 Hz); MS m/z: 300 $(M+H)^+$, 317 $(M+NH_4)^+$.

28e 2-(1-BOC-2-(S)-pyrrolidinyl)-5-bromofuro[3,2-b]pyridine

A 1.84 g (6.10 mmol) sample of 6-bromo-2-iodo-3-pyridinol, from step 28d above, was dissolved in 10 mL of DMF, and $(Ph_3P)_2PdCl_2$ (0.30 g, 0.4 mmol), CuI (0.3 g, 1.6 mmol) and triethylamine (1.2 mL, 8.5 mmol) were added. The mixture was stirred under $N_2$ at room temperature for 1 hour, then 1.3 g (6.7 mmol) of 1-BOC-2-(S)-ethynylpyrrolidine, from Example 1c above, dissolved in 5 mL of DMF, was added carefully. The reaction was stirred at 80° C. for 16 hours, then cooled to room temperature. The reaction mixture was diluted with ether, then washed with 50% brine, and the extract was dried over $MgSO_4$. The solvent was removed, and the residue was chromatographed on silica gel, eluting with 100:0 to 60:40 hexane:EtOAc to give 1.4 g of title compound: $^1H$ NMR ($CDCl_3$, 300 MHz) δ 1.31(s, 9H), 1.89–2.06 (m, 3H), 2.27–2.34 (m, 1H), 3.43–3.5 (m, 2H), 4.96–5.0 (m, 1H), 6.72 (s, 1H), 7.38–7.41 (d, 1H, J=8.6 Hz), 7.83–7.86 (d, 1H, J=8.6 Hz); MS m/z: 367 $(M+H)^+$.

28f. 2-(2-(S)-pyrrolidinyl)-5-bromofuro[3,2-b]pybidine hydrochloride

To a solution of the product from step 28e above (1.2 g) in 10 mL of $CH_2Cl_2$ at 0° C. was added 10 mL of TFA. The reaction mixture was stirred for 1 hour, the mixture was poured into saturated $K_2CO_3$, and the aqueous solution was extracted with $CH_2Cl_2$. The organic extract was dried over $MgSO_4$, and the solvent was removed. The residue was chromatographed on silica gel, eluting with 99:1 to 95:5 $CHCl_3$:MeOH. The residue was converted to the salt by treatment with HCl/ether to give 0.6 g of the title compound: $^1H$ NMR ($D_2O$, 300 MHz) δ 2.30–2.63 (m, 4H), 3.51–3.56 (m, 2H), 5.02–5.07 (t, 1H, J=7.7 Hz), 7.15 (s, 1H,), 7.61–7.64 (d, 1H, J=8.8 Hz), 7.91–7.95 (d, 1H, J=8.8 Hz); MS m/z: 267 $(M+H)^+$, 282 $(M+NH_4)^+$; Anal. Calcd for $C_{11}H_{11}N_2OCl.1.0$ HCl: C, 43.52; H, 3.98 N, 9.23. Found: C, 43.53; H, 4.08; N, 9.13.

28g 2-(1-methyl-2-(S)-pyrrolidinyl)-5-Br-furo[3,2-b]pyridine dihydrochloride

A 300 mg sample of the compound from step 28f above was dissolved in an aqueous solution of 37% formaldehyde (4 mL) and 88% formic acid (2 mL) and heated at reflux for 1 hour. The solution was cooled, diluted with water, and adjusted to pH 10 with $K_2CO_3$. The mixture was extracted with $CH_2Cl_2$, and the extract was dried and concentrated. The residue was purified by chromatography on silica gel, eluting with 100:0 to 97:3 $CHCl_3$:MeOH. The product was dissolved in ethanol at ambient temperature and a solution of hydrochloric acid in $Et_2O$ was added dropwise. The resultant white precipitate was then collected by evaporation of solvent and triturated with three portions of $Et_2O$ to give the title compound (163 mg, 43%): $^1H$ NMR ($D_2O$, 300 MHz) δ 2.28–2.39 (m 2H), 2.49–2.72 (m, 2H), 2.95 (s, 3H), 3.38 (m, 1H), 3.80 (m, 1H), 4.85 (m, 1H), 7.27 (s, 1H), 7.96 (d, 1H, J=1.02 Hz), 7.96 (d, 1H, J=1.02 Hz); MS m/z: 281 $(M+H)^+$; Anal. Calcd for $C_{12}H_{13}N_2OBr.1.0$ HCl: C, 45.38; H, 4.44 N, 8.82. Found: C, 45.11; H, 4.17; N, 8.52.

EXAMPLE 29

Preparation of 5-methyl-2-(2-(R)-pyrrolidinyl)-furo[3,2-b]pyridine hydrochloride The title compound was prepared from 1-Boc-2(R)-ethynylpyrrolidine according to the procedures of Example 5 above: $[\alpha]_D^{\leq}$+16.5° (c 1.0, MeOH); Anal. Calcd for $C_{12}H_{14}N_2O.2.0$ HCl.0.2 $H_2O.0.2$ ethanol: C, 51.39; H, 6.19; N, 9.67. Found: C, 51.63; H, 6.49; N, 9.33.

EXAMPLE 30

Preparation of 5-methyl-2-(1-methyl-2-(R)-pyrrolidinyl)-furo[3,2-b]pyridine dihydrochloride The title compound was prepared from 1-Boc-2(R)-ethynylpyrrolidine according to the procedures of Example 6 above: Anal. Calcd for $C_{13}H_{16}N_2O.2.0$ HCl.0.4 $H_2O$: C, 52.68; H, 6.39; N, 9.145. Found: C, 52.70; H, 6.27; N, 9.32.

EXAMPLE 31

Preparation of 6-chloro-2-(2-(R)-pyrrolidinyl)-furo[3,2-b]pyridine hydrochloride The title compound was prepared from 1-Boc-2(R)-ethynylpyrrolidine according to the procedures of Example 13 above: Anal. Calcd for $C_{11}H_{11}N_2OCl.1.0$ HCl: C, 50.99; H, 4.67 N, 10.81. Found: C, 50.91; H, 4.75; N, 10.86.

EXAMPLE 32

Preparation of 5-chloro-2-(1-methyl-2-(R)-pyrrolidinyl)-furo[3,2-b]pyridine hydrochloride The title compound was prepared from 1-Boc-2(R)-ethynylpyrrolidine according to the procedures of Example 12 above: Anal. Calcd for $C_{12}H_{13}N_2OCl.1.8$ HCl: C, 47.67; H, 4.93; N, 9.27. Found: C, 47.49; H, 5.08; N, 8.97.

EXAMPLE 33

Preparation of 5-bromo-2-(2-(R)-pyrrolidinyl)-furo[3,2-b]pyridine hydrochloride

The title compound was prepared from 1-Boc-2(R)-ethynylpyrrolidine according to the procedures of Examples 28 above: Anal. Calcd for $C_{11}H_{11}N_2OCl.10$ HCl: C, 43.52; H, 3.98 N, 9.23. Found: C, 43.40; H, 4.05; N, 8.98

EXAMPLE 34

Preparation of 2-(2-(R)-pyrrolidinyl)furo[2,3-c]pyridine dihydrochloride

The title compound was prepared from 1-Boc-2(R)-ethynylpyrrolidine according to the procedures of Example 9 above: Anal. Calcd for $C_{11}H_{12}N_2O.2$ HCl: C, 50.58; H, 5.40; N, 10.73. Found: C, 50.38; H, 5.37; N, 10.51.

EXAMPLE 35

Preparation of 5-chloro-2-(2-(R)-pyrrolidinyl)-furo[3,2-b]pyridine hydrochloride The title compound was prepared from 1-Boc-2(R)-ethynylpyrrolidine according to the procedures of Example 11 above: Anal. Calcd for $C_{11}H_{11}N_2OCl.2$ HCl: C, 50.99; H, 4.67; N, 10.81. Found: C, 50.90; H, 4.75; N, 10.86.

EXAMPLE 36

Preparation of 2-(2-(S)-pyrrolidinyl)furo[2,3-b]pyridine hydrochloride 36a. 2-(1-BOC-2-(S)-pyrrolidinyl)furo[2.3-b]pyridine The compound from step 13b above (0.23 g, 0.7 mmol), triethylamine (0.2 mL, 1.4 mmol), and 10% Pd on C (Aldrich, 50 mg) were stirred in 20 mL of EtOH under $H_2$ (1 atm) for 4 hours. The mixture was filtered, concentrated and the crude product was purified by flash chromatography on silica gel eluting with hexane/EtOAc (9:1 to 7:3) to provide 140 mg (68%) of the title compound: $^1$H NMR (DMSO, 120° C., 300 MHz) δ 1.33 (s, 9H), 1.93–2.10 (m, 3H), 2.32 (m, 1H), 3.46–3.53 (m, 2H), 5.0 (m, 1H), 7.28 (dd, 1H, J=6.7, 2.8 Hz), 8.0 (dd, 1H, J=6.0, 1.7 Hz), 8.22 (dd, J=4.0, 1.4 1H); MS m/z: 289 (M+H)$^+$, 306 (M+NH$_4$)$^+$.

36b. 2-(2-(S)-pyrrolidinyl)furo[2,3-b]pyrydine hydrochloride

The compound from step 36a above (0.13 g, 0.45 mmol) was dissolved in 3 mL of $CH_2Cl_2$ at 0° C. and 3 mL of TFA was added. The reaction mixture was stirred for 1 hour, poured into saturated aqueous $K_2CO_3$, and extracted with $CH_2Cl_2$. The organic extract was dried over $MgO_4$, and the solvent was removed. The residue was chromatographed on silica gel, eluting with 99:1 to 95:5 CHCl$_3$:MeOH. The residue was treated with a solution of HCl in Et$_2$O to give 40 mg (42%) of title compound: $^1$H NMR (D$_2$O, 300 MHz) δ 2.15–2.62 (m, 4H), 3.48–3.75 (m, 2H), 5.01 (t, 1H, J=7.8 Hz), 7.11 (s, 1H,), 7,43 (m, 1H, J, 8.18 (dd, 1H, J=7.8, 1.7 Hz) 8.33 (dd, 1H, J=7.8, 4.1, 2.4 Hz). MS m/z: 189 (M+H)$^+$, 206 (M+NH$_4$)$^+$; Anal. Calcd for $C_{11}H_{12}N_2O.1.4$ HCl: C, 55.22; H, 5.64 N, 11.79. Found: C, 55.11; H, 5.41 N, 11.59

EXAMPLE 37

Preparation of 2-(1-methyl-2-(S)-pyrrolidinyl)furo [3,2-c]pyridine dihydrochloride 37a. 4-hydroxy-3-iodopyridine To a solution of 4-hydroxypyridine (4.76 g, 50.1 mmol) and Na$_2$CO$_3$ (10.8 g, 100 mmol) in 200 mL of water was added I$_2$ (12.7 g, 50.1 mmol). The reaction mixture was stirred for 14 h then adjusted to pH 5 with concentrated HCl. The resulting solids were suspended in boiling ethanol and hot filtered. The solvent was removed and the resulting solids recrystallized from MeOH to afford 5.1 g (46%) of the title compound: $^1$H NMR (DMSO-d$_6$) d 8.26 (br s, 1H), 7.70 (s, 1H), 7.69 (d, J=7 Hz, 1H), 6.14 (d, J=7 Hz, 1H); MS (DCI/NH$_3$) m/z: 222 (M+H)$^+$, 239 (M+NH$_4$)$^+$.

37b. 2-(1-BOC-2-(S)-pyrrolidinyl)furo[3,2-c]pyridine

A sample of the compound from step 1c above (1.95 g 12 mmol) was dissolved in 15 mL of DMF, and (Ph$_3$P)$_2$PdCl$_2$ (0.6 mmol), CuI (0.74 mmol) and triethylamine (14.3 mmol) were added. The mixture was stirred at room temperature for 1 hour, then 2.65 g (12 mmol) of 4-hydroxy-3-iodopyridine from step 37a was added. The reaction mixture was stirred at 60° C. for 16 hours. The solution was cooled, diluted with toluene, and the volatiles removed in vacuo. The residue was dissolved in 1 N aqueous HCl, and this solution was washed with ether. The acidic solution was adjusted to a pH 10 with $K_2CO_3$, and this solution was extracted with $CH_2Cl_2$. The $CH_2Cl_2$ extract was washed with 20% NaOH, dried over $MgO_4$, and evaporated. The residue was chromatographed on silica gel, eluting with 100:0 to 95:5 hexane:EtOAc to give 1.64 g (59%) of title compound: $^1$H NMR (CDCl$_3$, 300 MHz) δ 1.30–1.50 (m, 9H), 1.90–2.20 (m, 4H), 2.95–3.15 (m, 2H), 5.05 (m, 1H), 6.55 (br s, 1H) 7.38 (d, 1H, J=8 Hz), 8.45 (br s, 1H), 8.85 (br s, 1H); MS m/z: 289 (M+H)$^+$.

37c 2-(1-methyl-2-(S)-pyrrolidinyl)furo[3,2-c]pyridine dihydrochloride

A 580 mg sample of the compound from step 37b above was dissolved in an aqueous solution of 37% formaldehyde (8 mL) and 88% formic acid (4 mL) and heated at reflux for 1 hour. The solution was cooled, diluted with water, and adjusted to pH 10 with $K_2CO_3$. The mixture was extracted with $CH_2Cl_2$, and the extract dried and concentrated. The residue was purified by chromatography on silica gel, eluting with 100:0 to 97:3 CHCl$_3$:MeOH. The product was dissolved in ethanol at ambient temperature and a solution of hydrochloric acid in Et$_2$O was added dropwise. The resultant white precipitate was then collected by evaporation of solvent and triturated with three portions of Et$_2$O to give the title compound (552 mg, 70%): $^1$H NMR (D$_2$O, 300 MHz) δ 2.20 (br s 2H), 2.38–2.57 (m, 3H), 2.85 (br s, 3H), 3.26 (br s, 1H), 3. 85 (br s, 1H), 7.44 (s, 1H), 7.98 (d, 1H, J=6.8 Hz), 8.56 (d, 1H, J=2.3 Hz), 9.10 (s, 1H, ); MS m/z; 203 (M+H)$^+$; Anal. Calcd for $C_{12}H_{14}N_2O.2.0$ HCl.0.2 H$_2$O.0.2 ethanol: C, 51.72; H, 6.16 N, 9.73. Found: C, 51.86; H, 6.13; N, 9.54.

EXAMPLE 38

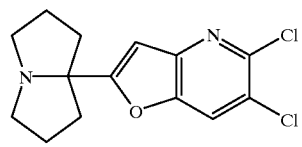

Preparation of 2-(Hexahydro-1H-7a-pyrrolizinyl)-5, 6-dichlorofuro[3,2-b]pyridine hydrochloride 38a. 5,6-Dichloro-2-(hexahydro-1H-7a-pyrrolizinyl)furo [3,2-b]pyridine 2,3-Dichloro-6-iodo-5-pyridinol (163 mg, 0.56 mmol) from example 25a, copper(I) iodide (20 mg, 0.10 mmol), bis (triphenylphosphine)palladium(II) chloride (20 mg, 0.030 mmol) and triethylamine (176 mL, 0.67 mmol) were combined and allowed to stir for 1 hour at ambient temperature. 7a-ethynyl-hexahydro-1H-pyrrolizine (91 mg, 0.67 mmol) in DMF (1.0 mL) was added to the reaction mixture which was then heated to 60° C. for 18 hours. After cooling to ambient temperature, 2 N aqueous HCl was added and the mixture was washed with Et$_2$O (2×), basified with 15% NaOH solution and extracted with $CH_2Cl_2$ (2×). The $CH_2Cl_2$ phases were combined, dried (MgSO$_4$), concentrated and the residue was chromatographed (silica gel; EtOAc/hexane, 1:3) to afford a white solid (116 mg, 70%): $^1$H NMR (CDCl$_3$, 300 MHz) δ 1.83–1.97 (m, 6H), 2.20–2.31 (m, 2H), 2.67–2.77 (m, 2H), 3.18–3.25 (m, 2H), 6.71 (s, 1H), 7.78 (s, 1H); MS (CI/NH$_3$) m/z: 297 (M+H)$^+$.

38b. 5,6-Dichloro-2-(hexahydro-1H-7a-pyrrolizinyl)furo[3, 2-b]pyridine hydrochloride 5,6-Dichloro-2-(hexahydro-1H-7a-pyrrolizinyl)furo[3,2-b]pyridine (108 mg, 0.36 mmol) was dissolved in Et$_2$O (7 mL) and a saturated solution of HCl in Et$_2$O was added dropwise. The solvent was removed and the product was recrystallized from MeOH/Et$_2$O to afford a white solid (88.5 mg, 74%): mp 229–231° C.; $^1$H NMR (D$_2$O, 300 MHz) δ 2.28–2.95 (m, 6H), 2.75–2.83 (m, 2H), 3.35–3.45 (m, 2H), 3.75–3.83 (m, 2H), 7.27 (s, 1H), 8.24 (s, 1H); MS (CI/NH$_3$) m/z: 297 (M+H)$^+$; Anal. Calcd for $C_{14}H_{14}Cl_2N_2O.1.5$ HCl.0.5 H$_2$O: C, 46.60; H, 4.61; N, 7.76. Found: C, 46.74; H, 5.00; N, 7.67.

EXAMPLE 39

Preparation of 5,6-Dichloro-2-(2-(R)-pyrrolidinyl) furo[3,2-b]pyridine hydrochloride 39a. 5,6-Dichloro-2-(1-t-butyloxycarbonyl-2-(R)-pyrrolidinyl)furo[3,2-b]pyridine 5,6-Dichloro-2-iodo-3-pyridinol (632 mg, 2.2 mmol), copper(I) iodide (75 mg, 0.40 mmol), bis (triphenylphosphine)palladium(II) chloride (77 mg, 0.11 mmol) and triethylamine (370 mL, 2.6 mmol) were combined in DMF (2.7 mL) and allowed to stir for 1 hour. 1-t-Butyloxycarbonyl-2-(R)-ethynylpyrrolidine (510 mg, 2.6 mmol) in DMF (1 mL) was added and the mixture was heated to 60° C. for 16 hours. After cooling to ambient temperature, the mixture was poured over Et$_2$O/saturated K$_2$CO$_3$ solution and the phases were separated. The organic phase was washed with brine:water (1:1) (4×), dried (MgSO$_4$) and concentrated. The residue was chromatographed (silica gel; EtOAc/hexane, 1:6) to afford an amber oil (365 mg, 46%): $^1$H NMR (CDCl$_3$, 300 MHz) δ 1.32 and 1.45 (two br s, 9H), 1.95–2.40 (m, 4H), 3.45–3.74 (m, 2H), 4.92–5.13 (m, 1H), 6.62 (s, 1H), 7.81 (s, 1H); MS (CI/NH$_3$) m/z: 357 (M+H)$^+$.

39b. 5,6-Dichloro-2-(2-(R)-pyrrolidinyl)furo[3,2-b]pyridine 5,6-Dichloro-2-(1-t-butyloxycarbonyl-2-(R)-pyrrolidinyl)furo[3,2-b]pyridine (355 mg, 1.0 mmol) was dissolved in CH$_2$Cl$_2$ (3 mL) and TFA (3 mL) was added at ambient temperature. After stirring for 1 hour, the solvent was removed and the residue was redissolved in CH$_2$Cl$_2$ and washed with saturated K$_2$CO$_3$ solution, dried (MgSO$_4$) and concentrated. The crude product was chromatographed (silica gel; CHCl$_3$/MeOH, 98:2) to afford a solid (220 mg, 87%): $^1$H NMR (CDCl$_3$, 300 MHz) δ 1.81–2.05 (m, 3H), 2.15–2.29 (m, 1H), 3.04–3.20 (m, 2H), 4.39–4.42 (m, 1H), 6.70 (s, 1H), 7.80 (s, 1H); MS (CI/NH$_3$) m/z: 257 (M+H)$^+$.

39c. 5,6-Dichloro-2-(2-(R)-pyrrolidinyl)furo[3,2-b]pyridine hydrochloride 5,6-Dichloro-2-(2-(R)-pyrrolidinyl)furo[3,2-b]pyridine (120 mg, 0.47 mmol) was slurried in Et$_2$O (5 mL) and a saturated solution of HCl in Et$_2$O was added dropwise. The solvent was removed and the product was recrystallized from MeOH/Et$_2$O to afford short white needles (86 mg, 63%): mp>260° C.; [α]$_D^{20}$ −4.5 (c 0.51, MeOH); $^1$H NMR (D$_2$O, 300 MHz) δ 2.18–2.65 (m, 4H), 3.51–3.56 (m, 2H), 5.05 (dd, J=8, 8 Hz, 1H), 7.16 (d, J=1 Hz, 1H), 8.24 (d, J=1 Hz, 1H); MS (CI/NH$_3$) m/z: 257 (M+H)$^+$; Anal. Calcd for C$_{11}$H$_{10}$Cl$_2$N$_2$O.HCl: C, 45.00; H, 3.78: N, 9.54. Found: C, 45.01; H, 3.71; N, 9.48.

EXAMPLE 40

Preparation of 5,6-Dichloro-2-(1-methyl-2-(R)-pyrrolidinyl)furo[3,2-b]pyridine hydrochloride 5,6-Dichloro-2-(2-(R)-pyrrolidinyl)furo[3,2-b]pyridine from Example 39b (56 mg, 0.22 mmol) was dissolved in an aqueous solution of 37% formaldehyde (excess) and 88% formic acid (excess). The aqueous mixture was heated to 60° C. for 1 hour and then allowed to cool to ambient temperature. The reaction mixture was washed with Et$_2$O, basified with 15% NaOH solution and extracted with CH$_2$Cl$_2$ (2×). The organic phases were combined, dried (MgSO$_4$), concentrated and chromatographed (silica gel; CHCl$_3$/MeOH, 98:2) to afford a solid. The solid was dissolved in Et$_2$O (10 mL) and a saturated solution of HCl in Et$_2$O was added dropwise. The solvent was removed and the product recrystallized from MeOH/Et$_2$O to afford a white solid (31 mg, 46%): mp 244–246° C.; $^1$H NMR (D$_2$O, 300 MHz) δ 2.27–2.37 (m, 2H), 2.47–2.71 (m, 2H), 2.93 (s, 3H), 3.38 (m, 1H), 3.78 (m, 1H), 4.81 (m, partially buried under H$_2$O peak, 1H), 7.27 (s, 1H), 8.26 (s, 1H); MS (CI/NH$_3$) m/z: 271 (M+H)$^+$; Anal. Calcd for C$_{12}$H$_{12}$Cl$_2$N$_2$O.HCl: C, 46.85; H, 4.26; N, 9.11. Found: C, 46.53; H, 4.21; N, 8.82.

EXAMPLE 41

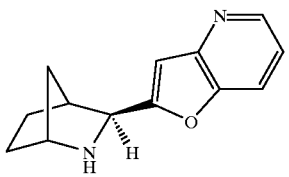

Preparation of 2-((1R,4S)-2-aza-3-(S)-bicyclo[2.2.1] heptyl)-furo[3,2-b]pyridine dihydrochloride 41a. Ethyl (1R,4S)-3-(S)-2-azabicyclo[2.2.1] heptanecarboxylate hydrochloride A suspension of ethyl (1S,4R)-3-(S)-N-((R)-α-methylbenzyl)-2-azabicyclo[2.2.1]hept-5-enecarboxylate (2.40 g, 8.80 mmol, prepared according to the method described by L. Stella et al., *Tetrahedron Lett.*, 31:2603 (1990)) in ethanol (100 mL) and 20% Pd/C (1.2 g) was placed under 4 atmosphere of H$_2$ at room temperature for 12 hours. The reaction mixture was then filtered and concentrated in vacuo to give the free base as an oil (1.33 g). $^1$H NMR (CDCl$_3$, 300 MHz) δ 4.18 (q, 2H), 3.57 (br s, 1H), 3.34 (s, 1H), 2.63 (br s, 1H), 2.12 (m, 2H), 1.68–1.28 (m, 5H), 1.28 (t, 3H); MS (CI/NH$_3$) m/z: 170 (M+H)$^+$. The resultant oil was dissolved in CH$_2$Cl$_2$ (~20 mL) and upon addition of HCl/Et$_2$O (~6.25 M) a white solid precipitated. The solid was then recrystallized from EtOH/Et$_2$O and dried under vacuum at 50° C. to give the title compound (0.94 g, 52%): mp>200° C.

41b. Ethyl (1R,4S)-N-BOC-2-aza-3-(S)-bicyclo[2.2.1] heptanecarboxylate

To a solution of the compound of example 41a (5.0 g, 24.4 mmol) in CH$_2$Cl$_2$ (100 mL) at room temperature under nitrogen was added NEt$_3$ (3.4 g, 24.4 mmol) followed by di-t-butyldicarbonate (5.8 g, 26.8 mmol). After 18 hours aqueous pH 4 buffer was added and the mixture was extracted with Et$_2$O (2×50 mL). The combined organic layers were dried over anhydrous sodium sulfate and concentrated in vacuo. The crude product was purified by flash chromatography on silica gel (EtOAc/hexane 1:4) to yield the title compound (5.4 g, 82%) as an oil: $^1$H NMR (CDCl$_3$, 300 MHz) δ 1.28 (br d, 1H), 4.18 (m, 2H), 3.78 (d, 1H), 2.67 (br. s, 1H), 1.94 (br d, 1H), 1.80–1.40 (m, 5H), 1.44 (d, 9H), 1.28 (t, 3H); MS (CI/NH$_3$) m/z: 270 (M+H)$^+$, 287 (M+NH$_4$)$^+$.

41c. (1R,4S)-3-(S)-N-BOC-2-azabicyclo[2.2.1] heptanemethanol

To a solution of the product of example 41b (20.0 g, 74.3 mmol) in THF (100 mL) at 0° C. under nitrogen was added lithium aluminum hydride (5.64 g, 148.5 mmol) slowly. The mixture was stirred for 1.5 hours and then quenched with Na$_2$SO$_4$.10H$_2$O. Et$_2$O was added and the mixture was stirred for 1 h, filtered through diatomaceous earth and concentrated in vacuo to give the title compound (16.9 g, 100%) as a white solid: $^1$H NMR (CDCl$_3$, 300 MHz) δ 1.25 (d, J=10.5 Hz, 1H), 1.49 (s, 9H), 1.58–1.78 (m, 4H), 2.30 (br d, J=1.8 Hz, 1H), 3.43–3.63 (m, 4H), 4.10 (s, 1H), 4.43 (dd, J=2.4, 2.4 Hz, 1H); MS (CI/NH$_3$) m/z: 171 (M-t-butyl+H)$^+$, 228 (M+H)$^+$.

41d. (1R,4S)-N-BOC-2-aza-3-(S)-bicyclo[2.2.1] heptanecarboxaldehyde

To a mixture of the product of example 41c in DMSO (70 mL) was added a solution of sulfur trioxide pyridine complex (17.63 g, 110.7 mmol) in DMSO (30 mL). The mixture was then stirred for 15 minutes, poured into ice water, and extracted with Et₂O. The organic layer was then washed with saturated NaHCO₃, 10% citric acid, H₂O, and brine, dried (MgSO₄), and concentrated in vacuo to give the title compound as an oil (5.08 g, 60%): ¹H NMR (CDCl3, 300 MHz) δ 1.26 (m, 1H), 1.45 (s, 9H), 1.61–1.81 (m, 5H), 2.75 (s, 1H), 3.66 (s, 1H), 4.31 (s, 1H), 9.55 (d, J=2.1 Hz, 1H); MS (CI/NH₃) m/z: 226 (M+H)⁺, 243 (M+NH₄)⁺.

41e. (1R,4S)-3-(S)-(2,2-Dibromoethenyl)-N-BOC-2-azabicyclo[2.2.1]heptane

To a solution of triphenylphosphine (29.6 g, 113 mmol) in CH₂Cl₂ (60 mL) under nitrogen at 0° C. was added carbon tetrabromide (14.9 g, 45.2 mmol). The mixture was warmed to room temperature and added slowly a solution of the product of example 41d (5.08 g, 22.5 mmol) in CH₂Cl₂ (10 mL). After 5 minutes, the mixture was diluted with Et₂O (50 mL) then filtered through silica gel (EtOAc wash). The filtrate was concentrated and the residue was diluted with EtOAc/hexane (1:4). The resulting precipitate was removed by filtration and the filtrate was concentrated. The resulting residue (9.77 g) was chromatographed (silica gel; Hexane/Et₂O, 95:5; Hexane/EtOAc, 90:10) to afford a solid (4.33 g, 51%): ¹H NMR (CDCl₃, 300 MHz) δ 1.32 (br s, 1H), 1.45 (s, 9H), 1.60–1.80 (m, 5H), 2.45 (br s, 1H), 3.83 (d, J=8.1 Hz, 1H), 4.12 (br s, 1H), 6.31 (d, J=8.1 Hz, 1H); MS (CI/NH₃): 382 (M+H)⁺.

41f. (1R,4S)-3-(S)-ethynyl-N-BOC-2-azabicyclo[2.2.1]heptane

A 2.5 M solution of n-BuLi in hexane (11.4 mL, 28.4 mmol) was added slowly to a solution of the product of Example 41e (4.33 g, 11.4 mmol) in THF (40 mL) under nitrogen at 0° C. The mixture was then stirred for 10 minutes, quenched with saturated NaHCO₃ and extracted with EtOAc (2×). The combined organic extracts were washed with H₂O and brine, dried (MgSO₄), and concentrated. The crude oil (2.87 g) was chromatographed (silica gel; Hexane/EtOAc, 90:10) to afford a colorless oil (1.17 g, 46%): ¹H NMR (CDCl₃, 300 MHz) δ 1.36–1.42 (m, 3H), 1.50 (s, 9H), 1.66–1.75 (m, 2H), 2.10 (m, 1H), 2.25 (d, J=1.5 Hz, 1H), 2.59 (s, 1H), 3.89 (s, 1H), 4.18 (s, 1H); MS (CI/NH₃): 222 (M+H)⁺, 239 (M+NH₄)⁺.

41g. 2-((1R,4S)-2-aza-3-(S)-bicyclo[2.2.1]heptyl)-furo[3,2-b]pyridine dihydrochloride A solution of 2-iodo-3-hydroxypyridine (0.4 g, 1.8 mmol), bis(triphenylphosphine)-palladium(II)chloride (0.06 g, 0.09 mmol), copper (I) iodide (0.05 g, 0.27 mmol), and NEt₃ (0.25 mL, 1.8 mmol) in DMF (2 mL) was stirred for 1 hour. Then a solution of the product of example 41f (0.4 g, 1.8 mmol) in DMF (0.5 mL) was added. The mixture was heated at 60° C. for 16, quenched with saturated NaHCO₃, and extracted with EtOAc (2×). The combined EtOAc extracts were washed with H₂O and brine, dried (MgSO₄), and concentrated. The crude solid (0.64 g) was chromatographed (silica gel; hexane/EtOAc, 60:40) to give a yellow colored solid (0.27 g). This was dissolved in CH₂Cl₂ and upon addition of HCl/Et₂O a solid precipitated which was collected and further purified by heating in MeOH with activated carbon for 15 minutes. After filtering, the MeOH filtrate was concentrated to give the title compound (0.11 g, 22%) as a white solid: mp 182–185° C.; [α]_D = +33.2 (c 0.29, MeOH); ¹H NMR (MeOH-d₄, 300 MHz) δ 1.81–2.01 (m, 6H), 2.24–2.28 (br d, J=11.8 Hz, 1H), 3.31 (s, 1H), 4.28 (s, 1H), 7.51 (s, 1H), 7.87 (m, 1H), 8.58 (br d, J=8.5 Hz, 1H), 8.62 (br s, 1H); MS (CI/NH₃) m/z: 215 (M+H)⁺, 232 (M+NH₄)⁺; Anal. Calcd for C₁₃H₁₆Cl₂N₂O.0.2 HCl.0.5 H₂O: C, 51.45; H, 5.71; N, 9.23. Found: C, 51.48; H, 5.72; N, 8.98.

EXAMPLE 42

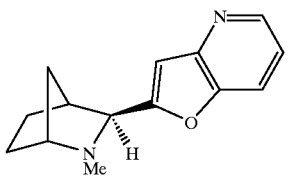

Preparation of 2-((1R,4S)-2-aza-3-(S)-bicyclo[2.2.1]heptyl)-2-methylfuro[3,2-b]pyridil dihydrochloride To a solution of 2-((1R,4S)-2-aza-3-(S)-bicyclo[2.2.1]heptyl)furo[3,2-b]pyridine dihydrochloride (from Example 41, 0.08 g, 0.3 mmol) in EtOH (3.0 mL), formaldehyde (37% w/w aqueous) (5.0 mL) and HOAc (0.2 mL) was added sodium cyanoborohydride (0.08 g, 1.4 mmol). The mixture was stirred for 16 hours, quenched with saturated NaHCO₃, and extracted with Et₂O. The organic layer was washed with H₂O, dried (MgSO₄) and concentrated. The crude product (0.22 g) was chromatographed (silica gel; EtOH/EtOAc, 10:90) to afford an oil (0.06 g). The oil was dissolved in CH₂Cl₂ and a solution of HCl in Et₂O was added. The solvent was removed and the product was recrystallized from CH₂Cl₂/Et₂O to afford the title compound as a white solid (0.09 g, 100%): mp 225° C. (dec.); [α]_D = +5.4 (c 0.35, MeOH); ¹H NMR (MeOH-d₄, 300 MHz) δ 1.84–2.24 (m, 5H), 2.41 (m, 1H), 3.12 (s, 3H), 3.20 (br s, 1H), 4.22 (s, 1H), 4.61 (s, 1H), 7.62 (s, 1H), 7.94 (dd, J=6.0, 6.0 Hz, 1H), 8.73 (dd, J=0.9, 1.2 Hz, 1H), 8.84 (br, d, J=6.0 Hz, 1H); MS (CI/NH₃) m/z: 229 (M+H)⁺, 246 (M+NH₄)⁺; Anal. Calcd for C₁₄H₁₈Cl₂N₂O.0.2 H₂O: C, 55.17; H, 6.08; N, 9.19. Found: C, 55.24; H, 5.76; N, 9.05.

EXAMPLE 43

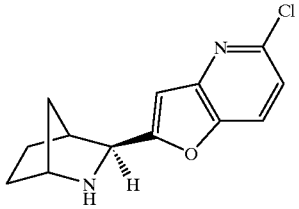

Preparation of 2-((1R,4S)-2-aza-3-(S)-bicyclo[2.2.1]heptyl)-5-chloro-furo[3,2-b]pyridine dihydrochloride A solution of 6-chloro-2-iodo-3-hydroxy pyridine (0.46 g, 1.8 mmol) from step 11c, bis(triphenylphosphine)-palladium(II)chloride (0.06 g, 0.09 mmol), copper (1) iodine (0.05 g, 0.27 mmmol), NEt₃ (0.25 mL, 1.8 mmol) in DMF (2 mL) was stirred for 1 hour. Then a solution of (1R,4S)-3-(S)-ethynyl-N-t-butylcarboxyl-2-azabicyclo[2.2.1]heptane from Example 41f above (0.40 g, 1.8 mmol) in DMF (0.5 mL) was added. The mixture was heated at 60° C. for 16 h, quenched with saturated NaHCO₃ and extracted with EtOAc. The combined EtOAc extracts were washed with H₂O and brine, dried (MgSO₄), and concentrated. The crude product (0.68 g) was chromatographed (silica gel; hexane/EtOAc, 80:20) to give a solid (0.57 g). The solid was dissolved in CH₂Cl₂ and a solution of HCl in Et₂O was added. The solvent was removed and the product was recrystallized from EtOH/Et₂O to afford the title compound as a white solid (0.47 g, 93%): mp>200° C.; [α]$_D^≦$+31.2 (c 0.29, MeOH); $^1$H NMR (MeOH-d$_4$, 300 MHz) δ 1.77–1.99 (m, 5H), 2.24 (m, 1H), 3.15 (s, 1H), 4.23 (s, 1H), 4.74 (s, 1H), 7.15 (s, 1H), 7.43 (d, J=9.0 Hz, 1H), 8.00 (dd, J=0.9, 0.9 Hz, 1H); MS (CI/NH$_3$) m/z: 249 (M+H)$^+$; Anal. Calcd for C$_{13}$H$_{14}$Cl$_2$N$_2$O.0.1 HCl: C, 54.06; H, 4.92; N, 9.70. Found: C, 54.21; H, 4.90; N, 9.50.

EXAMPLE 44

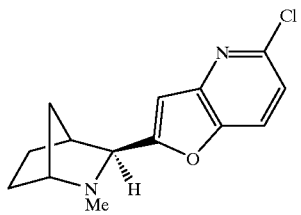

Preparation of 2-((1R,4t)-2-aza-3-(S)-bicyclo[2.2.1]heptyl)-5-chloro-2-methylfuro[3,2-b]pyridine dihydrochloride To a solution of 37% aqueous formaldehyde (12 mL) and 88% formic acid (6 mL) was added 2-((1R,4S)-2-aza-3-(S)-bicyclo[2.2.1]heptyl)-5-chlorofuro[3,2-b]pyridine dihydrochloride from Example 43 above (0.4 g, 1.4 mmol). The reaction solution was refluxed for 16 hours. After cooling to ambient temperature, the solution was basified to pH 12 by the addition of solid K$_2$CO$_3$, and extracted with EtOAc. The organic extract was washed with H$_2$O, dried (MgSO$_4$), and concentrated. The crude solid was dissolved in CH$_2$Cl$_2$ and a solution of HCl in Et$_2$O was added. The solvent was removed and the title compound (0.03 g, 22%) was collected as a white solid: mp 197–200° C.; [α]$_D^{23}$ +5.6 (c 0.23, MeOH); $^1$H NMR (MeOH-d$_4$, 300 MHz) δ 1.82–2.21 (m, 5H), 2.33–2.38 (m, 2H), 3.08 (s, 3H), 3.13 (br s, 1H), 4.16 (s, 1H), 4.45 (s, 1H), 7.23 (s, 1H), 7.43 (d, J=8.7 Hz, 1H), 8.04 (dd, J=0.9, 1.2 Hz, 1H); MS (CI/NH$_3$) m/z: 263 (M+H)$^+$; Anal. Calcd for C$_{14}$H$_{17}$Cl$_3$N$_2$O.0.2 HCl.0.9 H$_2$O: C, 46.82; H, 5.33; N, 7.80. Found: C, 46.76; H, 5.34; N, 7.47.

EXAMPLE 45

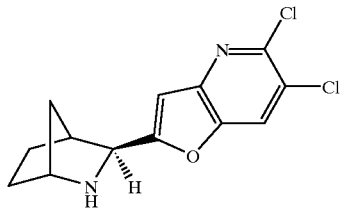

Preparation of 2-((1R,4S)-2-aza-3-(S)-bicyclo[2.2.1]heptyl)-5,6-dichlorofuro[3,2-b]pyridine dihydrochloride A solution of 2-iodo-3-hydroxy-5,6-dichloropyridine (0.45 g, 1.6 mmol) from Example 25a, bis(triphenylphosphine)palladium(II)chloride (0.06 g, 0.08 mmol), copper (I) iodide (0.05 g, 0.24 mmol), NEt$_3$ (0.22 mL, 1.6 mmol) in DMF (1.5 mL) was stirred for 1 hour. Then a solution (1R,4S)-3-(S)-ethynyl-N-t-butyloxycarboxyl-2-azabicyclo[2.2.1]heptane from Example 41f above (0.4 g, 1.8 mmol) in DMF (1.0 mL) was added. The mixture was heated at 60° C. for 16 hours, quenched with saturated NaHCO$_3$ and extracted with EtOAc (2×). The combined EtOAc extracts were washed with H$_2$O, brine, dried (MgSO$_4$), and concentrated. The crude solid (0.60 g) was chromatographed (silica gel; Hexane/EtOAc. 80:20) to give a solid (0.2 g). The solid was then dissolved in CH$_2$Cl$_2$ and a solution of HCl in Et$_2$O was added. The solvent was removed and the product was recrystallized from EtOH/Et$_2$O to afford a white solid (23 mg, 5.1%): mp>200° C.; $^1$H NMR (MeOH-d$_4$, 300 MHz) δ 1.74–1.99 (m, 5H), 2.20–2.25 (m, 1H), 3.15 (s, 1H), 4.23 (s, 1H), 4.74 (s, 1H), 7.19 (d, J=0.6 Hz), 8.30 (s, 1H); MS (CI/NH$_3$) m/z: 283 (M+H)$^+$, 300 (M+NH$_4$)$^+$; Anal. Calcd for C$_{13}$H$_{12}$Cl$_2$N$_2$O.0.6 EtOH.0.8 HCl: C, 50.17; H, 4.86; N, 8.24. Found: C, 50.12; H, 4.78; N, 8.15.

EXAMPLE 46

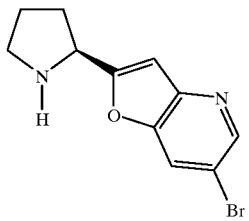

Preparation of 6-bromo-2-(2-(S)-pyrrolidinyl)furo[3,2-b]pyridine dihydrochloride 46a. 2-(1-BOC-2-(S)-pyrrolidinyl)-6-bromofuro[3,2-b]pyridine A sample of 5-bromo-3-pyridinol (2.06 g, 11.8 mmol) (which may be prepared according to Clausson-Kass, et al., U.S. Pat. No. 4,192,946) and Na$_2$CO$_3$ (3.65 g, 2.1 mmol) were dissolved in H$_2$O (25 mL). To this solution was added I$_2$ (3.0 g, 12 mmol), and the reaction mixture was stirred overnight. The mixture was then poured slowly into 2M aqueous HCl, and the acidity was adjusted to pH 3. The product was collected by filtration and crystallized from EtOH/ether, affording title compound (2.92 g, 83%): MS (CI/NH$_3$) m/e: 300 (M+H)$^+$, 317 (M+NH$_4$)$^+$; $^1$H NMR (CDCl$_3$, 300 MHz) δ 7.25 (d, J=2 Hz, 1H), 7.93 (d, J=2 Hz, 1H).

A sample of 5-bromo-2-iodo-3-pyridinol (0.60 g, 2.0 mmol), from above, was dissolved in DMF (3 mL), and Pd(PPh$_3$)$_2$Cl$_2$ (0.07 g, 0.1 mmol), CuI (0.077 g, 0.4 mmol) and triethylamine (0.33 mL, 2.4 mmol) were added. The mixture was stirred under N$_2$ at room temperature for 1 hour, then 1-BOC-2-(S)-ethynylpyrrolidine (0.429 g, 2.2 mmol), from Example 1c above, dissolved in DMF (1 mL), was added carefully. The reaction mixture was stirred at 60° C. for 16 hours, then cooled to room temperature. The reaction mixture was diluted with ether, then washed with 10% NaOH and brine. The organic extract was dried over MgSO$_4$ and concentrated. The residue was chromatographed (silica gel; hexane/EtOAc, 5:1 to 2:1) to give the title compound (0.32 g, 43%): $^1$H NMR (CDCl$_3$, 300 MHz) δ 1.32, 1.46 (2 s, 9H), 1.91–2.40 (m, 4H), 3.37–3.70 (m, 2H), 4.93–5.15 (m, 1H), 6.66 (s, 1H), 7.85 (s, 1H), 8.55 (s, 1H); MS (CI/NH$_3$) m/z: 367, 369 (M+H)$^+$.

46b. 6-bromo-2-(2-(S)-pyrrolidinyl)furo[3,2-b]pyridine dihydrochloride

A sample (0.14 g, 0.38 mmol) of the compound from step 46a above was dissolved in a solution of hydrogen chloride in dioxane (4 N, 3 mL) and cooled to 0° C. After stirring at room temperature for 16 hours, the solvent was evaporated under reduced pressure. The residue was then triturated with ether several times to give the hydrochloride salt as a white solid (0.119g, 92%): $[\alpha]_D^{23}$ +4.09 (c 0.45, MeOH); $^1$H NMR (D$_2$O, 300 MHz) δ 2.14–2.50 (m, 3H), 2.59 (m, 1H), 3.50–3.55 (m, 2H), 5.07 (t, 1H, J=7.7 Hz), 7.22 (t, J=0.7 Hz, 1H), 8.32 (dd, J=0.7, 1.8 Hz, 1H), 8.66 (d, 1H, J=1.8 Hz); MS (CI/NH$_3$) m/z: 267, 269 (M+H)$^+$; Anal. Calcd for C$_{11}$H$_{11}$N$_2$OBr.2HCl: C, 38.04; H, 3.83; N, 8.07. Found: C, 38.01; H, 3.75; N, 7.92.

EXAMPLE 47

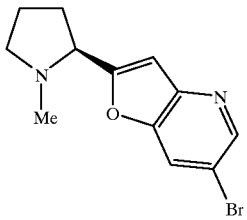

Preparation of 6-bromo-2-(1-methyl-2-(S)-pyrrolidinyl)furo[3,2-b]pyridine dihydrochloride A sample of 2-(1-BOC-2-(S)-pyrrolidinyl)-6-chlorofuro[3,2-b]pyridine (180 mg, 0.49 mmol), from Example 46a above, was dissolved in 1.5 mL of 88% formic acid and 3 mL of 37% aqueous formaldehyde and heated at 100° C. for 16 hours. The reaction mixture was cooled to ambient temperature, poured into saturated aqueous K$_2$CO$_3$, and extracted with CH$_2$Cl$_2$. The organic extract was dried over MgSO$_4$, and the solvent was removed. The residue was chromatographed (silica gel; EtOAc/MeOH, 10:1) to give the amine as colorless oil (92 mg, 67%). The amine was converted to the hydrochloride salt by treatment with HCl/ether, and the salt was recrystallized from EtOH/EtOAc to give the title compound (68 mg, 61%) as a white solid: $^1$H NMR (D$_2$O, 300 MHz) δ 2.20–2.40 (m, 2H), 2.46–2.80 (m, 3H), 3.00 (br s, 3H), 3.38 (m, 1H), 3.88 (m, 1H), 7.32 (s, 1H), 8.31 (dd, J=0.7, 1.8 Hz, 1H), 8.67 (d, J=1.8 Hz, 1H); MS (CI/NH$_3$) m/e: 281 (M+H)$^+$, 283 (M+2H)$^+$; Anal. Calcd for C$_{12}$H$_{13}$N$_2$OBr.1.8HCl: C, 41.56; H, 4.30; N, 8.08. Found: C, 41.60; H, 4.12; N, 7.89. $[\alpha]_D$ –2.8 (c 0.20, MeOH)

EXAMPLE 48

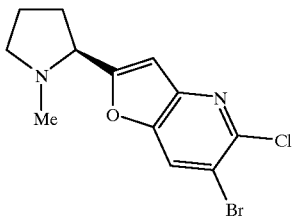

Preparation of 6-bromo-5-chloro-2-(1-methyl-2-(S)-pyrrolidinyl)furo[3,2-b]pyridine dihydrochloride 48a. 2-(1-BOC-2-(S)-pyrrolidinyl)-5-chloro-6-bromofuro[3,2-b]pyridine 3-Bromo-2-chloro-5-hydroxy-6-iodopyridine (2.0 g, 6.0 mmol)(prepared by treatment of 3-bromo-2-chloro-5-hydroxypyridine (Koch & Schnatterer, Synthesis 1990, 499) with I$_2$ (ibid, p. 497), palladium (II) bis(triphenylphosphine) chloride (0.21 g, 0.30 mmol), CuI (0.228 g, 1.2 mmol) and triethylamine (1.0 mL) were dissolved in DMF (8 mL). After stirring at room temperature for 1 hour, the acetylene from Example 3a (1.40 g, 7.2 mmol) was added and the resultant mixture was stirred at room temperature for 16 hours. The mixture was diluted with EtOAc, and washed with H$_2$O: brine (1:1, 3×). The organic layer was dried, concentrated and chromatographed (silica gel; hexane/EtOAc, 10:1 to 5:1) to afford the title compound as colorless oil (170 mg, 11%): $^1$H NMR (CDCl$_3$, 300 MHz) δ 1.31 (s, 5H), 1.46 (s, 4H), 1.8–1.95 (m, 2H), 1.96–2.23 (m, 2H), 3.32–3.58 (m, 2H), 4.15–4.41 (m, 1H), 6.60 (s, 1H), 7.95 (s, 1H); MS (CI/NH$_3$) m/z: 403 (M+H)$^+$.

48b. 6-bromo-5-chloro-2-(1-methyl-2-(S)-pyrrolidinyl)furo[3,2-b]pyridine dihydrochloride A sample of 2-(2-(S)-pyrrolidinyl)-5-chloro-6-bromofuro[3,2-b]pyridine (170 mg, 0.42 mmol), from Example 48a above, was dissolved in 1.0 mL of 88% formic acid and 3 mL of 37% aqueous formaldehyde and heated at 100° C. for 16 hour. The reaction mixture was cooled, poured into saturated aqueous K$_2$CO$_3$, and the mixture was extracted with CH$_2$Cl$_2$. The extract was dried over MgSO$_4$, and the solvent was removed. The residue was chromatographed (silica gel; hexane/EtOAc, 5:1 to 1:1) to give the amine as colorless HCl/ether, and the salt was recrystallized from EtOH/EtOAc to give the title compound (50 mg, 71%): mp 250–253° C.; $[\alpha]_D^{\leq}$ –28.3 (c, 0.35, MeOH); $^1$H NMR (D$_2$O, 300MHz) δ 2.26–2.38 (m, 2H), 2.47–2.72 (m, 2H), 2.93 (s, 3H), 3.41 (m, 1H), 3.78 (m, 1H), 7.27 (s, 1H), 8.40 (s, 1H); MS (CI/NH$_3$) m/z: 315(M+H)$^+$; Anal. Calcd for C$_{12}$H$_{12}$N$_2$OBrCl.HCl: C, 40.94; H,3.72; N,7.96. Found: 40.76; H, 3.76; N, 7.79.

EXAMPLE 49

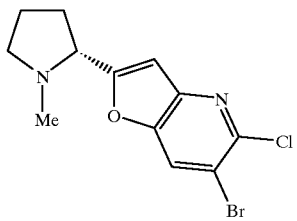

Preparation of 6-bromo-5-chloro-2-(2-(R)-pyrrolidinyl)furo[3,2-b]pyridine hydrochloride 49a. 2-(1-BOC-2-(R)-pyrrolidinyl)-5-chloro-6-bromofuro[3,2-b]pyridine 5-Bromo-6-chloro-3-hydroxy-2-iodopyridine (4.0 g, 12.0 mmol) from Example 48a, palladium (II) bis(triphenylphosphine) chloride (0.42 g, 0.60 mmol), CuI (0.456 g, 2.4 mmol) and triethylamine (2.0 mL) were mixed in DMF at room temperature. The mixture was stirred at room temperature for one hour, the acetylene of Example 3a (2.56 g, 13.2 mmol) was added. The mixture was heated at 55° C. over two nights. After cooling to room temperature, Et$_2$O (20 mL) was added and the mixture was washed with H$_2$O: Brine (1:1, 3×). The organic layer was dried, concentrated and chromatographed (silica gel; (1:1, 3×). The organic layer was dried, concentrated and chromatographed (silica gel; (CDCl$_3$, 300 MHz) δ 1.31, 1.46 (s, 9H), 1.95–2.06 (m, 2H), 2.06–2.20 (m, 1H), 2.20–2.35 (m, 1H), 3.42–3.70 (m, 2H), 4.95, 5.07 (br s, 1H), 6.60 (s, 1H), 7.95 (s, 1H); MS (CI/NH$_3$) m/z: 403 (M+H$_4$)$^+$.

49b. 6-bromo-5-chloro-2-(2-(R)-pyrrolidinyl)furo[3,2-b]pyridine hydrochloride

To a sample of the compound from step 49a above was added a 4.0 M solution of HCl in dioxane. After stirring for 12 hours, the solvent was evaporated. The white solid was triturated with Et$_2$O and dried under vacuum to afford the hydrochloride salt: mp>250° C.; $[\alpha]_D^{23}$ −4.83 (c 0.14, MeOH); $^1$H NMR (D$_2$O, 300 MHz) δ 2.20–2.50 (m, 3H), 2.5–2.65 (m, 1H), 3.51 (t, J=6.9 Hz, 2H), 5.04 (t, J=18.0 Hz, 1H), 7.15 (s, 1H), 8.39 (s, 1H); MS (CI/NH$_3$) m/z: 301 (M+H)$^+$; Anal. Calcd for C$_{10}$H$_{11}$N$_2$OClBr.HCl: C, 39.09; H, 3.28; N, 8.29. Found: C, 39.12; H, 3.54; N, 7.91.

EXAMPLE 50

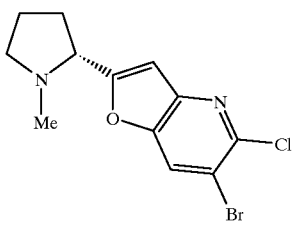

Preparation of 6-bromo-5-chloro-2-(-1-methyl-2(R)-pyrrolidinyl)furo[3,2-b]pyridine hydrochloride 50a. 6-bromo-5-chloro-2-(1-methyl-2-(R)-pyrrolidinyl)furo[3,2-b]pyridine A sample of the compound from step 49a above (0.355 g, 0.88 mmol) in 88% formic acid (5.0 mL) and 37% aqueous formaldehyde (10 mL) was heated at 70° C. for two hours. After cooling to room temperature, the solution was basified to pH 9 with saturated aqueous NaHCO$_3$ and extracted with CH$_2$Cl$_2$ (3×). The combined organic extracts were dried, concentrated and chromatographed (silica gel; CH$_2$Cl$_2$/MeOH, 10:0.2 to 10:0.5) to afford an oil (0.226 g, 81%): $^1$H NMR (CDCl$_3$, 300 MHz) δ 1.80–1.97 (m 1H), 2.00–2.15 (m, 2H), 2.24 (m, 1H), 2.33 (s, 3H), 3.25 (m, 1H), 3.45 (m, 1H), 4.73 (m, 1H); 6.72 (s, 1H), 7.98 (s, 1H); MS (CI/NH$_3$) m/z: 315 (M+H)$^+$.

50b. 6-bromo-5-chloro-2-(1-methyl-2-(R)-pyrrolidinyl)furo[3,2-b]pyridine hydrochloride To an ethereal solution of the compound from step 50a at room temperature was added a 1.0 M solution of HCl in Et$_2$O dropwise until precipitation ceased. The solvent was removed, and the white solid was triturated with Et$_2$O then dried under vacuum to afford the title compound: mp 246–248° C.; $[\alpha]_D^{\leq}$ +32.65 (c 0.68, MeOH); $^1$H NMR (D$_2$O, 300 MHz) δ 2.25–2.40 (m, 2H), 2.46–2.70 (m, 2H), 2.94 (s, 3H), 3.40 (m, 1H), 3.81 (m, 1H), 4.83 (m, 1H), 7.27 (s, 1H), 8.40 (s, 1H); MS (CI/NH$_3$) m/z: 315(M+H)$^+$; Anal. Calcd for C$_{12}$H$_{12}$N$_2$OBrCl.1.1HCl.0.3H$_2$O: C, 39.91; H, 3.82; N,7.76. Found: 40.26; H, 4.00; N, 7.39.

EXAMPLE 51

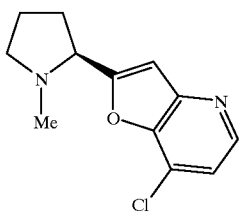

Preparation of 7-chloro-2-(1-methyl-2-(S)-pyrrolidinyl)furo[3,2-b]pyridine hydrochloride 51a. 2-(1-BOC-2-(S)-pyrrolidinyl)-7-chloro-furo[3,2-b]pyridine To a solution of 4-chloro-3-hydroxy-2-iodopyridine (1.04 g, 4.10 mmol) in DMF (10 mL) was added (Ph$_3$P)$_2$PdCl$_2$ (0.140 g, 0.20 mmol), CuI (0.152 g, 0.80 mmol) and Et$_3$N (0.496 g, 4.90 mmol). The mixture was stirred at room temperature for one hour. A solution of 1-Boc-2-(S)-ethynylpyrrolidine (0.80 g, 4.10 mmol), from step 1c above, in DMF (10 mL) was added and the mixture was heated at 60° C. for 16 hours. The reaction mixture was cooled to room temperature and poured into saturated NaHCO$_3$ and washed with Et$_2$O (4×100 mL). The combined organic extracts were washed with brine/H$_2$O (1/1 400 mL), dried (MgSO$_4$), and concentrated. The crude product was chromatographed (silica gel; CH$_2$Cl$_2$/MeOH, 90:10) to afford the title compound as a brown oil (0.180 g, 14%): $^1$H NMR (CDCl$_3$, 300 MHz) δ 1.40 (s, 9H), 1.95–2.10 (m, 4H), 3.10–3.25 (m, 2H), 4.90–5.10 (m, 1H), 6.65 (s, 1H), 7.10 (br s, 1H), 8.38 (br s, 1H); MS (DCI/NH$_3$) m/z: 323 (M+H)$^+$.

51b. 7-chloro-2-(1-methyl-2-(S)-pyrrolidinyl)furo[3,2-b]pyridine hydrochloride

A solution of 2-(1-BOC-2-(S)-pyrrolidinyl)-7-chlorofuro[3,2-b]pyridine, from step 51a above, in HCO$_2$H (15.0 mL, 88%) and H$_2$CO (15 mL, 37%) was refluxed for one hour. After cooling to room temperature and the solution was acidified to pH=2.0 with 1 N aqueous HCl and washed with Et$_2$O (150 mL). The aqueous layer was basified with 15% NaOH and extracted with CH$_2$Cl$_2$ (4×400 mL). The combined CH$_2$Cl$_2$ extracts were dried (MgSO$_4$) and concentrated. The crude material was chromatographed (silica gel; CH$_2$Cl$_2$:MeOH, 95:5) to afford the title compound as a light yellow oil (0.036 g, 15%). The amine was dissolved in Et$_2$O and cooled to 0° C. and a saturated solution of HCl in Et$_2$O was added until precipitation ceased. The solvent was removed and the yellow solid was placed under vacuum to afford the title compound: $[\alpha]_D^{\leq}$ +26.24 (c 0.05, H$_2$O); $^1$H NMR (D$_2$O, 300 MHz) δ 2.28–2.42 (m, 2H), 2.50–2.68 (m, 2H), 2.98 (s, 3H), 3.42 (br s, 1H), 3.62 (br s, 1H), 5.00 (m, 1H), 7.38 (s, 1H), 7.59 (d, J=6.0 Hz, 1H), 8.44 (d, J=6.0 Hz, 1H); MS (DCI/NH$_3$) m/z: 237 (M+H)$^+$; Anal. Calcd for C$_{12}$H$_{13}$N$_2$O.1.2 HCl.0.10H$_2$O.0.20Et$_2$O: C, 51.75; H, 5.56; N, 9.43. Found C, 51.40; H, 5.49; N,9.03.

EXAMPLE 52

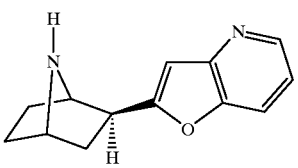

(±)-2-(7-aza-2-exo-bicyclo[2.2.1]heptyl)furo[3,2-b]pyridine dihydrochloride 52a. (±)7-aza-7-(tert-butoxycarbonyl)-2-exo-bicyclo[2.2.1]heptanemethanol

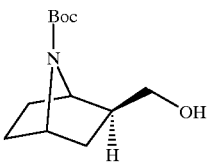

A solution of the exo-substituted ester (12.3 g, 48.1 mmol, prepared according to the procedure of Hernandez et al., *J. Org. Chem.*, 60:2683–2691 (1995)) in THF (40 mL) was added to a suspension of lithium aluminum hydride (4.38 g, 115 mmol) in THF (120 mL) at −10° C. After 30 minutes, the reaction was quenched by the careful addition of solid Na$_2$SO$_4$.10H$_2$O until gas evolution ceased. The mixture was diluted with Et$_2$O and some Celite was added. The mixture was stirred at ambient temperature for 1 hour then the solids were removed by filtration through a pad of Celite and anhydrous Na$_2$SO$_4$. Concentration of the filtrate afforded the title compound as a colorless oil (10.3 g, 94%): $^1$H NMR (CDCl$_3$, 300 MHz) δ 1.23–1.55 (m, 3H), 1.45 (s, 9H), 1.75–1.82 (m, 2H), 1.88–1.94 (m, 2H), 3.38–3.44 (m, 2H), 4.14–4.22 (m, 2H); MS (CI/NH$_3$) m/z: 228 (M+H)$^+$, 245 (M+NH$_4$)$^+$.

52b. (±)-7-aza-7-(tert-butoxycarbonyl)-2-exo-bicyclo[2.2.1]heptanecarboxaldehyde

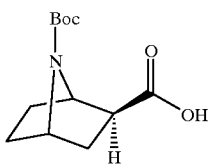

To solution of oxalyl chloride (4.73 mL, 54.2 mmol) in CH$_2$Cl$_2$ (200 mL) at −78° C. was added dimethyl sulfoxide (7.70 mL, 108 mmol). After 10 minutes, a solution of (±)7-aza-7-(tert-butoxycarbonyl)-2-exo-(hydroxymethyl)-bicyclo[2.2.1]heptane, from step 52a above, in CH$_2$Cl$_2$ (25 mL) was added. After 15 minutes, triethylamine (31.5 mL, 226 mmol) was added. The reaction mixture was stirred at −78° C. for 30 minutes, then warmed to −40° C. over a 30 minute period. The reaction was quenched by the addition of saturated aqueous NH$_4$Cl, warmed to ambient temperature, and extracted with CH$_2$Cl$_2$ (2×). The combined organic extracts were dried (Na$_2$SO$_4$) and concentrated to afford the title compound as a pale yellow oil (9.82 g, 96%): $^1$H NMR (CDCl$_3$, 300 MHz) δ 1.42 (s, 9H), 1.39–1.60 (m, 3H), 1.84 (m, 1H), 2.20 (m, 1H), 2.50 (m, 1H), 3.09 (m, 1H), 4.29 (br s, 1H), 4.53 (br s, 1H), 9.64 (d, J=2.0 Hz, 1H); MS (CI/NH$_3$) m/z: 226 (M+H)$^+$, 243 (M+NH$_4$)$^+$.

52c. (±)7-aza-7-(tert-butoxycarbonyl)-2-exo-(2,2-dibromoethenyl)-bicyclo[2.2.1]heptane.

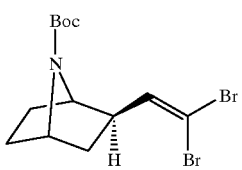

Carbon tetrabromicle (28.9 g, 87.2 mmol) was added to a 0° C. solution of triphenyphosphine (57.2 g, 218 mmol) in CH$_2$Cl$_2$ (200 mL) under a nitrogen atmosphere. The solution was warmed to ambient temperature, stirred for 10 minutes, then a solution of the aldehyde from step 52b in CH$_2$Cl$_2$ (20 mL) was added via cannula. After 15 minutes, the reaction mixture was diluted with 1:1 EtOAc/hexane (300 mL) and filtered through a pad of Celite and silica gel (1:1 EtOAc/hexane wash). The filtrate was concentrated and the residue was purified by chromatography (silica gel; hexane/EtOAc 90:10) to afford the title compound as a colorless oil (12.8 g, 77%): $^1$H NMR (CDCl$_3$, 300 MHz) δ 1.46 (s, 9H), 1.38–1.60 (m, 3H), 1.70–1.86 (m, 3H), 2.56 (dt, J=4.4, 8.8 Hz, 1H), 4.05 (br s, 1H), 4.24 (br s, 1H), 6.39 (d, J=8.8 Hz, 1H); MS (CI/NH$_3$) m/z: 382 (M+H)$^+$, 399 (M+NH$_4$)$^+$.

52d. (±)-7-(tert-butoxycarbonyl)-2-exo-ethynyl-7-azabicyclo[2.2.1]heptane

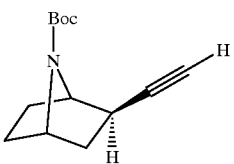

To a solution of the vinyl dibromide (12.8 g, 33.7 mmol), from step 52c above, in THF (170 mL) at −78° C. was added a 2.5 M solution of n-butyllithium in hexane (27.6 mL, 69.0 mmol). The reaction was quenched after 15 minutes at −78° C. by the addition of saturated aqueous NH$_4$Cl and warmed to ambient temperature. The mixture was extracted with EtOAc (2×). The combined organic extracts were washed with brine, dried (Na$_2$SO$_4$), and concentrated. Purification of the residue by chromatography (silica gel; hexane/EtOAc 80:20) afforded the title compound as a colorless oil (6.95 g, 93%): $^1$H NMR (CDCl$_3$, 300 MHz) δ 1.24–1.48 (m, 2H), 1.46 (s, 9H), 1.64–1.92 (m, 4H), 2.09 (d, J=2.4 Hz, 1H), 2.50 (m, 1H), 4.32 (br s, 2H); MS (CI/NH$_3$) m/z: 222 (M+H)$^+$, 239 (M+NH$_4$)$^+$.

52e. (±)-2-7-aza-(7-BOC-2-exo-bicyclo[2.2.1]heptyl)furo[3,2-b]pyridine

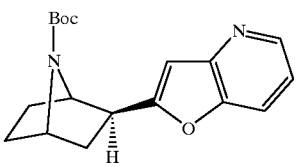

3-Hydroxypyridine (366 mg, 1.65 mmol), copper(I) iodide (47 mg, 0.25 mmol), bis(triphenylphosphine)palladium(II) chloride (58 mg, 0.083 mmol) and triethylamine (242 mL, 1.74 mmol) were combined in DMF (3.0 mL) and allowed to stir for 1 hour. A solution of (±)-7-(tert-Butoxycarbonyl)-2-exo-ethynyl-7-azabicyclo[2.2.1]heptane (366 mg, 1.65 mmol), from step 52d, in DMF (1 mL) was added and the reaction mixture was heated to 60° C. for 12 hours then 80° C. for 4 hours. After cooling to ambient temperature, the mixture was diluted with 15% NaOH and extracted with Et$_2$O (3×). The combined organic extracts were dried (MgSO$_4$), concentrated and purified by chromatography (silica gel; EtOAc/hexane, 50:50) to afford the title compound as a white solid (362 mg, 70%): $^1$H NMR (CDCl$_3$, 300 MHz) δ 1.24 (br s, 9H), 1.38–1.64 (m, 2H), 1.79–2.01 (m, 3H), 2.13 (m, 1H), 3.15 (dd, J=5.3, 8.6 Hz, 1H), 4.42 (br s, 1H), 4.50 (br s, 1 H), 6.64 (s, 1H), 7.14 (dd, J=5.4, 8.2 Hz, 1H), 7.64 (d, J=8.2 Hz, 1H), 8.48 (d, J=5.4 Hz, 1H); MS (CI/NH$_3$) m/z: 315 (M+H)$^+$.

52f. (±)-2-(7-aza-2-exo-bicyclo[2.2.1]heptyl)furo[3,2-]pyridine

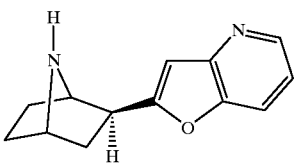

The compound from step 52e above (330 mg, 1.05 mmol) was dissolved in CH$_2$Cl$_2$ (3 mL) and TFA (3 mL) was added at ambient temperature. After stirring for 30 minutes, the solvent was removed and the residue was diluted with CH$_2$Cl$_2$ and washed with saturated K$_2$CO$_3$ solution, dried (MgSO$_4$) and concentrated. The crude product was chromatographed (silica gel; CHCl$_3$/MeOH/NH$_4$OH, 90:10:0.1) to afford the amine as a light yellow oil (223 mg, 99%): $^1$H NMR (CDCl$_3$, 300 MHz) δ 1.40–1.58 (m, 2H), 1.66–2.14 (m, 6H), 3.15 (dd, J=5.4, 9.3 Hz, 1H), 3.83 (br s, 2H), 6.60 (s, 1H), 7.16 (dd, J=5.4, 8.4 Hz, 1H), 7.64 (dd, J=1.0, 6.5 Hz, 1H), 8.48 (dd, J=1.0, 5.4 Hz, 1H); MS (CI/NH$_3$) m/z: 215 (M+H)$^+$.

52g (±)-2-(7-aza-2-exo-bicyo[2.2.1-]heptyl)furo[3,2-b]pyridine dihydrochloride

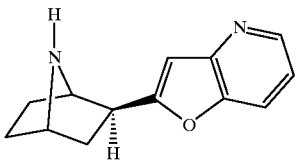

The compound from step 52f above (219 mg, 1.02 mmol) was dissolved in Et$_2$O and a saturated solution of HCl in Et$_2$O was added dropwise. The solvent was removed and the precipitate was triturated with Et$_2$O (3×) then placed under vacuum to afford the title compound as white solid (245 mg, 80%): $^1$H NMR (D$_2$O, 300 MHz) δ 1.85–2.32 (m, 7H), 3.77 (dd, J=5.8, 9.5 Hz, 1H), 4.47 (m, 1H), 4.65 (d, J=3.8 Hz, 1H), 7.07 )s, 1H), 7.64 (dd, J=5.4, 8.5 Hz, 1H), 8.30 (dd, J=1.0, 6.5 Hz, 1H), 8.55 (dd, J=1.0, 5.8 Hz, 1H); MS (CI/NH$_3$) m/z: 215 (M+H)$^+$, 232 (M+NH$_4$)$^+$; Anal. Calcd for C$_{13}$H$_{14}$N$_2$O.2.0HCl.0.8H$_2$O: C, 51.77; H, 5.88; N, 9.29. Found: C, 51.81; H, 5.66; N, 9.07.

EXAMPLE 53

Preparation of 2-((S)-pyrrolidinyl)-6-phenylfuro[3,2-b]pyridine dihydrochloride 53a 2-(1-Boc-2-(S)-pyrrolidinyl)-6-phenylfuro(3,2-b)pyridine The 2-(1-BOC-2-(S)-pyrrolidinyl)-6-bromofuro[3,2-b]pyridine (0.2 g, 0.54 mmol) obtained from Example 46a above was dissolved in toluene (2 mL). Phenylbororic acid (0.19 g, 1.62 mmol), palladium (O) tetrakis(triphenyl phosphine) (40 mg) and 2 M Na$_2$CO$_3$ solution (1 mL) were then added to the toluene solution. The resultant mixture was heated under reflux for 16 h. The desired product was extracted with CH$_2$Cl$_2$, dried over MgSO$_4$ and filtered. Solvent was then removed under reduced pressure and the residue was chromatographed (silica gel: Hexane/EtOAc, 5:1 to 2:1) to afford an oil (0.22 g, 100%). MS (CI/NH$_3$) m/z: 365 (M+H)+; 1H NMR (CDCl3, 300 MHz) δ 1.32, 1.50 (2s, 9H), 1.90–2.22 (m, 3H), 2.30 (m, 1H), 3.42–3.73 (m, 2H), 4.97–5.20 (m, 1H), 6.92–7.02 (m, 1H), 7.33–7.66 (m, 5H), 7.93 (s, 1H), 8.90 (s, 1H).

53b 2-(2-(S)-pyrrolidinyl)-6-phenylfuro[3,2-b]pyridine dihydrochloride

A sample of compound 53a (50 mg, 0.14 mmol) from above was dissolved in hydrogen chloride in dioxane (4 N, 3 mL) at 0° C. After stirring at room temperature for 16 h, the solvent was evaporated under reduced pressure. The residue was then triturated with ether several times to give the hydrochloride salt as a white solid (19 mg, 51%): mp 220–225° C.; [α]$_D$$^{23}$ +11.5 (c 0.20, MeOH); MS (CI/NH$_3$) m/z: 265 (M+H)$^+$; $^1$H NMR (D$_2$O, 300 MHz) δ: 2.19–2.54 (m, 4H), 2.70 (m, 1H), 3.53–3.58 (m, 2H), 5.10 (m, 1H), 7.32 (d, J=0.7 Hz, 1H), 7.50–7.63 (m, 3H), 7.75–7.78 (m, 2H), 8.46 (dd, J=0.8, 1.5 Hz, 1H), 8.87 (d, J=1.8 Hz, 1H). Anal. Calcd. for C$_{17}$H$_{16}$N$_2$2 HCl.0.2 H$_2$O: C, 60.55; H, 5.38; N, 8.31. Found: C, 59.91; H, 5.44; N, 8.22.

EXAMPLE 54

Preparation of 2-(1-methyl-2-(S)-pyrrrolidinyl)-6-phenylfuro[3,2-b]pyridine dihydrochloride A sample of compound (170 mg, 0.47 mmol) from Example 53 above, was dissolved in 1 mL of HCOOH and 2 mL of HCHO and heated at 100° C. for 16 hour. The reaction mixture was cooled, poured into saturated aqueous K$_2$CO$_3$, and the mixture was extracted with CH$_2$Cl$_2$. The extract was dried over MgSO$_4$, and the solvent was removed. The residue was chromatographed (silica gel; EtOAc/MeOH, 10:1) to give the amnine as colorless oil (48 mg, 40%). The amine was converted to the hydrochloride salt by treatment with HCl/ether, and the salt was recrystallized from EtOH/EtOAc to give the title compound (39 mg, 64%): mp 188–191° C.; [α]D-1 (c 0.48, MeOH); MS (CI/NH$_3$) m/e: 279 (M+H)$^+$; $^1$H NMR (D$_2$O, 300 MHz) δ 2.32–2.36 (m, 2H), 2.52–2.74 (m, 3H), 3.02 (br s, 3H), 3.40 (m, 1H), 3.90 (m, 1H), 7.40 (s, 1H), 7.52–7.63 (m, 3H), 7.74–7.78 (m, 2H), 8.39 (dd, J=0.73, 1.84 Hz, 1H), 8.86 (d, J=1.84 Hz, 1H). Anal. Calcd. for C$_{18}$H$_{18}$N$_2$O.2.0HCl.0.5 H$_2$O: C, 60.01; H, 5.87; N, 7.78. Found: C, 59.95; H, 5.79; N, 7.61.

EXAMPLE 55

Preparation of 2-(2-(R)-pyrrolidinyl)-5-chloro-6-phenyl furo[3,2-b]pyridine hydrochloride 55a 2-(1-Boc-2(R)-pyrrolidinyl-5-chloro-6-phenyl furo(3,2-b)pyridine The 2-(1-Boc-2(R)-pyrrolidinyl)-5-chloro-6-bromofuro [3,2-b]pyridine (0.495 g, 1.23 mmol) obtained in Example 50a above, was dissolved in toluene (15 mL). Phenylbororic acid (0.18 g, 1.48 mmol), palladium (O) tetrakis (triphenylphosphine) (40 mg) and 2 M aqueous Na$_2$CO$_3$ (1.3 mL) were added to the reaction mixture and refluxed overnight. The solvent was evaporated and the residue was chromatographed (silica gel; Hexane/EtOAc, 100:5 to 5:1) to afford an oil (0.41 g, 83%). MS (CI/NH$_3$) m/z: 399 (M+H)$^+$; $^1$H NMR (CDCl$_3$, 300 MHz) δ 1.35, 1.46 (s, 9H), 1.95–2.07 (m, 2H), 2.16 (m, 1H), 2.30 (m, 1H), 3.41–3.70 (m, 2H), 4.96, 5.10 (br s, 1H), 6.67 (s, 1H), 7.46 (s, 5H), 7.68 (s, 1H).

55b 2-(2-(R)-pyrrolidinyl)-5-chloro-6-phenyl furo[3,2-b]pyridine hydrochloride

The compound of Example 55a was added to a solution of 4.0 M HCl in dioxane. The mixture was stirred at room temperature overnight. The solvent was evaporated and the salt was then triturated in Et$_2$O and dried under vacuum. mp>250° C. [α]$_D$$^{23}$−6.50 (c 0.40, MeOH); MS (CI/NH$_3$) m/z: 300 (M+H)$^+$; $^1$H NMR (D$_2$O, 300 MHz) δ 2.20–2.56 (m, 4H), 2.60 (m, 1H), 3.55 (t, J=7.5 Hz, 2H), 5.07 (t, J=8.0 Hz, 1H), 7.19 (d, J=0.7 Hz, 1H), 7.57 (s, 5H), 8.03 (d, J=1.1 Hz, 1H); Anal. Calcd. for C$_{17}$H$_{15}$N$_2$OCl.1.2 HCl: C, 59.61; H, 4.77; N; 8.18. Found: C, 59.32; H, 4.67; N, 8.30.

EXAMPLE 56

Preparation of 5-chloro-2-(1-methyl-2-(R)-pyrrolidinyl)-6-phenyl furo[3,2-b]pyridine hydrochloride 56a 5-chloro-2-(1-methyl-2-(R)-pyyrolidinyl)-6-phenyl furo (3,2-b)pyridine To the compound obtained in Example 55a (0.22 g, 0.55 mmol) was added formic acid (3.0 mL) and formaldehyde (37%, 6 mL). The mixture was heated at 80° C. for two hours. After cooling to room temperature, the solution was basified to pH 9 with saturated aqueous NaHCO$_3$ followed by extraction with CH$_2$Cl$_2$ (3×). The combined organic layers were dried, concentrated and chromatographed (silica gel; CH$_2$Cl$_2$/MeOH, 10:0.3 to 10:0.5) to afford an oil (0.11 g, 62%). MS (CI/NH$_3$) m/z: 313 (M+H)$^+$; $^1$H NMR (CDCl$_3$, 300 MHz) δ 1.91 (m, 1H), 2.01–2.30 (m, 3H), 2.36 (s, 3H), 3.27 (t, J=7.6 Hz, 1H), 3.46 (t, J=8.3 Hz, 1H), 4.91 (m, 1H), 6.78 (s, 1H), 7.46 (s, 5H), 7.68 (s, 1H).

56b 5-chloro-62-(1-methyl-2-(R)-pyrrolidinyl)-phenyl furo[3,2-b]pyridine hydrochloride The compound obtained in Example 56a was dissolved in Et$_2$O and 1.0 HCl in Et$_2$O was added dropwise. The solvent was evaporated and the salt was triturated in Et$_2$O and dried under vacuum. mp 252–254° C.; [α]$_D^{23}$+38.79 (c 0.50, MeOH); MS (CI/NH$_3$) m/z: 313 (M+H)$^+$; $^1$H NMR (D$_2$O, 300 MHz) δ 2.28–2.40 (m, 2H), 2.50–2.70 (br, 2H), 2.97 (br s, 3H), 3.40 (br s, 1H), 3.80 (br s, 1H), 4.86 (br s, 1H), 7.30 (s, 1H), 7.58 (s, 5H), 8.05 (s, 1H); Anal. Calcd. for C$_{18}$H$_{17}$N$_2$OCl.1.3HCl: C, 60.02; H, 5.12; N, 7.78. Found: 60.07; 5.09; N, 7.81.

EXAMPLE 57

Preparation of 6-(3-aminophenyl)-5-chloro-2-(2-(R)-pyrrolidinyl)furo[3,2-b]pyridine hydrochloride 57a 2-(1-Boc-2-(R)-pyrrolidinyl)-5-chloro-6-(3-aminophenyl)furo[3,2-b]pyridine The 2-(1-Boc-2-(R)-pyrrolidinyl)-5-chloro-6-bromo furo[3,2-b]pyridine (0.469 g, 1.2 mmol), obtained in Example 50a above, was dissolved in toluene (10 mL). 3-Aminophenyl boric acid (0.445 g, 2.87 mmol), Pd(O) tetrakis(tri-phenylphosphine) (0.04 g) and 2 M aqueous NaHCO$_3$ (1.5 mL) were added to the solution. The mixture was refluxed for two days. The solvent was evaporated and the residue was chromatographed (silica gel; hexane/EtOAc, 5:1 to 2:1) to afford an oil (0.20 g, 41%). MS (CI/NH$_3$) m/z: 414 (M+H)$^+$; $^1$H NMR (CDCl$_3$, 300 MHz) δ 1.34, 1.46 (s, 9H), 1.95–2.08 (m, 2H), 2.15 (m, 1H), 2.28 (m, 1H), 3.58–3.68 (m, 2H), 4.98, 5.10 (br s, 1H), 6.24 (m, 1H), 6.63 (s, 1H) 6.76 (d, J=9.3 Hz, 2H), 6.82 (d, J=9.3 Hz, 1H) 7.62 (s, 1H).

57b 6-(3-aminophenyl)-5-chloro-2-(2-(R)-pyrrolidinyl)-furo[3,2-b]pyridine

The compound obtained above (0.193 g, 0.47 mmol) was dissolved in CH$_2$Cl$_2$ (2 mL) at 0° C. and TFA (1 mL) was added. The mixture was stirred and warmed to room temperature. After stirring for 30 min, it was basified with saturated aqueous NaHCO$_3$ to pH 9 and extracted with CH$_2$Cl$_2$ (3×). The combined organic layers were dried, concentrated and chromatographed (silica gel; CH$_2$Cl$_2$/MeOH, 10:0.5 to 10:1) to afford an oil (0.125 g, 85%). MS (CI/NH$_3$) m/z: 313 (M+H)$^+$; $^1$H NMR (CDCl$_3$, 300 MHz) δ 1.99–2.05 (m, 3H), 2.23 (m, 1H), 3.70–3.82 (m, 2H), 4.43 (m, 1H), 6.73 (d, J=9.3 Hz, 2H), 6.82 (d, J=9.3 Hz, 1H), 7.28 (d, J=1.3 Hz, 2H), 7.66 (s, 1H).

57c 6-(3-aminophenyl)-5-chloro-2-(2-(R)-pyrrolidinyl)-furo[3,2-b]pyridine hydrochloride The compound obtained above was dissolved in Et$_2$O and 1.0 M HCl in Et$_2$O was added dropwise. The solvent was evaporated and the salt was then triturated in Et$_2$O and dried under vacuum. mp>250° C.; MS (CI/NH$_3$) m/z: 313 (M+H)$^+$; $^1$H NMR (D$_2$O, 300 MHz) δ 2.20–2.45 (m, 3H), 2.46–2.64 (m, 1H), 3.56 (t, J=7.1 Hz, 2H), 5.06 (t, J=7.8 Hz, 1H), 6.99–7.05 (m, 3H), 7.19 (s, 1H), 7.35–7.42 (m, 1H), 8.02 (s, 1H); Anal. Calcd. for C$_{17}$H$_{16}$N$_3$OCl.1.2HCl: C, 57.11; H, 4.85; N, 11.75. Found: C, 57.07; H, 4.87; N, 11.54.

EXAMPLE 58

Preparation of 5-chloro-2-(2-(R)-pyrrolidinyl)-6-(2-(4-pyridylethenyl) furo[3,2-b]pyridine hydrochloride 58a 2-(1-Boc-2-(R)-pyrrolidinyl)-5-chloro-6-(4-vinylpyridyl) furo(3,2-b)pyridine 6-bromo-5-chloro-2-(1-methyl-2-(R)-pyrrolidinyl)furo[3,2-b]pyridine (0.522 g, 1.30 mmol) from Example 50a above was dissolved in acetonitrile (10 mL). To this solution was added Pd(II) acetate (0.052 g, 0.23 mmol), tri-o-tolyphosphine (0.26 g, 0.85 mmol), triethylamine (2.8 mL) and 4-vinylpyridine (0.17 mL, 1.56 mmol). The mixture was heated at 85° C. for two days. EtOAc (15 mL) was added, and the mixture was washed with saturated NaHCO$_3$. The organic layer was dried, concentrated and chromatographed (silica gel; Hexane/EtOAc, 4:1 to 1:2) to afford an oil (0.22 g, 40%). MS (CI/NH$_3$) m/z: 426 (M+H)$^+$; $^1$H NMR (CDCl$_3$, 300 MHz) δ 1.32, 1.46 (s, 9H), 1.96–2.05 (m, 2H), 2.15 (m, 1H), 2.28 (m, 1H), 3.60 (br s, 2H), 4.98, 5.11 (br s, 1H), 6.62 (s, 1H), 6.98 (d, J=18.3 Hz, 1H), 7.42 (d, J=7.0 Hz, 2H), 7.74 (d, J=18.3 Hz, 1H), 7.99 (s, 1H), 8.64 (d, J=7.0 Hz, 2H).

58b 5-chloro-6-(2-(4-pyridylethenyl)-2-(2-(R)-pyrrolidinyl) furo(3,2-b)pyridine

The compound obtained above (0.21 g, 0.49 mmol) was dissolved in CH$_2$Cl$_2$ (2 mL) at 0° C. and then TFA (1.3 mL) was added. The mixture was stirred and warmed to room temperature. After stirring for 30 min, it was basified with saturated aqueous NaHCO$_3$ to pH 9 and extracted with CH$_2$Cl$_2$ (3×). The combined organic layer was dried, concentrated and chromatographed (silica gel; CH$_2$Cl$_2$/MeOH, 10:0.2 to 10:0.5) to afford an oil (0.123 g, 77%). MS (CI/NH$_3$) m/z: 326 (M+H)$^+$; $^1$H NMR (CDCl$_3$, 300 MHz) δ 1.80–2.10 (m, 3H), 2.26 (m, 1H), 3.06–3.22 (m, 2H), 4.42(m, 1H), 6.70 (s, 1H), 6.95 (d, J=16.6 Hz, 1H), 7.42 (d, J=5.0 Hz, 2H), 7.70 (d, J=16.6 Hz, 1H), 8.00 (s, 1H), 8.61 (d, J=5.0 Hz, 2H).

58c 5-chloro-6-(2-(4-pyridylethenyl)-2-(2-(R)-pyrrolidinyl)-furo[3,2-b]pyridine hydrochloride The compound from step 58b above was dissolved in Et$_2$O and 1.0 M HCl in Et$_2$O was added dropwise. The solvent was evaporated and the salt was triturated in Et$_2$O and dried under vacuum. mp 230° C. (dec.); [α]$_D^{23}$−16.25 (c 0.40, MeOH); MS (CI/NH$_3$) m/z: 326 (M+H)$^+$; $^1$H NMR (D$_2$O, 300 MHz) δ 2.00–2.20 (m, 2H), 2.29 (m, 1H), 2.45 (m, 1H), 3.30–3.40 (m, 2H), 5.00 (m, 1H), 7.43 (s, 1H), 7.65 (d, J=16.3 Hz, 1H), 7.95 (d, J=16.3 Hz, 1H), 8.03 (d, J=15.8 Hz, 2H), 8.76 (s, 1H), 8.79 (d, J=6.1 Hz, 2H); Anal. Calcd. for C$_{18}$H$_{16}$N$_3$OCl.2.2HCl.0.3Et$_2$O: C, 53.85; H, 4.99; N, 9.81. Found: C, 53.89; H, 4.85; N,9.50.

EXAMPLE 59

Preparation of 5-chloro-2-(1-methyl-2-(S)-pyrrolidinyl)-6-(3-pyridyl)furo[3,2-b]pyridine hydrochloride 59a. 2-(1-Boc-2-(S)-pyrrolidinyl)-6-(3-pyridyl) furo (3,2-b) pyridine The 2-(1-BOC-2-(S)-pyrrolidinyl)-6-bromofuro[3,2-b]pyridine (0.24g, 0.64 mmol) obtained from Example 46a above was dissolved in toluene (6 mL). Tributyl-3-pyridyltin (0.36 g, 1.3 mmol), palladium (O) tetrakis(triphenyl phosphine) (40 mg) was then added to the toluene solution and the resultant mixture was heated under reflux for 16 h. The desired product was extracted with CH$_2$Cl$_2$, dried over MgSO$_4$ and filtered. Solvent was then removed under reduced pressure and the residue was chromatographed (silica gel: Hexane/EtOAc, 5:1 to EtOAc) to afford an oil (0.13 g, 56%). MS (CI/NH$_3$) m/z: 366 (M+H)$^+$; $^1$H NMR (CDCl$_3$, 300 MHz) δ 1.33, 1.55 (2s, 9H), 1.92–2.38 (m, 3H), 3.43–3.70 (m, 2H), 5.08 (m, 1H), 5.15 (m, 1H), 6.75 (brs, 1H), 7.43 (m, 1H), 7.86 (s, 1H), 7.93 (m, 1H), 8.66 (m, 1H), 8.72 (brs, 1H), 8.89 (s, 1H).

59b. 5-chloro-2-(1-methyl-2-(S)-pyrrolidinyl)-6-(3-pyridyl)-furo[3,2-b]pyridine hydrochloride A sample of compound (130 mg, 0.36 mmol), from Example 59a above, was dissolved in 1 mL of HCOOH and 2 mL of HCHO and heated at 100° C. for 16 hour. The reaction mixture was cooled, poured into saturated aqueous K$_2$CO$_3$, and the mixture was extracted with CH$_2$Cl$_2$. The extract was dried over MgSO$_4$, and the solvent was removed. The residue was chromatographed (silica gel; EtOAc/MeOH, 10:1) to give the amine as colorless oil (67 mg, 68%). The amine was converted to the hydrochloride salt by treatment with HCl/ether, and the salt was recrystallized from EtOH/EtOAc to give the title compound (65 mg): mp 155–163° C.; [α]$_D$+1.5 (c 0.40, MeOH); MS (CI/NH$_3$) m/e: 280 (M+H)$^+$; $^1$H NMR (D$_2$O, 300 MHz) δ 2.30–2.45 (m, 2H), 2.52–2.74 (m, 3H), 3.05 (br s, 3H), 3.40 (m, 1H), 3.92 (m, 114), 7.47 (s, 1H), 8.23 (dd, J=6, 9 Hz, 1H), 8.50 (m, 1H), 8.86 (m, 1H), 8.95 (m, 1H), 8.87 (m, 1H), 9.20 (m, 1H). Anal. Calcd. for C$_{18}$H$_{18}$N$_2$O.3.4 HCl.H$_2$O: C, 48.43; H, 5.81; N, 10.06. Found: C, 48.46; H, 5.36; N, 9.97.

The following examples until example 133 may readily be made according to the procedures described below or as generally described, where applicable, herein. Examples 134–136 were made as described in those examples.

EXAMPLES 60–82

Following the procedure of Example 53, replacing the 2-(1-BOC-2(-pyrrolidinyl)-6-bromofuro[3,2-b]pyridine with the starting material compounds shown in Table 3 and replacing the phenylboronic acid reagent thereof with a R-B(OH)$_2$ reagent shown in Table 3 below, the desired compounds 60–82 having R as described in Table 3 are prepared. The S or the racemic compounds may also readily be prepared from the appropriate precursor(s) as shown in the schemes or tables herein. L can be varied as well and is selected from those variables listed as R in formula I. L at the position shown in Table 3 is preferrably chosen from H, F, Cl or Me.

TABLE 3

| Ex. No. | n | * | L | R of reagent | R |
|---|---|---|---|---|---|
| 60 | 2 | (R) | H | 3-quinolinyl | 3-quinolinyl |
| 61 | 2 | (R) | H | 2-naphthyl | 2-naphthyl |
| 62 | 2 | (R) | H | biphenyl | biphenyl |
| 63 | 2 | (R) | H | 2-thienyl | 2-thienyl |
| 64 | 2 | (R) | H | 4-fluorophenyl | 4-fluorophenyl |
| 65 | 2 | (R) | H | 5-pyrimidinyl | 5-pyrimidinyl |
| 66 | 2 | (R) | H | 3,5-bis(trifluoromethyl)phenyl | 3,5-bis(trifluoromethyl)phenyl |
| 67 | 2 | (R) | Cl | 4-chlorophenyl | 4-chlorophenyl |
| 68 | 2 | (R) | H | 2,4-dichlorophenyl | 2,4-dichlorophenyl |
| 69 | 2 | (R) | H | 4-methylphenyl | 4-methylphenyl |
| 70 | 2 | (R) | H | 3-chloro-4-fluorophenyl | 3-chloro-4-chlorophenyl |
| 71 | 2 | (R) | H | 2-formylphenyl | 2-formylphenyl |
| 72 | 2 | (R) | H | 4-trifluoromethylphenyl | 4-trifluoromethylphenyl |
| 73 | 2 | (R) | H | 2-hydroxy-1-naphthyl | 2-hydroxy-1-naphthyl |
| 74 | 2 | (R) | H | 4'-nitro-4-biphenyl | 4'-nitro-4-biphenyl |
| 75 | 2 | (R) | H | 4'-fluoro-4-biphenyl | 4'-fluoro-4-biphenyl |
| 76 | 2 | (R) | H | 4'-methyl-4-biphenyl | 4'-methyl-4-biphenyl |
| 77 | 2 | (R) | H | 4-methyl-3-thienyl | 4-methyl-3-thienyl |
| 78 | 2 | (R) | H | 2-cyano-3-thienyl | 2-cyano-3-thienyl |
| 79 | 2 | (R) | H | 2-chloro-3-thienyl | 2-chloro-3-thienyl |
| 80 | 2 | (R) | H | 2,4-dimethoxy-5-pyrimidinyl | 2,4-dimethoxy-5-pyrimidinyl |
| 81 | 2 | (R) | H | 5-bromo-phenyl | 5-bromo-phenyl |
| 82 | 2 | (R) | H | 4-methyl-1-naphthyl | 4-methyl-1-naphthyl |

EXAMPLES 83–91

Following the procedure of Example 58 and replacing the 4-vinylpyridine reagent with alkelene or alkyne reagent shown in Table 4 below, the desired compounds 83–91 having R as described in Table 4 are prepared The S compound or racemic compounds may also be prepared from the appropriate precursor(s). L is chosen from R as described for formula I for the designated position and is preferrably selected from H, F, Cl or Me.

TABLE 4

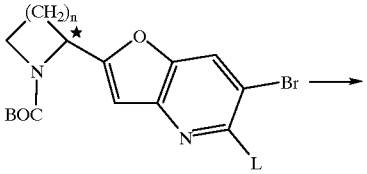

| Ex. No. | n | * | L | R of reagent | R |
|---|---|---|---|---|---|
| 83 | 2 | (R) | H | 1-hexyne | hexynyl |
| 84 | 2 | (R) | H | ethylene | vinyl |
| 85 | 2 | (R) | H | 5,5-dimethyl-1,3-hexadiene | 5,5-dimethyl-1,3-hexadienyl |
| 86 | 2 | (R) | H | 5-cyano-1-pentyne | 5-cyano-1-pentynyl |
| 87 | 2 | (R) | H | 5-phenyl-1-pentyne | 5-phenyl-1-pentynyl |
| 88 | 2 | (R) | H | 6-hydroxyl-1-hexyne | 6-hydroxyl-1-hexynyl |
| 89 | 2 | (R) | H | 2-phenyl-ethyne | 2-phenyl ethynyl |
| 90 | 2 | (R) | H | 3,3-dimethylbutyne | 3,3-dimethylbutynyl |
| 91 | 2 | (R) | H | 1-octyne | 1-octynyl |

EXAMPLE 92

2-(1-Boc-2-(R)-pyrrolidinyl)-6-cyanofuro[3,2-b]pyridine hydrochloride

To a flamed dried flask purged with nitrogen is added 2-(1-Boc-2-(R)-pyrrolidinyl)-6-bromo-furo[3,2-b]pyridine, zinc cyanide and tetrakis(triphenylphosphine)-palladium (O). To the mixture is added degassed DMF (20 mL), and the mixture is heated to 80° C. for 16 hours. The mixture is poured into saturated $NaHCO_3$ (200 mL), and extracted with EtOAc (450 mL), which is dried ($MgSO_4$) and concentrated. The mixture is then purified by chromatography.

EXAMPLE 93

6-benzoyl-2-(2-(R)-pyrrolidinyl)furo[3,2-b]pyridine hydrochloride 93a, 6-benzoyl-2-(1-Boc-2-(R)-pyrrolidinyl)furo[3,2-b]pyridine hydrochloride The 2-(1-Boc-2-(R)-pyrrolidinyl)-6-cyanofuro[3,2-b]pyridine of Example 92 in anhydrous ether at 0° C. is treated with 1.5 equivalents of phenylmagnesium bromide in ether and stirring is maintained at 0 to 35° C. until the nitrile is largely consumed. The solvent is evaporated and the residue is treated with 2M aqueous potassium hydrogen sulfate to hydrolyze the intermediate imine. The solution is made basic with potassium carbonate and extracted with EtOAc. The combined extracts are dried ($Na_2SO_4$) and concentrated to a residue which is chromatographed (silica gel) to afford the title compound.

93.b 6-benzoyl-2-(2-(R)-pyrrolidinyl)furo[3,2-b]pyridine hydrochloride 6-(benzoyl)-2-(1-Boc-2-(R)-pyrrolidinyl)furo[3,2-b]pyridine is dissolved in $CH_2Cl_2$ (10 mL). The mixture is cooled to 0° C., TFA (10 mL) is added and the reaction is stirred for 45 minutes as it warms to room temperature. The mixture is concentrated in vacuo and taken up in a minimum amount of $H_2O$. The aqueous mixture is basified with 15% NaOH and extracted with $CH_2Cl_2$ (200 mL), which is dried ($MgSO_4$) and concentrated. The residue is chromatographed (silica gel) to afford the free amine. The isolated free amine is taken up in a minimum amount of $Et_2O$, cooled to 0° C., and treated with HCl in EtOH to afford the hydrochloride salt.

EXAMPLES 94–97

Following the procedure of Example 93, replacing the 2-(1-Boc-2-(R)-pyrrolidinyl)-6-cyanofuro[3,2-b]pyridine with the starting material compounds shown in Table 5 and replacing the phenylmagnesium bromide reagent thereof with a $R^5$—Mg—Br Grignard reagent shown in Table 5 below, the desired compounds 94–97 having L and $R^5$ as described in Table are prepared. S or R or racemic compounds may be prepared from the appropriate precursor(s). L is equal to R as described for formula I at that position. $R^5$ is also selected from the variables as listed in formula I.

TABLE 5

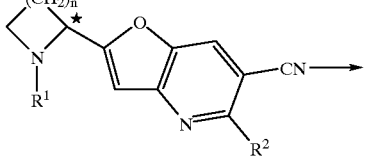

| Ex. No. | n | * | L | $R^5$ of reagent | $R^5$ |
|---|---|---|---|---|---|
| 94 | 2 | (R) | H | n-hexyl | n-hexyl |
| 95 | 2 | (R) | H | 3-quinolinyl | 3-quinolinyl |
| 96 | 2 | (R) | H | 2-naphthyl | 2-naphthyl |
| 97 | 2 | (R) | H | 4-methyl-1-naphthyl | 4-methyl-1-naphthyl |

EXAMPLES 98–103

Following the procedure of Example 93, replacing the 2-(1-Boc-2-(R)-pyrrolidinyl)-6-cyano-furo[3,2-b]pyridine with the starting material compounds shown in Table 6 and replacing the phenylmagnesium bromide reagent thereof with a $R^5$—Mg—Br Grignard reagent shown in Table 6 below, the desired compounds 112–117 having L and $R^5$ as described in Table 6 are prepared.

TABLE 6

[Structure: BOC-N-azetidine/pyrrolidine-(CH₂)ₙ with stereocenter attached to furo[3,2-b]pyridine bearing CN, with L substituent] → [Structure: HN-ring-(CH₂)ₙ attached to furo[3,2-b]pyridine bearing C(=O)R⁵, with L substituent]

| Ex. No. | n | * | L | R⁵ | of Grignard agent R⁵ |
|---|---|---|---|---|---|
| 98  | 2 | (R) | H | 3-pyridinyl | 3-pyridinyl |
| 99  | 2 | (R) | H | 5-pyrimidinyl | 5-pyrimidinyl |
| 100 | 2 | (R) | H | 3-pyridazinyl | 3-pyridazinyl |
| 101 | 2 | (R) | H | 2-thienyl | 2-thienyl |
| 102 | 2 | (R) | H | phenylmethyl | phenylmethyl |
| 103 | 2 | (S) | H | 2-(4-methoxy-phenyl)ethyl | 2-(4-methoxy-phenyl)ethyl |

EXAMPLES 104–107

Following the procedure of Example 58, replacing 6-bromo-5-chloro-2-(1-methyl-2-(R)-pyrrolidinyl)furo[3,2-b]pyridine with starting material compounds shown in Table 7, replacing the 4-vinylpyridine starting reagent thereof with the starting reagent compounds shown in Table 7, then hydrogenating the product thereof with palladium or platinum on charcoal the desired compounds 104–107 having L and R⁹ as described in Table 7 are prepared. S, R or racemic compounds may be prepared from the appropriate precursor(s) L is chosen from R in formula I and is preferrably chosen from H, Cl, F or Me. This reaction is partially described in Scheme 19.

TABLE 7

[Structure: R¹-N-ring-(CH₂)ₙ attached to furo[3,2-b]pyridine bearing Br, with L substituent] → [Structure: R¹-N-ring-(CH₂)ₙ attached to furo[3,2-b]pyridine bearing W, with L substituent]

| Ex. No. | n | * | L | Starting reagent | W |
|---|---|---|---|---|---|
| 104 | 2 | (R) | H | 5-carbomethoxy-3-vinylpyridine | 2-(5-carbomethoxy-pyridinyl)ethyl |
| 105 | 2 | (R) | H | 5-bromo-3-vinylpyridine | 2-(5-bromo-pyridinyl)ethyl |
| 106 | 2 | (R) | H | 6-amino-5-bromo-3-vinylpyridine | 2-(6-amino-5-bromo-pyridinyl)ethyl |
| 107 | 2 | (R) | H | 5-bromo-6-methylamino-3-vinylpyridine | 2-(5-bromo-6-methylamino-pyridinyl)ethyl |

EXAMPLE 108

2-(1-methyl-2-(R)-pyrrolidinyl)-6-(5-methyl-3-pyridyl)-furo[3,2-b]pyridine dihydrochloride 108a. 2-(1-methyl-2-(R)-pyrrolidinyl)-6-(5-methyl-3-pyridyl)-furo[3,2-b]pyridine To a solution of 2-(1-methyl-2-(R)-pyrrolidinyl)-6-(bromo)-furo[3,2-b]pyridine from Example 47 in toluene are added (5-methyl3-pyridyl)tributyltin and tetrakis(triphenylphosphine)palladium(O). After being refluxed overnight, the resulting mixture is cooled to room temperature. Solvent is removed, and the residue is chromatographed on a silica gel column.

108b. 2-(1-methyl-2-(R)-pyrrolidinyl)-6-(5-methyl-3-pyridyl)-furo[3,2-b]pyridine dihydrochloride To a solution of 6-pyridyl-2-(1-methyl-2-(R)-pyrrolidinyl)furo[3,2-b]pyridine from step 108a in THF is added hydrogen chloride (1.0 M in Et₂O). A precipitate forms which is filtered, washed (Et₂O) and vacuum-dried to afford the hydrochloride salt.

EXAMPLES 109–117

Following the procedure of Example 108, replacing the 2-(1-methyl-2-(R)-pyrrodinyl)-6-(bromo)-furo[3,2-b]pyridine thereof with the starting material compound shown in Table 8 and replacing the 3-pyridinyltributyltin reagent thereof with the reagent shown in Table 8, the desired compounds 109–117 having L and R as described in Table 8 are prepared. L may also be selected from the groups listed for R of formula I at the designated position. The heteroaryl groups (het) shown at position $Y^2$ of formula I are added as described above using the appropriate tributyltin reagent. R or S or racemic compounds may be prepared from the appropriate precursor and are included within the scope of the invention. The reagents are either readily available or may be prepared from commercially available starting materials by standard synthetic methods.

TABLE 8

[Structure: (CH2)n-azetidine with N-Me, attached to furo[3,2-b]pyridine with Br and L substituents → product with het replacing Br]

| Ex. No. | n | * | L | reagent | het |
|---|---|---|---|---|---|
| 109 | 2 | (R) | H | (5-carbomethoxy-3-pyridinyl)tributyltin* | 5-carboxy-3-pyridinyl |
| 110 | 2 | (R) | H | (5-carbomethoxy-3-pyridinyl)tributyltin** | 5-formyl-3-pyridinyl |
| 111 | 2 | (R) | H | (5-hydroxymethyl-3-pyridinyl)tributyltin | 5-hydroxymethyl-3-pyridinyl |
| 112 | 2 | (R) | H | (2,4-dimethoxy-5-pyrimidinyl)tributyltin | 2,4-dimethoxy-5-pyrimidinyl |
| 113 | 2 | (R) | H | (2-chloro-3-thienyl)tributyltin | 2-chloro-3-thienyl |
| 114 | 2 | (R) | H | (2-cyano-3-thienyl)tributyltin | 2-cyano-3-thienyl |
| 115 | 2 | (S) | H | (4-methyl-3-thienyl)tributyltin | 4-methyl-3-thienyl |
| 116 | 2 | (S) | H | (4-hydroxymethyl-5-carbomethoxy-3-thienyl)tributyltin | 4-hydroxymethyl-5-carbomethoxy-3-thienyl |
| 117 | 2 | (S) | H | (4-methoxymethoxy-5-carbomethoxy-3-thienyl)tributyltin | 4-methoxymethoxy-5-carbomethoxy-3-thienyl |

*After following the procedures of Example 108, with substitutions as indicated, the carbomethoxy group is hydrolyzed with base as additional step in this preparation.
**After following the procedures of Example 108, with substitutions as indicated, the following additional steps are necessary: the carbomethoxy group is hydrolyzed with base; the resulting free acid is reduced to the alcohol with LiAlH$_4$, and the resulting free alcohol is oxidized to the aldehyde with Swern or Collins reagents.

EXAMPLES 118–120

Following the procedure of Example 58, replacing 6-bromo-5-chloro-2-(2-(R)-pyrrolidinyl)furo[3,2-b]pyridine with starting material compounds shown in Table 9, replacing the vinylpyridine starting reagent thereof with the starting reagent compounds shown Table 9, then optionally hydrogenating the product thereof with palladium on charcoal the desired compounds 118–120 having L and $R^9$ as described in Table 9 are prepared. L may be selected from the group R of formula I as described herein for the designated position and $R^9$, in Table 9, is chosen from arylC$_1$–C$_6$aukyl moieties as exemplified below. As with the previous compounds, the R or S or racemic compounds may be prepared from the appropriate precursor(s). In addition, as is required for all nucleophilic additions to the bicyclic ring system, L is not selected from a moiety which prevents the regioselective addition to position $Y^2$ on the compound of formula I.

TABLE 9

[Structure: (CH2)n-azetidine with N-BOC, attached to furo[3,2-b]pyridine with Br and L → product with W replacing Br and R$^1$ on N]

| Ex. No. | n | * | L | Starting reagent | W |
|---|---|---|---|---|---|
| 118 | 2 | (R) | H | 4-methyl-3-vinylbenzene | 2-(4-methyl-3-phenyl)ethyl |
| 119 | 2 | (R) | R | 4-methoxy-3-vinylbenzene | 2-(4-methoxy-3-phenyl)ethyl |
| 120 | 2 | (R) | H | 4-trifluoromethyl-3-vinylbenzene | 2-(4-trifluoromethyl-3-phenyl)ethyl |

EXAMPLE 121

6-benzoylaminomethyl(2-(2-(R)-pyrrolidinyl)furo[3,2-b]pyridine hydrochloride 121a. 2-(1-Boc-2-(R)-pyrrolidinyl)-6-(N-aminomethyl))furo[3,2-b]pyridine 2-(1-Boc-2-(R)-pyrrolidinyl)-6-(cyano) furo[3,2-b]pyridine from step 92 is stirred in the presence of Raney nickel and ammonium hydroxide under 1 atm of hydrogen at room temperature. The mixture is filtered, and the solvent is removed to give the title compound 121b. 6-benzoylaminomethyl-2-(1-Boc-2-(R)-pyrrolidinyl)furo[3,2-b]pyridine To 2-(1-Boc-2-(R)-pyrrolidinyl)-6-(N-aminomethyl))furo[3,2-b]pyridine from step 121a are added CH$_2$Cl$_2$, triethylamnine and benzoyl chloride. The mixture is stirred at room temperature overnight, then concentrated under vacuum. The residue is chromatographed to afford the title compound.

121c. 6-benzoylaminomethyl-2-(1-Boc-2-(R)-pyrrolidinyl)-furo[3,2-b]pyridine hydrochloride 2-(1-Boc-2-(R)-pyrrolidinyl)-6-(N-benzoylamino)methyl)) furo[3,2-b]pyridine from step 121b was dissolved in CH$_2$Cl$_2$. The mixture was cooled to 0° C., TFA was added and the reaction was stirred for 45 minutes as it warmed to room temperature. The mixture was concentrated in vacuo and taken up in a minimum amount of H$_2$O. The aqueous mixture was basified with 15% NaOH and extracted with CH$_2$Cl$_2$, which was dried (MgSO$_4$) and concentrated. The residue was chromatographed to afford a free base. The isolated free base was taken up in a minimum amount of Et$_2$O, cooled to 0° C., and treated with HCl in EtOH to afford the hydrochloride salt. The material was dried overnight under vacuum to afford a white solid

EXAMPLES 122–127

Following the procedure of Example 121, replacing the 2-(1-Boc-2-(R)-pyrrolidinyl)-6-cyanofuro[3,2-b]pyridine starting material thereof with the starting materials shown in Table 10 below, and replacing the benzoyl chloride of step 121b with the acylating reagent shown in Table 10, the desired compounds 122–127 having L and $R^5$ as described in Table 10 are prepared. L may be selected from R as described previously for groups at that position and R, S or racemic compounds may be prepared from the appropriate precursor. In addition, the cyano group may be further extended via carbon-carbon homologations to form extended alkyl (branched or unbranched) amines which can be further treated with $X(CO)R^5$ or other acylating reagents or alkylating reagents to form, for example, -($C_1$-$C_6$alkyl) amide compounds within the scope of the invention. The nitrogen atom on the left hand side of the molecule should be protected during the acylation process. In Table 10, m is selected from 1–6–e.g., $C_1$–$C_6$.

TABLE 10

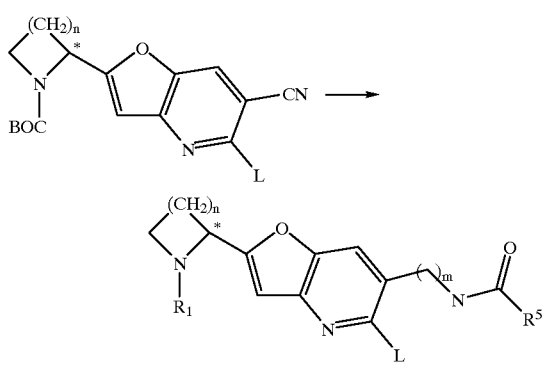

| Ex. No. | n | * | L | Acylating agent | $R^5$ |
|---|---|---|---|---|---|
| 122 | 2 | (R) | H | acetic anhydride | acetyl |
| 123 | 2 | (S) | H | 6-chlorohexanoyl chloride | 6-chlorohexanoyl |
| 124 | 2 | (R) | Cl | ethyl formate | H |
| 125 | 2 | (S) | cl | dimethyl dicarbonate | methoxy |
| 126 | 2 | (R) | H | furoyl chloride | furanyl |
| 127 | 2 | (S) | H | 3-nicotinoyl chloride | 3-pyridyl |

EXAMPLES 128–133

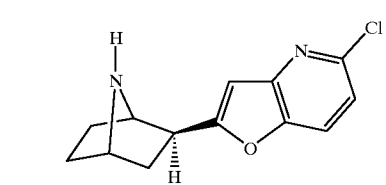

Following the procedure of Example 121, replacing the 2-(1-Boc-2-(R)-pyrrolidinyl)-6-(cyano)-furo[3,2-b]pyridine starting material thereof with the starting materials shown in Table 11 below, and replacing the benzoyl chloride of step 121b with the acylating reagent shown in Table 11, the desired compounds 128–132 having L and $R^5$ as described in Table 11 are prepared. As in the previous examples, L can be selected from the R group of formula I at the designated position and $R^5$ is selected from, for example, those alkanoyl- or benzoylating reagents as listed below or from those reagents of like kind which are known, available or readily prepared. S, R and racemic compounds may be prepared from the appropriate precursor(s). An N-alkyl or suitable protecting group is necessary on the left hand side to permit acylation.

TABLE 11

| Ex.No. | n | * | L | Acylating agent | $R^5$ |
|---|---|---|---|---|---|
| 128 | 2 | (R) | H | 3-phenylpropanoyl chloride | 2-phenylethyl |
| 129 | 2 | (S) | H | chlorobenzoyl chloride | 4-chlorophenyl |
| 130 | 2 | (R) | Cl | 3-nitrobenzoyl chloride | 3-nitrophenyl |
| 131 | 2 | (S) | Cl | 2-pyrrolecarboxylic acid + EDC | 2-pyrrolyl |
| 132 | 2 | (R) | H | 5-nitro-2-furan-carboxylic acid + EDC | 5-nitrofuranyl |
| 133 | 2 | (S) | H | 2-pyrazine-carboxylic acid + EDC | 2-pyrazinyl |

Substituted azacyclic compounds could be also prepared according the Schemes shown above.

The following examples were made according to the procedures described below.

EXAMPLE 134

2-(1-methyl-2-(S)-pyrrolidinyl)furo[2,3-b]pyidine hydrochloride

The title compound was prepared from 2-(1-BOC-2-(S)-pyrrolidinyl)furo[2,3-b]pyridine, from step 1d above, according to the procedures of Example 12 above: H NMR ($D_2O$, 300 MHz) δ 2.35 (m, 2H), 2.60 (m, 2H), 2.95 (s, 3H), 3.35 (m, 2H), 3.81 (m, 1H), 4.83 (m, 1H), 7.24 (s, 1H), 7.46 (m, 1H) 8.22 (m, 1H), 8.36 (dd, J=1.5, 5 Hz, 1H); MS m/z: 203 $(M+H)^+$, 220 $(M+NH_4)^+$; Anal. Calcd for $C_{12}H_{14}N_2O$.1.6 HCl: C, 55.31; H, 6.03 N, 10.75. Found: C, 55.43; H, 6.09 N, 10.54.

EXAMPLE 135

(±)-2-(7-aza-2-exo-bicyclo[2.2.1]heptyl)-5-chlorofuro[3,2-b]pyridine hydrochloride

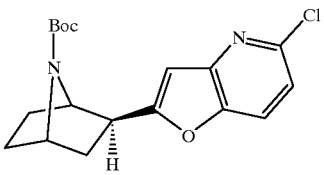

135a. (±)-2-(7-aza-7-(tert-butoxycarbonyl)-2-exo-bicyclo2.2. heptyl)-5-chlorofuro[3,2-b]pyridine 6-Chloro-2-iodo-3-pyridinol (693 mg, 2.71 mmol) from step 11c above, copper(I) iodide (77 mg, 0.41 mmol), bis(triphenylphosphine)palladium(II) chloride (95 mg, 0.14 mmol) and triethylamine (416 mL, 2.98 mmol) were combined in DMF (5.0 mL) and allowed to stir for 1 hour. A solution of (±)-7-(tert-butoxycarbonyl)-2-exo-ethynyl-7-azabicyclo[2.2.1]heptane (600 mg, 2.71 mmol), from step 52d above, in DMF (1 mL) was added and the reaction mixture was heated at 80° C. for 14 hours. After cooling to ambient temperature, the mixture was diluted with Et$_2$O and washed with saturated aqueous NaHCO$_3$ and brine. The organic extract was dried (MgSO$_4$), concentrated and purified by chromatography (silica gel; EtOAc/hexane, 20:80) to afford 596 mg of a mixture of the title compound contaminated with a minor by-product. Further purification by chromatography (silica gel; CH$_2$Cl$_2$/MeOH. 95:5) afforded the pure title compound as a white solid (296 mg, 31%): $^1$H NMR (CDCl$_3$, 300 MHz) δ 1.31 (br s, 9H), 1.45–1.65 (m, 2H), 1.85–2.00 (m, 3H), 2.10 (m, 1H), 3.13 (dd, J=5.1, 8.8 Hz, 1H), 4.41 (br s, 1H), 4.88 (br s, 1 H), 6.58 (d, J=0.8 Hz, 1H), 7.15 (d, J=8.5 Hz, 1H), 7.60 (dd, J=0.8, 8.6 Hz, 1H); MS (CI/NH$_3$) m/z: 349, 351 (M+H)$^+$.

135b. (±)-2-(7-aza-2-exo-bicyclo[2.2.1]heptyl)-5-chlorofuro[3,2-b]pyridine

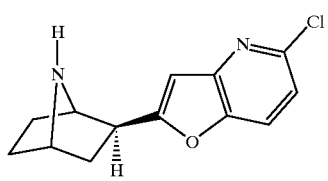

The compound from step 135a above (178 mg, 0.510 mmol) was dissolved in 1:1 CH$_2$Cl$_2$/TFA (4 mL) and stirred at ambient temperature for 45 min. The solvent was removed in vacuo and the residue was diluted with saturated aqueous K$_2$CO$_3$ and extracted with CH$_2$Cl$_2$ (3×). The combined organic extracts were dried (Na$_2$SO$_4$) and concentrated. The crude product was chromatographed (silica gel; CHCl$_3$/MeOH, 90:10) to afford the title compound as a white solid (125 mg, 99%): $^1$H NMR (CDCl$_3$, 300 MHz) δ 1.40–1.60 (m, 2H), 1.66–2.14 (m, 5H), 3.11 (dd, J=5.2, 8.8 Hz, 1H), 3.82–3.86 (m, 2H), 6.55 (s, 1H), 7.15 (d, J=8.5 Hz. 1H), 7.62 (dd, J=0.9, 8.6 Hz, 1H); MS (CI/NH$_3$) m/z: 249, 251 (M+H)$^+$.

135c. (±)-2-(7-aza-2-exo-bicyclo[2.2.1]heptyl)-5-chlorofuro[3,2-b]pyridine hydrochloride

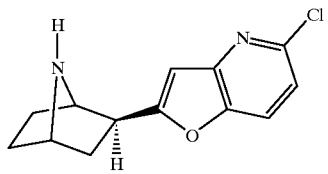

The compound from step 135b above (15 mg, 0.462 mmol) was slurried in 2:1 Et$_2$O/CH$_2$Cl$_2$ (6 mL) and a saturated solution of HCl in Et$_2$O was added dropwise. The solvent was removed and the precipitate was triturated with Et$_2$O and then placed under vacuum to afford the title compound as white solid (117 mg, 89%): mp>260° C.; $^1$H NMR (D$_2$O, 300 MHz) δ 1.89–2.10 (m, 4H), 2.31 (m, 1H), 2.44 (m, 1H), 3.68 (dd, J=5.6, 9.6 Hz, 1H), 4.45 (m, 1H)., 4.60 (d, J=3.7 Hz, 1H), 6.82 (s, 1H), 7.38 (d, J=8.8 Hz, 1H), 7.90 (d, J=8.8 Hz, 1H); MS (CI/NH$_3$) m/z: 249, 251 (M+H)$^+$; Anal. Calcd for C$_{13}$H$_{14}$ClN$_2$O.HCl: C, 54.75 H, 4.95; N, 9.82. Found: C, 54.63; H, 4.85; N, 9.67.

EXAMPLE 136

(±)-2-(7-aza-2-exo-bicyclo[2.2.1]heptyl)-5-fluorofuro[3,2-b]pyridine hydrochloride

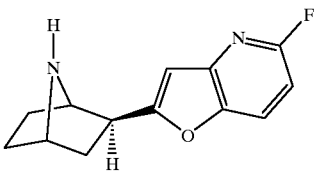

136a. 2-fluoro-5-nitropyridine

2-Chloro-5-nitropridine (100 g, 0.656 mol, Aldrich), spray-dried potassium fluoride (84.1 g, 1.45 mol, Aldrich), tetraphenylphosphonium bromide (95.3 g, 0.227 mol), and anhydrous acetonitrile (1.5 L) were combined and heated at reflux overnight. The volume of the mixture was reduced to 750 mL and the mixture was diluted with 2 L of ether, filtered and then concentrated. The residue was triturated with hot hexane (5×1 L), and the combined hexane extracts were concentrated to give the title compound as a pale yellow oil (48 g, 54%): $^1$H NMR (CDCl$_3$, 300 MHz) δ 7.14 (dd, J=3.5, 9.0 Hz, 1H), 8.63 (m, 1H), 9.15 (d, J=1.6 Hz, 1H).

136b. 5-amino-2-fluoropyridine

2-Fluoro-5-nitropyridine from step 136a above (54.1 g, 379), 62.6 g) was combined with 10% Pd/C (1 g) in EtOH (1.4 L) and the mixture was stirred under H$_2$ (4 atm, 3 h). After filtration, the crude product was combined with that from a similar run (441 mmol) and chromatographed (silica gel; 100% hexane to 50:50 hexane/EtOAc gradient) to afford 74.1 g (81%) of a solid. This material was recrystallized from EtOAc to afford the title compound (67 g, 72%): $^1$H NMR (DMSO-d$_6$, 300 MHz) δ 6.74 (dd, J=3, 6 Hz, 1H), 7.11 (m, 1H), 7.26 (t, J=1 Hz, 1H); MS (DCI/NH$_3$) m/z: 113 (M+H)$^+$, 130 (M+NH$_4$ )$^+$.

136c. 5-diazonium-2-fluoropyridine tetrafluoroborate

5-Amino-2-fluoropyridine from step 136b above (45.5 g, 406 mmol) was dissolved in DME (200 mL) and cooled to −10° C. under an atmosphere of nitrogen. Boron trifluoride etherate (100 mL, 812 mmol) was added dropwise. Then a solution of tert-butyl nitrite (51.0 mL, 490 mmol) in CH$_2$Cl$_2$ (50 mL) was added at a rate which maintained the internal reaction temperature below 0° C. After 20 minutes at −10° C., pentane (250 ml) was added to aid stirring, followed by an additional portion of pentane (250 ml) after 20 minutes. The solid was collected by suction filtration, washed with pentane (2×250 mL) and ether (4×100 mL), and air dried to afford 83.6 g (98%) of the title compound which was immediately used without further purification.

136d. 5-acetoxy-2-fluoropyridine

The diazonium salt from step 136c above (83.6 g) was suspended in acetic anhydride (500 mL) and quickly warmed to 110° C.±5° C. until nitrogen evolution became minimal (approximately 1 hour). The solvent was removed in vacuo with a rotary evaporator (bath temperature 70° C.) and the residue was diluted with Et$_2$O (1 L) and saturated aqueous Na$_2$CO$_3$ (300 mL). The layers were separated and the aqueous phase was extracted with Et$_2$O (4×500 mL). The combined ethereal extracts were dried (MgSO$_4$) and concentrated. Purification by chromatography (silica gel; hexane/EtOAc, 95:5 to 70:30) afforded the title compound (24 g, 38%): $^1$H NMR (CDCl$_3$ 300 MHz) δ 2.32 (s, 3H), 6.96 (dd, J=3, 9 Hz, 1H), 7.59 (m, 1H), 8.03 (dd, J=0.5, 1 Hz, 1H); MS (DCI/NH$_3$) m/z: 156 (M+H)$^+$, 171 (M+NH$_4$)$^+$.

136e. 2-fluoro-5-hydroxypyridine

5-Acetoxy-2-fluoropyridine (70.5 g, 454 mmol) from step 136d above was suspended in 20% aqueous NaOH (200 mL) at 0° C. and stirred at ambient temperature overnight. The solution was neutralized (pH 6) by the addition of concentrated HCl. The aqueous mixture was extracted with EtOAc (5×200 mL), then the combined organic extracts were dried (MgSO$_4$), and concentrated to afford 47.9 g (93%) of a solid. The crude product was recrystallized from EtOAc to afford the title compound as a white solid (30.5 g, 59%). The 2nd and 3rd crops were combined and recrystallized to afford an additional 9.3 g (18%) of the title compound: $^1$H NMR (CDCl$_3$, 300 MHz) δ 6.84 (dd, J=1.9, 5.1 Hz, 1H), 7.43 (m, 1H), 7.81 (t, J=2.8 Hz, 114); MS m/z: 114 (M+H)$^+$, 131 (M+NH$_4$)$^+$.

136f. 6-fluoro-2-iodo-3-pyridinol

The title compound was prepared from 2-fluoro-5-hydroxypyridine (from step 136e above) according to the procedures of step 28d above: $^1$H NMR (DMSO-d$_6$, 300 MHz) δ 7.03 (dd, J=3.9, 8.7 Hz, 1H), 7.30 (dd, J=7.0, 8.6 Hz, 1H), 10.81 (br s, 1H); MS m/z: 240 (M+H)$^+$, 257 (M+NH$_4$)$^+$.

36g. (±)-2-(7-aza-7-(tert-butoxycarbonyl)-2-exo-bicyclo[2.2.1]heptyl)-5-fluorofuro[3,2-b]pyridine

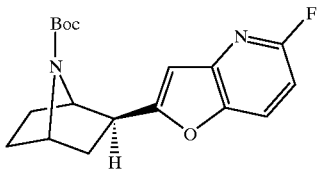

6-Fluoro-2-iodo-3-pyridinol (860 mg, 3.60 mmol) from step 136f, copper(I) iodide (103 mg, 0.540 mmol), bis(triphenylphosphine)palladium(II) chloride (126 mg, 0.180 mmol) and triethylamine (552 mL, 3.96 mmol) were combined in DMF (6 mL) and allowed to stir for 1 hour. A solution of (±)-7-(tert-butoxycarbonyl)-2-exo-ethynyl-7-azabicyclo[2.2.1]heptane (796 mg, 3.60 mmol), from step 52d above, in DMF (1 mL) was added and the reaction mixture was heated at 80° C. for 14 hours. After cooling to ambient temperature, the mixture was diluted with Et$_2$O and washed with saturated aqueous NaHCO$_3$ and brine. The organic extract was dried (MgSO$_4$), concentrated and purified by chromatography (silica gel: MeOH/CH$_2$Cl$_2$, 2:98 to 5:95) to afford the title compound as a white solid (277 mg, 23%): mp 96–98° C.; $^1$H NMR (CDCl$_3$, 300 MHz) δ 1.29 (br s, 9H), 1.40–1.65 (m, 2H), 1.80–2.00 (m, 3H), 2.10 (m, 1H), 3.13 (dd, J=5.1, 8.8 Hz, 1H), 4.42 (br s, 1H), 4.49 (br s, 1 H), 6.55 (s, 1H), 6.76 (dd, J=1.5, 8.7 Hz, 1H), 7.71 (m, 1H); MS (CI/NH$_3$) n/z: 333 (M+H)$^+$.

36h. (±)-2-(7-aza-2-exo-bicyclo[2.2.1]heptyl)-5-fluorofuro[3,2-b]pyridine

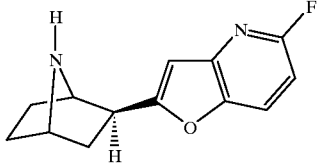

The compound from4 0.737 mmol) was dissolved in 1:1 CH$_2$Cl$_2$/TFA (6 mL) and stirred at ambient temperature for 30 minutes. The solvent was removed in vacuo and the residue was partitioned between CH$_2$Cl$_2$ and saturated aqueous K$_2$CO$_3$. The organic extract was dried (Na$_2$SO$_4$) and concentrated. The crude product was chromatographed (silica gel; CHCl$_3$/MeOH, 90:10) to afford the title compound as a white solid (153 mg, 89%): mp 104–106° C.; $^1$H NMR (CDCl$_3$, 300 MHz) δ 1.40–1.56 (m, 2H), 1.67–1.78 (m, 2H), 1.85 (m, 1H), 1.98 (m, 1H), 2.11 (br s, 1H), 3.10 (dd, J=5.1, 8.8 Hz, 1H), 3.83–3.86 (m, 2H), 6.52 (m, 1H), 6.75 (dd, J=1.7, 8.8 Hz, 1H), 7.72 (ddd, J=0.8, 6.4, 7.3 Hz, 1H); MS (CI/NH$_3$) m/z: 233 (M+H)$^+$.

36i. (±)-2-(7-aza-2-exo-bicyclo[2.2.1]heptyl)-5-fluorofuro[3,2-b]pyridine hydrochloride

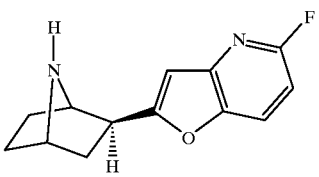

The compound from step 136h above (144 mg, 0.620 mmol) was slurried in Et$_2$O and a saturated solution of HCl in Et$_2$O was added dropwise. The solvent was removed and the precipitate was triturated with Et$_2$O and then placed under vacuum to afford the title compound as white solid (160 mg, 96%): m/p>260° C.; $^1$H NMR (D$_2$O, 300 MHz) δ 1.93–2.15 (m, 4H), 2.27–2.50 (m, 2H), 3.68 (m, 1H), 4.45 (br s, 1H), 4.60 (m, 1H), 6.80 (br s, 1H), 7.00 (br d, J=8.8 Hz, 1H), 8.03 (m, 1H); MS (CI/NH$_3$) m/z: 233 (M+H)$^+$; Anal. Calcd for C$_{13}$H$_{14}$FN$_2$O.HCl: C, 58.11 H, 5.25; N, 10.42. Found: C, 57.95; H, 4.95; N, 10.23.

The preferred compounds are those designated as Examples 15, 23, 26, 55 and 58 which are the most potent binders to the nicotinic acetylcholine receptor. The preferred use of compounds of the invention is as a nicotinic acethycholine receptor modulator as described herein. The preferred compounds, for the most part, have a chlorine at the 5-position of the moiety and, thus, the preferred class of compounds is directed thereto.

We claim:

1. A compound of formula (I)

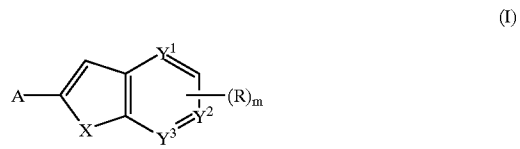

(I)

or a pharmaceutically acceptable salt or pro-drug thereof wherein:

A is selected from the group consisting of:

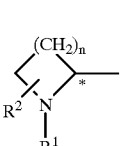

(a)

wherein

*denotes a chiral center, n is 1,2 or 3,

R$^1$ is selected from the group consisting of H, allyl and C$_1$–C$_3$-alkyl;

R$^2$ is selected from the group consisting of

H,
$C_1$–$C_3$-alkyl,
$C_1$–$C_3$-alkoxyl,
hydroxymethyl,
fluoromethyl,
methoxymethyl, and, $R^2$ when substituted at a position other than alpha to the ring nitrogen atom is selected from Br, Cl, F, OH, CN, —O—CO—$CH_3$ and
—O-methanesulfonyl;

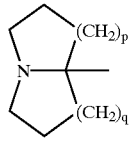

wherein p and q are independently 1 or 2;

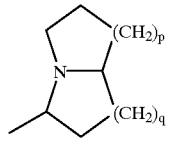

wherein p and q are independently 1 or 2; and

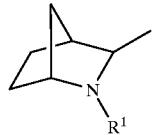

R is independently selected at each occurrence from the group consisting of
$C_1$–$C_4$-alkyl,
vinyl,
bromo,
chloro,
fluoro,
trifluoro-$C_1$–$C_4$-alkyl,
trichloro-$C_1$–$C_4$-alkyl,
COOH,
$CO_2$—$C_1$–$C_4$-alkyl,
CN,
nitro,
amino,
hydroxy,
NH—CO—$C_1$–$C_3$-alkyl, and
$NR^3R^3$, wherein $R^3$ is H or $C_1$–$C_3$-alkyl;

or, when substituted at the $Y^2$ position R can additionally be selected from:
$NR^3R^4$, wherein $R^3$ is H or C1–C3 alkyl and $R^4$ is hydrogen, $C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;
C(O)—$R^5$, where $R^5$ is hydrogen, $C_1$–$C_8$-alkyl, substituted-$C_1$–$C_8$-alkyl, phenyl, substituted-phenyl, naphthyl, substituted naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, substituted-heteroaryl-$C_1$–$C_6$-alkyl-, and
O—$C_1$–$C_6$-alkyl-, N—$R^6R^7$, wherein $R^6$ is selected from the group consisting of H and $C_1$–$C_3$-alkyl-, and $R^7$ is selected from the group consisting of H, $C_1$–$C_3$-alkyl-, phenyl and substituted-phenyl;
$OR^8$, wherein $R^8$ is $C_1$–$C_8$-alkyl, phenyl, substituted-phenyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, $CONR^3R^4$;
phenyl;
naphthyl;
substituted-phenyl;
substituted-naphthyl;
biphenyl;
substituted-biphenyl;
heteroaryl;
substituted-heteroaryl;
phenyl-$C_1$–$C_6$-alkyl-;
substituted-phenyl-$C_1$–$C_6$-alkyl-;
heteroaryl-$C_1$–$C_6$-alkyl-; and
substituted-heteroaryl-$C_1$–$C_6$-alkyl-;

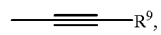

wherein $R^9$ is selected from the group consisting of hydrogen, $C_1$–$C_8$-alkyl, substituted-$C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;

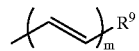

wherein m is 1 or 2, and $R^9$ is as defined above;
—$CH_2$—NH—CO—$R^5$, wherein $R^5$ is as defined above; and
—$CH_2$—$CH_2$—CO—O—$C_1$–$C_6$-alkyl;
X is —O—, —S— or —$NR^3$, wherein $R^3$ is H or $C_1$–$C_3$-alkyl;
m on formula (I) is 0, 1, 2 or 3;
$Y^1$, $Y^2$ and $Y^3$ are N or CH, with the provisos that one of $Y^1$, $Y^2$ and $Y^3$ is N.

2. A compound according to claim 1 of the formula:

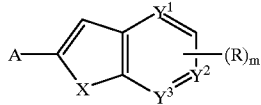

(I)

or a pharmaceutically acceptable salt or pro-drug thereof wherein:
A is selected from the group consisting of:

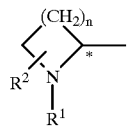

(a)

wherein
*denotes a chiral center, m is 0, 1 or 2;
n is 1, 2 or 3,
R¹ is selected from the group consisting of H and C₁–C₃-alkyl, and
R² is H, or when n is 2 or 3 is selected from the group consisting of
C₁–C₃-alkyl,
C₁–C₃-alkoxyl,
hydroxymethyl,
fluoromethyl,
methoxymethyl, or at a position other than alpha to the nitrogen may additionally be selected from,
Br,
Cl,
F,
OH,
CN,
—O—CO—CH₃ and
—O-methanesulfonyl;

(c) 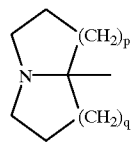

wherein p and q are independently 1 or 2;

(d) 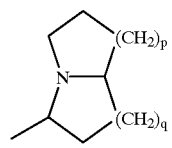

wherein p and q are independently 1 or 2; and (e) 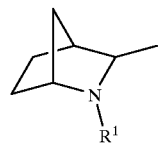

R is independently selected at each occurrence from the group consisting of
C₁–C₄-alkyl,
bromo,
chloro,
fluoro,
trifluoro-C₁–C₄-alkyl,
trichloro-C₁–C₄-alkyl,
COOH,
CO₂—C₁–C₄-alkyl,
CN,
nitro,
amino,
NH—CO—C₁–C₃-alkyl, and
NR³R³, wherein R³ is H or C₁–C₃-alkyl;
X is —O—, —S— or —NR³, wherein R³ is H or C₁–C₃-alkyl;
Y¹, Y² and Y³ are N or CH, with the provisos that one of Y¹, Y² and Y³ is N.

3. A compound according to claim 1 of formula (III):

(III) 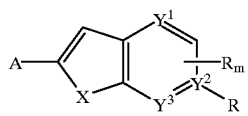

or a pharmaceutically acceptable salt or pro-drug thereof wherein:

A is selected from the group consisting of:

(a) 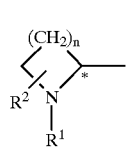

wherein
*denotes a chiral center,
n is 1, 2 or 3,
R¹ is selected from the group consisting of H, allyl and C₁–C₃-alkyl;
R² is selected from the group consisting of
H,
C₁–C₃-alkyl,
C₁–C₃-alkoxyl,
hydroxymethyl,
fluoromethyl,
methoxymethyl, and, R² when substituted at a position other than alpha to the ring nitrogen atom is selected from Br, Cl, F, OH, CN, —O—CO—CH₃ and
—O-methanesulfonyl;

(c) 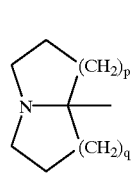

wherein p and q are independently 1 or 2;

(d) 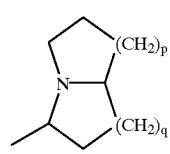

wherein p and q are independently 1 or 2; and (e) 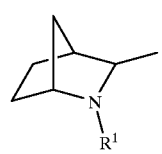

R is independently selected at each occurrence from the group consisting of $C_1$–$C_4$-alkyl,
vinyl,
bromo,
chloro,
fluoro,
trifluoro-$C_1$–$C_4$-alkyl,
trichloro-$C_1$–$C_4$-alkyl,
COOH,
$CO_2$—$C_1$–$C_4$-alkyl,
CN,
nitro,
amino,
hydroxy,
NH—CO—$C_1$–$C_3$-alkyl, and
$NR^3R^3$, wherein $R^3$ is H or $C_1$–$C_3$-alkyl; and, at the $Y^2$ position, R can additionally be selected from:
  $NR^3R^4$, wherein $R^3$ is H or C1–C3 alkyl and $R^4$ is hydrogen, $C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;
  C(O)—$R^5$ where $R^5$ is hydrogen, $C_1$–$C_8$-alkyl, substituted-$C_1$–$C_8$-alkyl, phenyl, substituted-phenyl, naphthyl, substituted naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, substituted-heteroaryl-$C_1$–$C_6$-alkyl-, and O—$C_1$–$C_6$-alkyl-, N—$R^6R^7$, wherein $R^6$ is selected from the group consisting of H and $C_1$–$C_3$-alkyl-, and $R^7$ is selected from the group consisting of H, $C_1$–$C_3$-alkyl-, phenyl and substituted-phenyl;
  $OR^8$, wherein $R^8$ is $C_1$–$C_8$-alkyl, phenyl, substituted-phenyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, $CONR^3R^4$;
  phenyl;
  naphthyl;
  substituted-phenyl;
  substituted-naphthyl;
  biphenyl;
  substituted-biphenyl;
  heteroaryl;
  substituted-heteroaryl;
  phenyl-$C_1$–$C_6$-alkyl-;
  substituted-phenyl-$C_1$–$C_6$-alkyl-;
  heteroaryl-$C_1$–$C_6$-alkyl-; and
  substituted-heteroaryl-$C_1$–$C_6$-alkyl-;

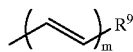

wherein $R^9$ is selected from the group consisting of hydrogen, $C_1$–$C_8$-alkyl, substituted-$C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-hetcroaryl-$C_1$–$C_6$-alkyl-;

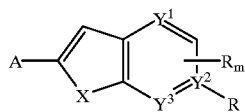

wherein m is 1 or 2, and $R^9$ is as defined above;
—$CH_2$—NH—CO—$R^5$, wherein $R^5$ is as defined above; and
—$CH_2$—$CH_2$—CO—O—$C_1$–$C_6$-alkyl;

X is —O—, —S— or —$NR^3$, wherein $R^3$ is H or $C_1$–$C_3$-alkyl;

m is 0, 1 or 2;

$Y^1$, $Y^2$ and $Y^3$ are N or CH, with the provisos that one of $Y^1$, $Y^2$ and $Y^3$ is N.

4. A compound according to claim 3 of formula (III):

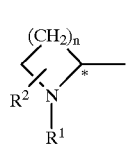

(III)

or a pharmaceutically acceptable salt or pro-drug thereof wherein:

A is selected from the group consisting of:

(a)

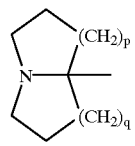

wherein
*denotes a chiral center,
n is 1, 2 or 3,
$R^1$ is selected from the group consisting of H, allyl and $C_1$–$C_3$-alkyl;
$R^2$ is selected from the group consisting of
  H,
  $C_1$–$C_3$-alkyl,
  $C_1$–$C_3$-alkoxyl,
  hydroxymethyl,
  fluoromethyl,
  methoxymethyl, and, $R^2$ when substituted at a position other than alpha to the ring nitrogen atom is selected from Br, Cl, F, OH, CN,
  —O—CO—$CH_3$ and
  —O-methanesulfonyl;

(c)

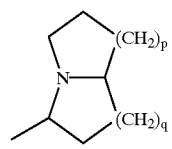

wherein p and q are independently 1 or 2;

(d)

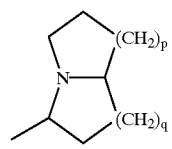

wherein p and q are independently 1 or 2; and

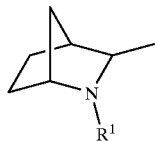

(e)

R is independently selected at each occurrence from the group consisting of
$C_1$–$C_4$-alkyl,
vinyl,
bromo,
chloro,
fluoro,
trifluoro-$C_1$–$C_4$-alkyl,
trichloro-$C_1$–$C_4$-alkyl,
COOH,
$CO_2$—$C_1$–$C_4$-alkyl,
CN,
nitro,
amino,
hydroxy,
NH—CO—$C_1$–$C_3$-alkyl, and
$NR^3R^3$, wherein $R^3$ is H or $C_1$–$C_3$-alkyl; and, at the $Y^2$ position, R can additionally be selected from:
  $NR^3R^4$, wherein $R^3$ is H or C1–C3 alkyl and $R^4$ is hydrogen, $C_1$–$C_8$-alkyl, phenyl, substituted-phenyl, naphthyl, substituted-naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, and substituted-heteroaryl-$C_1$–$C_6$-alkyl-;
  $C(O)$—$R^5$, where $R^5$ is hydrogen, $C_1$–$C_8$-alkyl, substituted-$C_1$–$C_8$-alkyl, phenyl, substituted-phenyl, naphthyl, substituted naphthyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, substituted-heteroaryl-$C_1$–$C_6$-alkyl-, and O—$C_1$–$C_6$-alkyl-, N-$R^6R^7$, wherein $R^6$ is selected from the group consisting of H and $C_1$–$C_3$-alkyl-, and $R^7$ is selected from the group consisting of H, $C_1$–$C_3$-alkyl-, phenyl and substituted-phenyl;
  $OR^8$, wherein $R^8$ is $C_1$–$C_8$-alkyl, phenyl, substituted-phenyl, heteroaryl, substituted-heteroaryl, phenyl-$C_1$–$C_6$-alkyl-, substituted-phenyl-$C_1$–$C_6$-alkyl-, heteroaryl-$C_1$–$C_6$-alkyl-, $CONR^3R^4$;
  phenyl;
  naphthyl;
  substituted-phenyl;
  substituted-naphthyl;
  biphenyl;
  substituted-biphenyl;
  heteroaryl;
  substituted-heteroaryl;
  phenyl-$C_1$–$C_6$-alkyl-;
  substituted-phenyl-$C_1$–$C_6$-alkyl-;
  heteroaryl-$C_1$–$C_6$-alkyl-; and
  substituted-heteroaryl-$C_1$–$C_6$-alkyl-;
  of hydrogen, $C_1$–$C_8$-alkyl, substituted-$C_1$–$C_8$-alkyl, phenyl, substituted-phenyl, naphthyl, substituted-naphthyl, heteroaryl, substituted-heteroaryl, phenyl-$C_1$–$C_6$-alkyl-, subsitituted-phenyl-$C_1$–$C_6$-alkyl-, heteroaryl-$C_1$–$C_6$-alkyl-, and substituted-heteroaryl-$C_1$–$C_6$-alkyl-;

wherein m is 1 or 2, and $R^9$ is as defined above;
—$CH_2$—NH—CO—$R^5$, wherein $R^5$ is as defined above; and
—$CH_2$—$CH_2$—CO—O—$C_1$–$C_6$-alkyl;
X is —O—, —S— or —$NR^3$, wherein $R^3$ is H or $C_1$–$C_3$-alkyl;
m on formula (III) is 0 or 1;
$Y^1$, $Y^2$ and $Y^3$ are N or CH, with the provisos that one of $Y^1$, $Y^2$ and $Y^3$ is N.
5. A compound as defined by claim 1 having the formula

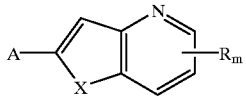

or a pharmaceutically acceptable salt or pro-drug thereof wherein X, A, R and m are as defined therein.
6. A compound as defined by claim 5 wherein A is selected from the group consisting of

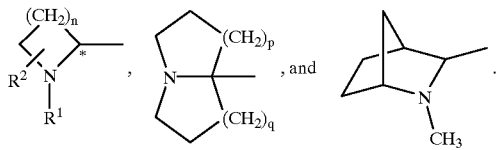

or a pharmaceutically acceptable salt or pro-drug thereof.
7. A compound as defined by claim 6 wherein $R_m$ is at the position designated as Y2 in formula I and is selected from phenyl, 4-pyridyl-2-ethenyl, pyridyl and benzoylaminomethyl.
8. A compound defined by claim 1 or 2 wherein R is selected from the group consisting of Cl and $C_1$–$C_4$-alkyl or m is equal to 0 or a pharmaceutically acceptable salt or pro-drug thereof.
9. A compound as defined by claim 1 selected from the group consisting of
  2-(1-methyl-2-(S)-pyrrolidinyl)furo [3,2-b]pyridine;
  2-(2-(S)-pyrrolidinyl)furo[3,2-b]pyridine;
  2-(2-(R)-pyrrolidinyl)furo[3,2-b]pyridine;
  2-(1-methyl-2-(R)-pyrrolidinyl)furo[3,2-b]pyridine;
  5-methyl-2-(2-(S)-pyrrolidinyl)furo[3,2-b]pyridine;
  2-(1-methyl-2-(S)-pyrrolidinyl)-5-methylfuro[3,2-b]pyridine;
  6-chloro-2-(2-(S)-pyrrolidinyl)furo[3,2-b]pyridine;
  6-chloro-2-(1-methyl-2-(S)-pyrrolidinyl)furo[3,2-b]pyridine;
  2-(2-(S)-pyrrolidinyl)furo[2,3-c]pyridine;
  2-(1-methyl-2-(S)-pyrrolidinyl)furo[2,3-c]pyridine;
  5-chloro-2-(2-(S)-pyrrolidinyl)furo[3,2-b]pyridine;
  5-chloro-2-(1-methyl-2-(S)-pyrrolidinyl)furo[3,2-b]pyridine;
  5-chloro-2-(2-(S)-pyrrolidinyl)furo[2,3-b]pyridine;
  5-chloro-2-(1-methyl-2-(S)-pyrrolidinyl)-furo[2,3-b]pyridine;
  2-(hexahydro-1H-7a-pyrrolizinyl)furo[3,2-b]pyridine;
  2-(hexahydro-1H-7a-pyrrolizinyl)-5-methylfuro[3,2-b]pyridine;
  2-(hexahydro-1H-7a-pyrrolizinyl)furo[2,3-c]pyridine;
  endo-2-(hexahydro-1H-3-(R)-pyrrolizinyl)furo[2,3-c]pyridine;

exo-2-(hexahydro-1H-3-(S)-pyrrolizinyl)furo[2,3-c]
pyridine;
exo-2-(hexahydro-1H-3-(R)-pyrrolizinyl)furo[2,3-c]
pyridine;
endo-2-(hexahydro-1H-3-(S)-pyrrolizinyl)furo[2,3-c]
pyridine;
[2-(1-pyrrolidinylinethyl)furo(3,2-b) pyridine;]
5-chloro-2-(hexahydro-1H-7a-pyrrolizinyl)furo[3,2-b]
pyridine;
2-(hexahydro-1H-7a-pyrrolizinyl)thieno[3,2-b]pyridine;
5,6-dichloro-2-(2-(S)-pyrrolidinyl)furo[3,2-b]pyridine;
5,6-dichloro-2-(1-methyl-2-(S)-pyrrolidinyl)furo[3,2-b]
pyridine;
2-(hexahydro-1H-7a-pyrrolizinyl)-4-methylthieno[3,2-b]
pyridine;
5-bromo-2-(2-(S)-pyrrolidinyl) furo[3,2-b]pyridine;
5-methyl-2-(2-(R)-pyrrolidinyl)furo[3,2-b]pyridine;
2-(1-methyl-2-(R)-pyrrolidinyl)-5-methylfuro[3,2-b]
pyridine;
6-chloro-2-(2-(R)-pyrrolidinyl)furo [3,2-b]pyridine;
5-chloro-2-(1-methyl-2-(R)-pyrrolidinyl) furo[3,2-b]
pyridine;
5-bromo-2-(2-(R)-pyrrolidinyl) furo [3,2-b]pyridine;
2-(2-(R)-pyrrolidinyl)furo [2,3-c]pyridine;
5-chloro-2-(2-(R)-pyrrolidinyl)furo[3,2-b]pyridine;
2-(2-(S)-pyrrolidinyl)furo[2,3-b]pyridine;
2-(1-methyl-2-(S)-pyrrolidinyl)furo[3,2-c]pyridine;
5,6-dichloro-2-(hexahydro-1H-7a-pyrrolizinyl)-furo[3,2-b]pyridine;
5,6-dichloro-2-(2-(R)-pyrrolidinyl)furo[3,2-b]pyridine;
5,6-dichloro-2-(1-methyl-2-(R)-pyrrolidinyl)furo[3,2-b]
pyridine;
2-((1R,4S)-2-aza-3-(S)-bicyclo[2.2.1]heptyl) furo[3,2-b]
pyridine;
2-((1R,4S)-2-aza-3-(S)-bicyclo[2.2.1 ]heptyl)-2-methylfuro[3,2-b]pyridine;
2-((1R,4S)-2-aza-3-(S)-bicyclo[2.2.1]heptyl)-5-chlorofuro[3,2-b]pyridine;
2-((1R,4S)-2-aza-2-methyl-3-(S)-bicyclo[2.2.1]heptyl)-5-chloro furo [3,2-b]pyridine;
2-((1R,4S)-2-aza-3-(S)-bicyclo[2.2.1]heptyl)-5,6-dichloro furo[3,2-b]pyridine;
6-bromo-2-(2-(S)-pyrrolidinyl)furo[3,2-b]pyridine;
6-bromo-2-(1-methyl-2-(S)-pyrrolidinyl)furo[3,2-b]
pyridine;
6-bromo-5-chloro-2-(1-methyl-2-(S)-pyrrolidinyl)furo[3,2-b]pyridine;
6-bromo-5-chloro-2-(2-(R)-pyrrolidinyl)furo [3,2-b]
pyridine;
6-bromo-5-chloro-2-(1-methyl-2-(R)-pyrrolidinyl)furo[3,2-b]pyridine;
7-chloro-2-(1-methyl-2-(S)-pyrrolidinyl)furo[3,2-b]
pyridine;
2-(1-methyl-2-(S)-pyrrolidinyl)furo(2,3-b)pyridine
hydrochloride;
(±)-2-aza-2-exo-bicyclo(2.2.1)heptyl)-5-fluorofuro(3,2-b)pyridine hydrochloride; 6-phenyl-2-((S)-pyrrolidinyl)furo[3,2-b]pyridine dihydrochloride;
6-phenyl-2-(1-methyl-2-(S)-pyrrolidinyl)furo[3,2-b]
pyridine dihydrochloride;
5-chloro-6-phenyl-2-(2-(R)-pyrrolidinyl)furo(3,2-b)
pyridine hydrochloride;
5-chloro-2-(1-methyl-2-(R)-pyrrolidinyl)-6-phenylfuro
(3,2-b)pyridine hydrochloride; (3-aminophenyl)-5-chloro-2-(2-(R)-pyrrolidinyl)-6-furo(3,2-b)pyridine
hydrochloride;
5-chloro-2-(2-(R)-pyrrolidinyl)-6-(4-vinylpyridyl)-furo
(3,2-b)pyridine hydrochloride; and
5-chloro-2-(1-methyl-2-(S)-pyrrolidinyl)-6-(3-pyridyl)-furo(3,2-b)pyridine hydrochloride or
a pharmaceutically acceptable salt or prodrug thereof.

10. A compound as defined by claim 6 selected from the group consisting of 2-(1-methyl-2-(S)-pyrrolidinyl)furo[3,2-b]pyridine;
2-(2-(S)-pyrrolidinyl)furo[3,2-b]pyridine;
2-(2-(R)-pyrrolidinyl)furo[3,2-b]pyridine;
2-(1-methyl-2-(R)-pyrrolidinyl)furo[3,2-b]pyridine;
5-methyl-2-(2-(S)-pyrrolidinyl)furo[3,2-b]pyridine;
2-(1-methyl-2-(S)-pyrrolidinyl)-5-methylfuro[3,2-b]
pyridine;
6-chloro-2-(2-(S)-pyrrolidinyl) furo[3,2-b]pyridine;
6-chloro-2-(1-methyl-2-(S)-pyrrolidinyl) furo[3,2-b]
pyridine;
5-chloro-2-(2-(S)-pyrrolidinyl) furo[3,2-b]pyridine;
5-chloro-2-(1-methyl-2-(S)-pyrrolidinyl) furo[3,2-b]
pyridine;
5-chloro-2-(hexahydro-1H-7a-pyrrolizinyl) furo[3,2-b]
pyridine;
2-(hexahydro-1H-7a-pyrrolizinyl)thieno[3,2-b]pyridine;
5,6-dichloro-2-(2-(S)-pyrrolidinyl) furo[3,2-b]pyridine;
5,6-dichloro-2-(1-methyl-2-(S)-pyrrolidinyl) furo[3,2-b]
pyridine;
2-(hexahydro-1H-7a-pyrrolizinyl)-4-methylthieno[3,2-b]
pyridine;
5-bromo-2-(2-(S)-pyrrolidinyl) furo[3,2-b]pyridine;
5-methyl -2-(2-(R)-pyrrolidinyl)-furo[3,2-b]pyridine;
2-(1-methyl-2-(R)-pyrrolidinyl)-5-methyl furo[3,2-b]
pyridine;
6-chloro-2-(2-(R)-pyrrolidinyl) furo[3,2-b]pyridine;
5-chloro-2-(1-methyl-2-(R)-pyrrolidinyl) furo[3,2-b]
pyridine;
5-bromo-2-(2-(R)-pyrrolidinyl) furo[3,2-b]pyridine;
2-(2-(R)-pyrrolidinyl)-5-chlorofuro[3,2-b]pyridine;
2-(hexahydro-1H-7a-pyrrolizinyl)-5,6-dichlorofuro[3,2-b]pyridine;
5,6-dichloro-2-(2-(R)-pyrrolidinyl)furo[3,2-b]pyridine;
5,6-dichloro-2-(1-methyl-2-(R)-pyrrolidinyl)furo[3,2-b]
pyridine;
6-bromo-2-(2-(S)-pyrrolidinyl)furo[3,2-b]pyridine;
6-bromo-2-(1-methyl-2-(S)-pyrrolidinyl)furo[3,2-b]
pyridine;
6-bromo-5-chloro-2-(1-methyl-2-(S)-pyrrolidinyl)furo[3,2-b]pyridine;
6-bromo-5-chloro-2-(2-(R)-pyrrolidinyl)furo[3,2-b]
pyridine;
6-bromo-5-chloro-2-(1-methyl-2-(R)-pyrrolidinyl)furo[3,2-b]pyridine;
7-chloro-2-(1-methyl-2-(S)-pyrrolidinyl)furo[3,2-b]
pyridine;

2-((1R,4S)-2-aza-2-methyl-3-(S)-bicyclo[2.2.1]heptyl)furo[3,2-b]pyridine; or a pharmaceutically acceptable salt or prodrug thereof.

11. A compound as defined by claim 8 selected from the group consisting of 2-(1-methyl-2-(S)-pyrrolidinyl)furo[3,2-b]pyridine;

2-(2-(S)-pyrrolidinyl)furo[3,2-b]pyridine;

2-(2-(R)-pyrrolidinyl)furo[3,2-b]pyridine;

2-(1-methyl-2-(R)-pyrrolidinyl)furo[3,2-b]pyridine;

5-methyl-2-(2-(S)-pyrrolidinyl)furo[3,2-b]pyridine;

2-(1-methyl-2-(S)-pyrrolidinyl)-5-methylfuro[3,2-b]pyridine;

6-chloro-2-(2-(S)-pyrrolidinyl)furo[3,2-b]pyridine;

6-chloro-2-(1-methyl-2-(S)-pyrrolidinyl)furo[3,2-b]pyridine;

5-chloro-2-(2-(S)-pyrrolidinyl)furo[3,2-b]pyridine;

5-chloro-2-(1-methyl-2-(S)-pyrrolidinyl)furo[3,2-b]pyridine;

5-chloro-2-(hexahydro-1H-7a-pyrrolizinyl)furo[3,2-b]pyridine;

5,6-dichloro-2-(2-(S)-pyrrolidinyl)furo[3,2-b]pyridine;

5,6-dichloro-2-(1-methyl-2-(S)-pyrrolidinyl)furo[3,2-b]pyridine;

5-methyl2-(2-(R)-pyrrolidinyl)furo[3,2-b]pyridine;

2-(1-methyl-2-(R)-pyrrolidinyl)-5-methylfuro[3,2-b]pyridine;

6-chloro-2-(2-(R)-pyrrolidinyl)furo[3,2-b]pyridine;

5-chloro2-(1-methyl-2-(R)-pyrrolidinyl)furo[3,2-b]pyridine;

5-chloro-2-(2-(R)-pyrrolidinyl)-furo[3,2-b]pyridine;

5,6-dichloro-2-(hexahydro-1H-7a-pyrrolizinyl)furo[3,2-b]pyridine;

5,6-dichloro-2-(2-(R)-pyrrolidinyl)furo[3,2-b]pyridine;

5,6-dichloro-2-(1-methyl-2-(R)-pyrrolidinyl)furo[3,2-b]pyridine;

7-chloro-2-(1-methyl-2-(S)-pyrrolidinyl)furo[3,2-b]pyridine;

6-bromo-2-(2-(S)-pyrrolidinyl)furo[3,2-b]pyridine;

6-bromo-2-(1-methyl-2-(S)-pyrrolidinyl)furo[3,2-b]pyridine;

6-bromo-5-chloro-2-(1-methyl-2-(S)-pyrrolidinyl)furo[3,2-b]pyridine;

6-bromo-5-chloro-2-(2-(R)-pyrrolidinyl)furo[3,2-b]pyridine;

6-bromo-5-chloro-2-(1-methyl-2-(R)-pyrrolidinyl)furo[3,2-b]pyridine; and 2-((1R,4S)-2-aza-2-methyl-3-(S)-bicyclo[2.2.1]heptyl)furo[3,2-b]pyridine; or a pharmaceutically acceptable salt or prodrug thereof.

12. A compound according to claim 4 selected from the group consisting of 6-phenyl-2-((S)-pyrrolidinyl)furo[3,2-b]pyridine dihydrochloride;

2-(1-methyl-2-(S)-pyrrolidinyl)-6-phenylfuro[3,2-b]pyridine dihydrochloride;

5-chloro-6-phenyl-2-(2-(R)-pyrrolidinyl)furo[3,2-b]pyridine hydrochloride;

5-chloro-6-phenyl-2-(1-methyl-2-(R)-pyrrolidinyl)furo[3,2-b]pyridine hydrochloride;

6-(3-aminophenyl)-5-chloro-2-(2-(R)-pyrrolidinyl)-furo[3,2-b]pyridine hydrochloride;

5-chloro-2-(2-(R)-pyrrolidinyl)-6-(4-pyridyl-2-ethenyl)furo[3,2-b]pyridine hydrochloride; and 5-chloro-2-(1-methyl-2-(S)-pyrrolidinyl)-6-(3-pyridyl)-furo[3,2-b]pyridine hydrochloride or a pharmaceutically acceptable salt or prodrug thereof.

13. A pharmaceutical composition comprising a pharmaceutically effective amount of a compound according to claim 1 or 2 in combination with a pharmaceutically acceptable carrier.

14. A method of modulating chemical synaptic transmission in a mammal comprising administering to a mammal in need of such treatment an effective amount of a compound as defined by claim 1 or 2.

\* \* \* \* \*

UNITED STATES PATENT AND TRADEMARK OFFICE
CERTIFICATE OF CORRECTION

PATENT NO.   : 6,001,849
DATED        : December 14, 1999
INVENTOR(S)  : Richard L. Elliott et al.

It is certified that error appears in the above-identified patent and that said Letters Patent is hereby corrected as shown below:

Column 86,
Line 46, replace "$(R)_m$" with -- $R_m$ --.

Column 88,
Line 50, replace "$(R)_m$" with -- $R_m$ --.

Column 89,
Line 38, replace "wherein p and q are independently 1 or 2; and" with -- wherein p and q are independently 1 or 2; --.

Column 90,
Line 57, replace "wherein p and q are independently 1 or 2; and" with -- wherein p and q are independently 1 or 2; --.

Column 91,
Line 59, replace "hetcroaryl" with -- heteroaryl --.

Column 93,
Line 1, replace "wherein p and q are independently 1 or 2; and" with -- wherein p and q are independently 1 or 2; --.
Line 62, replace "of hydrogen" with wherein $R^9$ is selected from the group consisting of hydrogen, --.

Column 94,
Line 1 replace "wherein m is 1 or 2, and $R^9$ is as defined above;" with wherein m is 1 or 2, and $R^9$ is as defined above; --.

UNITED STATES PATENT AND TRADEMARK OFFICE
CERTIFICATE OF CORRECTION

PATENT NO. : 6,001,849
DATED : December 14, 1999
INVENTOR(S) : Richard L. Elliott et al.

It is certified that error appears in the above-identified patent and that said Letters Patent is hereby corrected as shown below:

Column 95,
Line 7, replace "(1-pyrrolidinylinethyl)" with -- (1-pyrrolidinylmethyl) --.

Column 97,
Line 24, replace "methyl2" with -- methyl-2 --.
Line 28 replace "chloro2" with -- chloro-2 --.

Signed and Sealed this

Fourth Day of December, 2001

*Attest:*

*Attesting Officer*

NICHOLAS P. GODICI
*Acting Director of the United States Patent and Trademark Office*